US012559488B2

(12) United States Patent
Li et al.

(10) Patent No.: US 12,559,488 B2
(45) Date of Patent: Feb. 24, 2026

(54) SUBSTITUTED MORPHOLINES AS ATR KINASE INHIBITORS

(71) Applicants: JIANGSU HENGRUI MEDICINE CO., LTD., Lianyungang (CN); SHANGHAI HENGRUI PHARMACEUTICAL CO., LTD., Shanghai (CN)

(72) Inventors: Xin Li, Shanghai (CN); Huaide Dong, Shanghai (CN); Dongdong Bai, Shanghai (CN); Feng He, Shanghai (CN); Weikang Tao, Shanghai (CN)

(73) Assignees: JIANGSU HENGRUI MEDICINE CO., LTD., Lianyungang (CN); SHANGHAI HENGRUI PHARMACEUTICAL CO., LTD., Shanghai (CN)

( * ) Notice: Subject to any disclaimer, the term of this patent is extended or adjusted under 35 U.S.C. 154(b) by 861 days.

(21) Appl. No.: 17/778,632

(22) PCT Filed: Nov. 20, 2020

(86) PCT No.: PCT/CN2020/130326

§ 371 (c)(1),
(2) Date: May 20, 2022

(87) PCT Pub. No.: WO2021/098811

PCT Pub. Date: May 27, 2021

(65) Prior Publication Data

US 2023/0018728 A1 Jan. 19, 2023

(30) Foreign Application Priority Data

Nov. 21, 2019 (CN) ......................... 201911147956.3
Aug. 19, 2020 (CN) ......................... 202010837381.4

(51) Int. Cl.

| | |
|---|---|
| ***A61K 31/5377*** | (2006.01) |
| ***C07D 413/00*** | (2006.01) |
| ***C07D 471/04*** | (2006.01) |
| ***C07D 487/04*** | (2006.01) |

(52) U.S. Cl.
CPC ......... *C07D 471/04* (2013.01); *C07D 487/04* (2013.01)

(58) Field of Classification Search
CPC .......................... A61K 31/5377; C07D 413/00
USPC ....................................... 514/234.5; 544/111
See application file for complete search history.

(56) References Cited

FOREIGN PATENT DOCUMENTS

| | | | |
|---|---|---|---|
| CN | 103068391 | A | 4/2013 |
| CN | 106795156 | A | 5/2017 |
| JP | 2014500277 | A | 1/2014 |
| JP | 2016516706 | A | 6/2016 |
| WO | 2010071837 | A1 | 6/2010 |
| WO | 2010073034 | A1 | 7/2010 |
| WO | 2011154737 | A1 | 12/2011 |
| WO | 2012078777 | A1 | 6/2012 |
| WO | 2014140644 | A1 | 9/2014 |
| WO | 2014159690 | A1 | 10/2014 |
| WO | 2016020320 | A1 | 2/2016 |
| WO | 2016130581 | A2 | 8/2016 |
| WO | 2017118734 | A1 | 7/2017 |
| WO | 2017121684 | A1 | 7/2017 |
| WO | 2018049400 | A1 | 3/2018 |
| WO | 2018153970 | A1 | 8/2018 |
| WO | 2019050889 | A1 | 3/2019 |
| WO | 2020049017 | A1 | 3/2020 |
| WO | 2020068729 | A1 | 4/2020 |

OTHER PUBLICATIONS

International Search Report and Written Opinion for International Patent Application No. PCT/CN2020/130326.

*Primary Examiner* — Douglas M Willis
(74) *Attorney, Agent, or Firm* — McCarter & English, LLP; Wei Song

(57) ABSTRACT

Disclosed is a pyrazolo-heteroaryl derivative, a preparation method therefor, and medical use thereof. In particular, the present invention relates to a pyrazolo-heteroaryl derivative as shown in the general formula (I), a preparation method therefor, a pharmaceutical composition containing the derivative, and a use thereof as a therapeutic agent, particularly as ATR kinase inhibitor and in the preparation of drugs for the treatment and/or prevention of hyperproliferative diseases. The definition of each group in the general formula (I) is identical as in the specification.

(I)

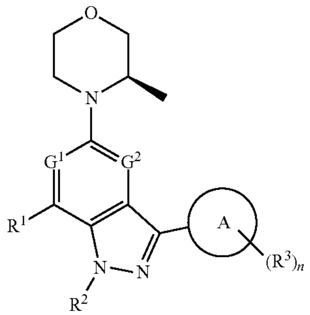

18 Claims, No Drawings

SUBSTITUTED MORPHOLINES AS ATR KINASE INHIBITORS

CROSS-REFERENCE TO RELATED APPLICATIONS

The present application is the national stage of International Patent Application No. PCT/CN2020/130326, filed on Nov. 20, 2020, which claims the benefit of and priority to Chinese Patent Application No. 201911147956.3, filed Nov. 21, 2019, and Chinese Patent Application No. 202010837381.4, filed on Aug. 19, 2020, all of which are incorporated herein by reference in their entirety.

TECHNICAL FIELD

The present disclosure relates to the field of pharmaceutics, and particularly to a pyrazolo-heteroaryl derivative of formula (I), a method for preparing the derivative, a pharmaceutical composition comprising the derivative, and use of the derivative as a therapeutic agent, specifically use as an ATR kinase inhibitor and use in preparing a medicament for treating and/or preventing hyperproliferative diseases.

BACKGROUND

Thousands of DNA damages occur every day in both normal and tumor cells. This makes DNA damage repair a crucial role in maintaining genomic stability and cell viability. Compared to normal cells, tumor cells are subject to greater replication stress. They carry more endogenous DNA damages, and often demonstrate loss of one or more DNA damage repair pathways. This makes the survival of tumor cells more dependent on the successful repair of DNA damages.

Homologous recombination repair is the prominent repair mode of DNA double-strand break, which takes the homologous sequence of undamaged sister chromatid as the template for repair to replicate the DNA sequence at the damaged part and precisely repair the DNA. This repair occurs primarily in the G2 and S phases. ATR, a member of the PIKK family, is a key enzyme in the homologous recombination repair pathway. When ATR/ATRIP complex binds to damaged DNA covered by replication protein A (RPA), ATR is activated and regulates checkpoints of the cell cycle by phosphorylating downstream proteins such as Chk1 and SMARCAL, causing cell cycle arrest. It also ensures the stability of damaged DNA and elevates dNTP concentration to promote DNA damage repair. DNA damage repair occurring during the S phase of the cell cycle is mainly accomplished by the ATR pathway, suggesting that ATR is very important to ensure cell proliferation. Analysis of clinical tumor samples indicated that elevated ATR expression levels were observed in a variety of tumor tissues, such as gastric cancer, liver cancer, colorectal cancer, ovarian cancer, and pancreatic cancer. Moreover, in patients with ovarian cancer and pancreatic cancer, higher levels of ATR is usually associated with lower survival rates. As such, ATR is an important target for tumor therapy.

Disclosed patent applications of ATR inhibitors include Patent Nos. WO2010071837, WO2011154737, WO2016020320, WO2016130581, WO2017121684, WO2017118734, WO2018049400, WO2019050889, WO2014140644, etc.

SUMMARY

The present disclosure is intended to provide a compound of formula (I) or a tautomer, mesomer, racemate, enantiomer, diastereomer thereof or a mixture thereof, or a pharmaceutically acceptable salt thereof, (I)

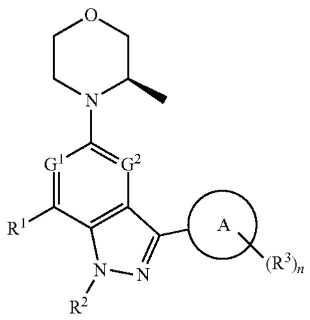

wherein:

$G^1$ and $G^2$ are identical or different and are each independently CH or N, provided that $G^1$ and $G^2$ are not both CH;

ring A is heteroaryl;

$R^1$ is selected from the group consisting of hydrogen, halogen, alkyl, alkenyl, alkoxy, haloalkyl, haloalkoxy, hydroxy, hydroxyalkyl, cyano, amino, $-NR^4R^5$, $-CONR^4R^5$, $-SO_2NR^4R^5$, $-R^6N-CO-NR^4R^5$, $-COOR^7$, $-SO_2R^7$, cycloalkyl, heterocyclyl, aryl and heteroaryl, wherein the alkyl, alkoxy, amino, cycloalkyl, heterocyclyl, aryl and heteroaryl are each independently optionally substituted with one or more substituents selected from the group consisting of halogen, alkyl, alkoxy, haloalkyl, hydroxy, hydroxyalkyl, cyano, amino, nitro, $-NR^4R^5$, $-CONR^4R^5$, $-SO_2NR^4R^5$, $-R^6N-CO-NR^4R^5$, $-COOR^7$, $-SO_2R^7$, cycloalkyl, heterocyclyl, aryl and heteroaryl;

$R^2$ is selected from the group consisting of hydrogen, halogen, alkyl, alkenyl, alkoxy, haloalkyl, haloalkoxy, hydroxy, hydroxyalkyl, cyano, amino, cycloalkyl, heterocyclyl, aryl and heteroaryl, wherein the alkyl, alkoxy, cycloalkyl, heterocyclyl, aryl and heteroaryl are each independently optionally substituted with one or more substituents selected from the group consisting of halogen, alkyl, alkoxy, haloalkyl, hydroxy, hydroxyalkyl, cyano, amino, nitro, cycloalkyl, heterocyclyl, aryl and heteroaryl;

$R^3$ is selected from the group consisting of hydrogen, halogen, alkyl, alkenyl, alkoxy, haloalkyl, haloalkoxy, hydroxy, hydroxyalkyl, cyano, amino, cycloalkyl, heterocyclyl, aryl and heteroaryl, wherein the alkyl, alkoxy, cycloalkyl, heterocyclyl, aryl and heteroaryl are each independently optionally substituted with one or more substituents selected from the group consisting of halogen, alkyl, alkoxy, haloalkyl, hydroxy, hydroxyalkyl, cyano, amino, nitro, cycloalkyl, heterocyclyl, aryl and heteroaryl;

$R^4$ and $R^5$ are identical or different and are each independently selected from the group consisting of hydrogen, alkyl, haloalkyl, hydroxy, amino, cycloalkyl, heterocyclyl, aryl and heteroaryl;

$R^6$ is selected from the group consisting of hydrogen, alkyl, haloalkyl, cycloalkyl, heterocyclyl, aryl and heteroaryl;

$R^7$ is selected from the group consisting of hydrogen, alkyl, haloalkyl, cycloalkyl, heterocyclyl, aryl and heteroaryl; and n is 0, 1, 2 or 3.

In some embodiments of the present disclosure, in the compound of formula (I) or the tautomer, mesomer, racemate, enantiomer or diastereomer thereof or the mixture thereof, or the pharmaceutically acceptable salt thereof, ring A is selected from the group consisting of pyrazolyl, pyrrolyl and imidazolyl.

In some preferred embodiments of the present disclosure, the compound of formula (I) or the tautomer, mesomer, racemate, enantiomer or diastereomer thereof or the mixture thereof, or the pharmaceutically acceptable salt thereof is a compound of formula (II) or a tautomer, mesomer, racemate, enantiomer or diastereomer thereof or a mixture thereof, or a pharmaceutically acceptable salt thereof, (II)

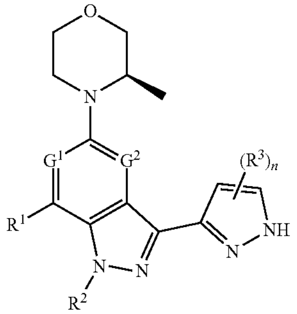

wherein:

$G^1$, $G^2$, $R^1$, $R^2$, $R^3$ and n are as defined in formula (I).

In some preferred embodiments of the present disclosure, the compound of formula (I) or the tautomer, mesomer, racemate, enantiomer or diastereomer thereof or the mixture thereof, or the pharmaceutically acceptable salt thereof is a compound of formula (III) or (IV) or a tautomer, mesomer, racemate, enantiomer or diastereomer thereof or a mixture thereof, or a pharmaceutically acceptable salt thereof, (III)

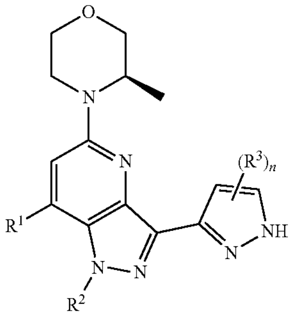

or (IV)

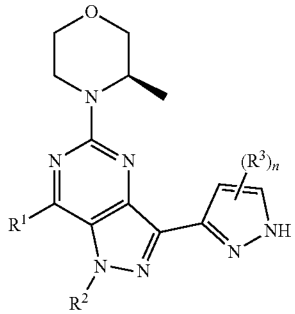

wherein: $R^1$, $R^2$, $R^3$ and n are as defined in formula (I).

In some embodiments of the present disclosure, in the compound of formula (I) or the tautomer, mesomer, racemate, enantiomer or diastereomer thereof or the mixture thereof, or the pharmaceutically acceptable salt thereof, $R^1$ is selected from the group consisting of alkyl, cycloalkyl, heterocyclyl, aryl and heteroaryl, wherein the alkyl, cycloalkyl, heterocyclyl, aryl and heteroaryl are each independently optionally substituted with one or more substituents selected from the group consisting of halogen, alkyl, alkoxy, haloalkyl, hydroxy, hydroxyalkyl, cyano, amino, nitro, cycloalkyl, heterocyclyl, aryl and heteroaryl.

In some embodiments of the present disclosure, in the compound of formula (I) or the tautomer, mesomer, racemate, enantiomer or diastereomer thereof or the mixture thereof, or the pharmaceutically acceptable salt thereof, $R^1$ is selected from the group consisting of alkyl, cycloalkyl or heterocyclyl, wherein the alkyl is optionally substituted with one or more substituents selected from the group consisting of halogen, alkyl, alkoxy, haloalkyl, hydroxyalkyl, cyano, amino, nitro, cycloalkyl, heterocyclyl, aryl and heteroaryl, and the cycloalkyl and heterocyclyl are each independently optionally substituted with one or more substituents selected from the group consisting of halogen, alkyl, alkoxy, haloalkyl, hydroxy, hydroxyalkyl, cyano, amino, nitro, cycloalkyl, heterocyclyl, aryl and heteroaryl; preferably, $R^1$ is $C_1$-$C_6$ alkyl or 3- to 6-membered cycloalkyl, wherein the $C_1$-$C_6$ alkyl and 3- to 6-membered cycloalkyl are each independently optionally substituted with one or more substituents selected from the group consisting of halogen, $C_1$-$C_6$ alkyl, $C_1$-$C_6$ alkoxy, $C_1$-$C_6$ haloalkyl, $C_1$-$C_6$ hydroxyalkyl, cyano, amino, nitro, 3- to 6-membered cycloalkyl, 3- to 6-membered heterocyclyl, 6- to 10-membered aryl and 5- to 10-membered heteroaryl; more preferably, $R^1$ is $C_1$-$C_6$ alkyl or 3- to 6-membered cycloalkyl, wherein the $C_1$-$C_6$ alkyl and 3- to 6-membered cycloalkyl are each independently optionally substituted with a cyano; and most preferably $R^1$ is

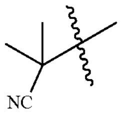

or

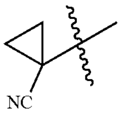

.

In some embodiments of the present disclosure, in the compound of formula (I) or the tautomer, mesomer, racemate, enantiomer or diastereomer thereof or the mixture thereof, or the pharmaceutically acceptable salt thereof, $R^2$ is hydrogen or alkyl, preferably alkyl and more preferably $C_{1-6}$ alkyl.

In some embodiments of the present disclosure, in the compound of formula (I) or the tautomer, mesomer, racemate, enantiomer or diastereomer thereof or the mixture thereof, or the pharmaceutically acceptable salt thereof, $R^2$ is alkyl.

In some embodiments of the present disclosure, in the compound of formula (I) or the tautomer, mesomer, racemate, enantiomer or diastereomer thereof or the mixture thereof, or the pharmaceutically acceptable salt thereof, $R^3$ is hydrogen.

Typical compounds disclosed herein include, but are not limited to:

| Example | Structure and name of compound |
|---|---|
| 1 | 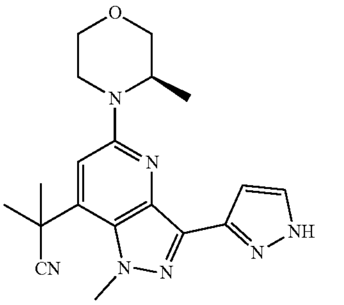<br>1<br>(R)-2-methyl-2-(1-methyl-5-(3-methylmorpholinyl)-3-(1H-pyrazol-3-yl)-1H-pyrazolo[4,3-b]pyridin-7-yl)propanenitrile 1 |
| 2 | 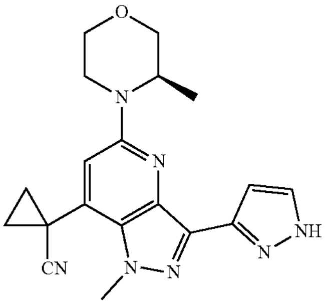<br>2<br>(R)-1-(1-methyl-5-(3-methylmorpholinyl)-3-(1H-pyrazol-3-yl)-1H-pyrazolo[4,3-b]pyridin-7-yl)cyclopropanenitrile 2 |
| 3 | 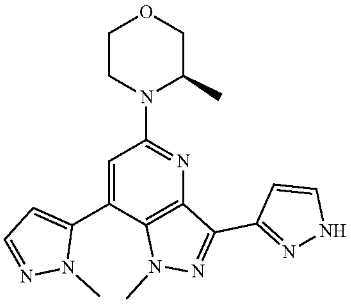<br>3<br>(R)-3-methyl-4-(1-methyl-7-(l-methyl-1H-pyrazol-5-yl)-3-(1H-pyrazol-3-yl)-1H-pyrazolo[4,3-b]pyridin-5-yl)morpholine 3 |

-continued

| Example | Structure and name of compound |
|---|---|
| 4 | 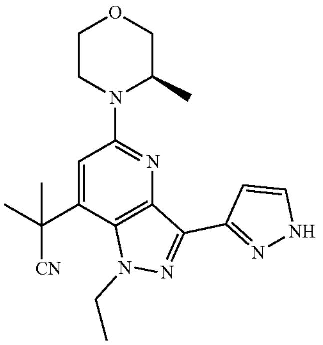<br>4<br>(R)-2-(l-ethyl-5-(3-methylmorpholinyl)-3-(1H-pyrazol-3-yl)-1H-pyrazolo[4,3-b]pyridin-7-yl)-2-methylpropanenitrile 4 |
| 5 | 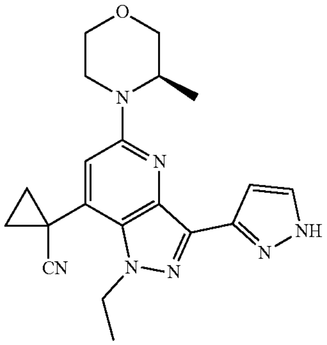<br>5<br>(R)-1-(l-ethyl-5-(3-methylmorpholinyl)-3-(1H-pyrazol-3-yl)-1H-pyrazolo[4,3-b]pyridin-7-yl)cyclopropanenitrile 5 |
| 6 | 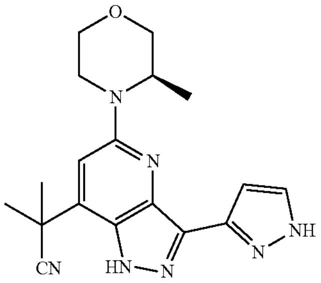<br>6<br>(R)-2-methyl-2-(5-(3-methylmorpholinyl)-3-(1H-pyrazol-3-yl)-1H-pyrazolo[4,3-b]pyridin-7-yl)propanenitrile 6 |

| Example | Structure and name of compound |
| --- | --- |
| | 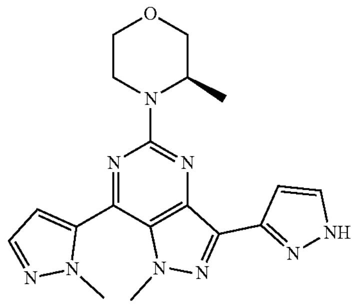 [SMILES: C[C@@H]1COCCN1c1nc(-c2ccnn2C)c2c(n1)c(-c1cc[nH]n1)nn2C] (R)-3-methyl-4-(1-methyl-7-(l-methyl-1H-pyrazol-5-yl)-3-(1H-pyrazol-3-yl)-1H-pyrazolo[4,3-b]pyrimidin-5-yl)morpholine |
| | 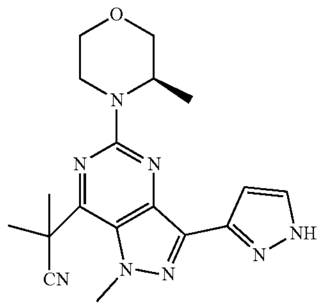 [SMILES: C[C@@H]1COCCN1c1nc(C(C)(C)C#N)c2c(n1)c(-c1cc[nH]n1)nn2C] (R)-2-methyl-2-(1-methyl-5-(3-methylmorpholinyl)-3-(1H-pyrazol-3-yl)-1H-pyrazolo[4,3-b]pyrimidin-7-yl)propanenitrile |
| | 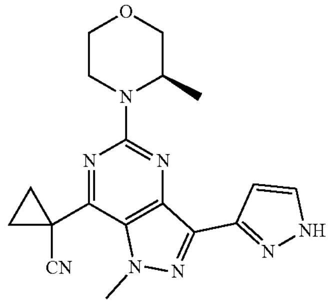 [SMILES: C[C@@H]1COCCN1c1nc(C2(C#N)CC2)c2c(n1)c(-c1cc[nH]n1)nn2C] (R)-1-(1-methyl-5-(3-methylmorpholinyl)-3-(1H-pyrazol-3-yl)-1H-pyrazolo[4,3-b]pyrimidin-7-yl)cyclopropanenitrile |

Another aspect of the present disclosure relates to a compound of formula (IA) or a tautomer, mesomer, racemate, enantiomer or diastereomer thereof or a mixture thereof, or a pharmaceutically acceptable salt thereof, (IA)

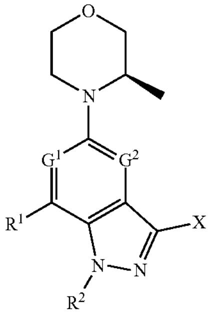

wherein:

X is halogen, preferably Br;

$G^1$ and $G^2$ are identical or different and are each independently CH or N, provided that $G^1$ and $G^2$ are not both CH;

$R^1$ is selected from the group consisting of hydrogen, halogen, alkyl, alkenyl, alkoxy, haloalkyl, haloalkoxy, hydroxy, hydroxyalkyl, cyano, amino, $-NR^4R^5$, $-CONR^4R^5$, $-SO_2NR^4R^5$, $-R^6N-CO-NR^4R^5$, $-COOR^7$, $-SO_2R^7$, cycloalkyl, heterocyclyl, aryl and heteroaryl, wherein the alkyl, alkoxy, amino, cycloalkyl, heterocyclyl, aryl and heteroaryl are each independently optionally substituted with one or more substituents selected from the group consisting of halogen, alkyl, alkoxy, haloalkyl, hydroxy, hydroxyalkyl, cyano, amino, nitro, $-NR^4R^5$, $-CONR^4R^5$, $-SO_2NR^4R^5$, $-R^6N-CO-NR^4R^5$, $-COOR^7$, $-SO_2R^7$, cycloalkyl, heterocyclyl, aryl and heteroaryl;

$R^2$ is selected from the group consisting of hydrogen, halogen, alkyl, alkenyl, alkoxy, haloalkyl, haloalkoxy, hydroxy, hydroxyalkyl, cyano, amino, cycloalkyl, heterocyclyl, aryl and heteroaryl, wherein the alkyl, alkoxy, cycloalkyl, heterocyclyl, aryl and heteroaryl are each independently optionally substituted with one or more substituents selected from the group consisting of halogen, alkyl, alkoxy, haloalkyl, hydroxy, hydroxyalkyl, cyano, amino, nitro, cycloalkyl, heterocyclyl, aryl and heteroaryl;

$R^4$ and $R^5$ are identical or different and are each independently selected from the group consisting of hydrogen, alkyl, haloalkyl, hydroxy, amino, cycloalkyl, heterocyclyl, aryl and heteroaryl;

$R^6$ is selected from the group consisting of hydrogen, alkyl, haloalkyl, cycloalkyl, heterocyclyl, aryl and heteroaryl; and $R^7$ is selected from the group consisting of hydrogen, alkyl, haloalkyl, cycloalkyl, heterocyclyl, aryl and heteroaryl.

Another aspect of the present disclosure relates to a compound of formula (IIIC) or a tautomer, mesomer, racemate, enantiomer or diastereomer thereof or a mixture thereof, or a pharmaceutically acceptable salt thereof, (IIIC)

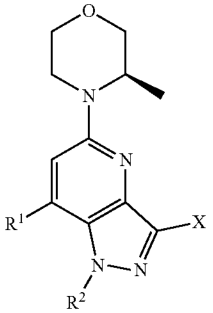

wherein: X, $R^1$ and $R^2$ are as defined in formula (IA).

Another aspect of the present disclosure relates to a compound of formula (IIA) or a tautomer, mesomer, racemate, enantiomer or diastereomer thereof or a mixture thereof, or a pharmaceutically acceptable salt thereof, (IIA)

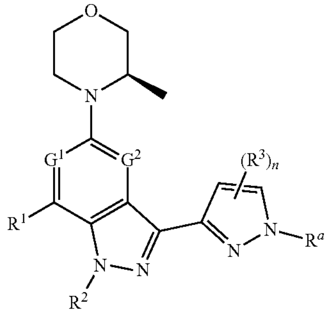

wherein:

$R^a$ is an amino protecting group;

$G^1$ and $G^2$ are identical or different and are each independently CH or N, provided that $G^1$ and $G^2$ are not both CH;

$R^1$ is selected from the group consisting of hydrogen, halogen, alkyl, alkenyl, alkoxy, haloalkyl, haloalkoxy, hydroxy, hydroxyalkyl, cyano, amino, $—NR^4R^5$, $—CONR^4R^5$, $—SO_2NR^4R^5$, $—R^6N—CO—NR^4R^5$, $—COOR^7$,$—SO_2R^7$, cycloalkyl, heterocyclyl, aryl and heteroaryl, wherein the alkyl, alkoxy, amino, cycloalkyl, heterocyclyl, aryl and heteroaryl are each independently optionally substituted with one or more substituents selected from the group consisting of halogen, alkyl, alkoxy, haloalkyl, hydroxy, hydroxyalkyl, cyano, amino, nitro, $—NR^4R^5$, $—CONR^4R^5$, $—SO_2NR^4R^5$, $—R^6N—CO—NR^4R^5$, $—COOR^7$,$—SO_2R^7$, cycloalkyl, heterocyclyl, aryl and heteroaryl;

$R^2$ is selected from the group consisting of hydrogen, halogen, alkyl, alkenyl, alkoxy, haloalkyl, haloalkoxy, hydroxy, hydroxyalkyl, cyano, amino, cycloalkyl, heterocyclyl, aryl and heteroaryl, wherein the alkyl, alkoxy, cycloalkyl, heterocyclyl, aryl and heteroaryl are each independently optionally substituted with one or more substituents selected from the group consisting of halogen, alkyl, alkoxy, haloalkyl, hydroxy, hydroxyalkyl, cyano, amino, nitro, cycloalkyl, heterocyclyl, aryl and heteroaryl;

$R^3$ is selected from the group consisting of hydrogen, halogen, alkyl, alkenyl, alkoxy, haloalkyl, haloalkoxy, hydroxy, hydroxyalkyl, cyano, amino, cycloalkyl, heterocyclyl, aryl and heteroaryl, wherein the alkyl, alkoxy, cycloalkyl, heterocyclyl, aryl and heteroaryl are each independently optionally substituted with one or more substituents selected from the group consisting of halogen, alkyl, alkoxy, haloalkyl, hydroxy, hydroxyalkyl, cyano, amino, nitro, cycloalkyl, heterocyclyl, aryl and heteroaryl;

$R^4$ and $R^5$ are identical or different and are each independently selected from the group consisting of hydrogen, alkyl, haloalkyl, hydroxy, amino, cycloalkyl, heterocyclyl, aryl and heteroaryl;

$R^6$ is selected from the group consisting of hydrogen, alkyl, haloalkyl, cycloalkyl, heterocyclyl, aryl and heteroaryl;

$R^7$ is selected from the group consisting of hydrogen, alkyl, haloalkyl, cycloalkyl, heterocyclyl, aryl and heteroaryl; and n is 0, 1, 2 or 3.

Another aspect of the present disclosure relates to a compound of formula (IIGA) or a tautomer, mesomer, racemate, enantiomer or diastereomer thereof or a mixture thereof, or a pharmaceutically acceptable salt thereof, (IIGA)

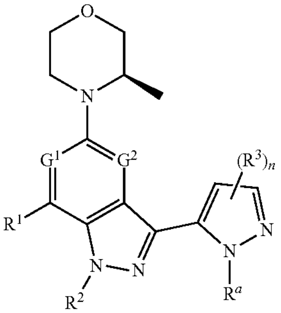

wherein: $G^1$, $G^2$, $R^1$, $R^2$, $R^3$, $R^a$ and n are as defined in formula (IIA).

Another aspect of the present disclosure relates to a compound of formula (IIIA) or a tautomer, mesomer, racemate, enantiomer or diastereomer thereof or a mixture thereof, or a pharmaceutically acceptable salt thereof, (IIIA)

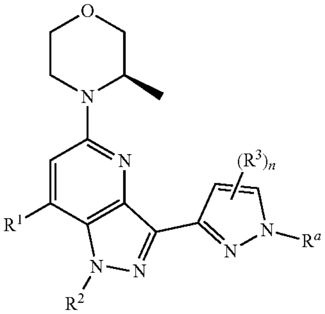

wherein: $R^a$, $R^1$, $R^2$, $R^3$ and n are as defined in formula (IIA).

Another aspect of the present disclosure relates to a compound of formula (IIIGA) or a tautomer, mesomer, racemate, enantiomer or diastereomer thereof or a mixture thereof, or a pharmaceutically acceptable salt thereof, (IIIGA)

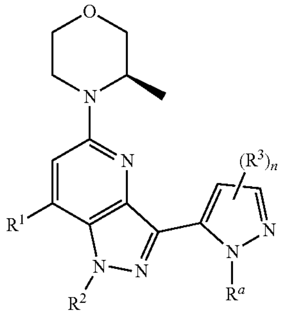

wherein: $R^a$, $R^1$, $R^2$, $R^3$ and n are as defined in formula (IIIA).

Typical intermediate compounds described herein include, but are not limited to:

| Example | Structure and name of compound |
| --- | --- |
| 1i | 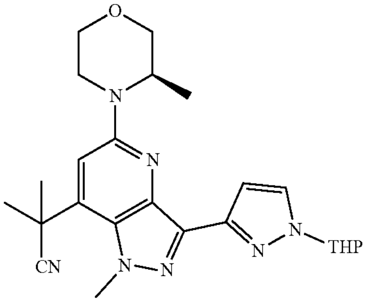<br>1i<br>2-methyl-2-(1-methyl-5-((R)-3-methylmorpholinyl)-3-(1-(tetrahydro-2H-pyran-2-yl)-1H-pyrazol-3-yl)-1H-pyrazolo[4,3-b]pyridin-7-yl)propanenitrile 1i |
| 2c | 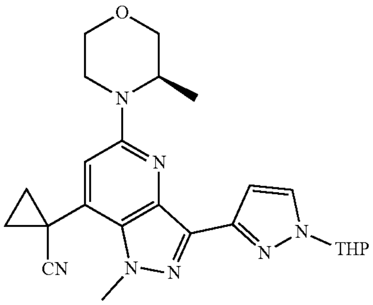<br>2c<br>1-(1-methyl-5-((R)-3-methylmorpholinyl)-3-(1-(tetrahydro-2H-pyran-2-yl)-1H-pyrazol-3-yl)-1H-pyrazolo[4,3-b]pyridin-7-yl) cyclopropanenitrile 2c |

-continued

| Example | Structure and name of compound |
| --- | --- |
| 3c | 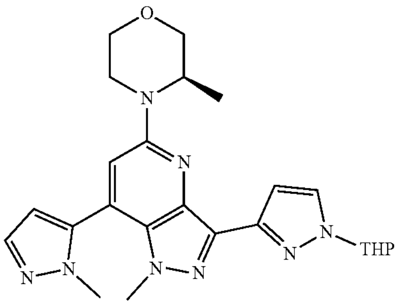<br>3c<br>(3R)-3-methyl-4-(1-methyl-7-(l-methyl-1H-pyrazol-5-yl)-3-(1-(tetrahydro-2H-pyran-2-yl)-1H-pyrazol-3-yl)-1H-pyrazolo[4,3-b]pyridin-5-yl)morpholine 3c |
| 4i | 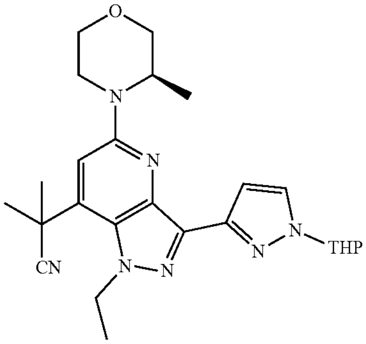<br>4i<br>2-(1-ethyl-5-((R)-3-methylmorpholinyl)-3-(1-(tetrahydro-2H-pyran-2-yl)-1H-pyrazol-3-yl)-1H-pyrazolo[4,3-b]pyridin-7-yl)-2-methylpropanenitrile 4i |
| 6j | 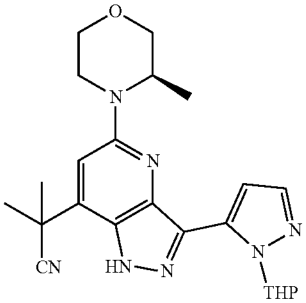<br>6j<br>2-methyl-2-(5-((R)-3-methylmorpholinyl)-3-(1-(tetrahydro-2H-pyran-2-yl)-1H-pyrazol-5-yl)-1H-pyrazolo[4,3-b]pyridin-7-yl)propanenitrile 6j |

-continued

| Example | Structure and name of compound |
| --- | --- |
| 1h | 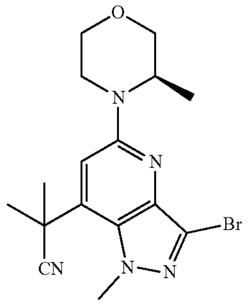 1h (R)-2-(3-bromo-1-methyl-5-(3-methylmorpholinyl)-1H-pyrazolo[4,3-b]pyridin-7-yl)-2-methylpropanenitrile 1h |
| 2b | 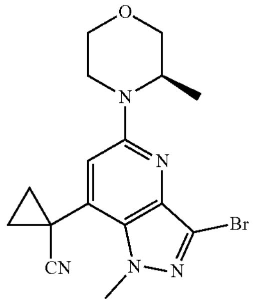 2b (R)-1-(3-bromo-1-methyl-5-(3-methylmorpholinyl)-1H-pyrazolo[4,3-b]pyridin-7-yl)cyclopropanenitrile 2b |
| 3b | 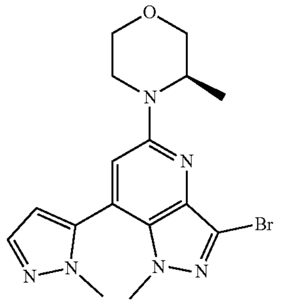 3b (R)-4-(3-bromo-1-methyl-7-(1-methyl-1H-pyrazol-5-yl)-1H-pyrazolo[4,3-b]pyridin-5-yl)-3-methylmorpholine 3b |

-continued

| Example | Structure and name of compound |
| --- | --- |
| 4h | 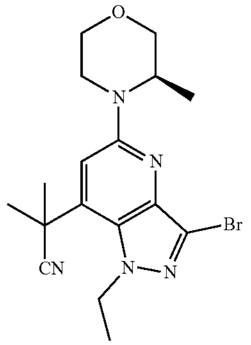 4h (R)-2-(3-bromo-1-ethyl-5-(3-methylmorpholinyl)-1H-pyrazolo[4,3-b]pyridin-7-yl)-2-methylpropanenitrile 4h |
| 5b | 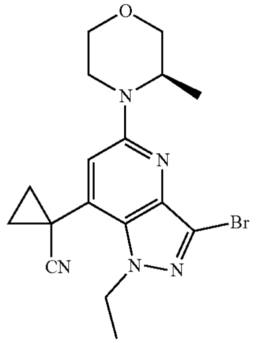 5b (R)-1-(3-bromo-1-ethyl-5-(3-methylmorpholinyl)-1H-pyrazolo[4,3-b]pyridin-7-yl)cyclopropanenitrile 5b |
| 6h | 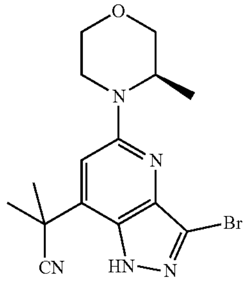 6h (R)-2-(3-bromo-5-(3-methylmorpholinyl)-1H-pyrazolo[4,3-b]pyridin-7-yl)-2-methylpropanenitrile 6h |

Another aspect of the present disclosure relates to a method for preparing a compound of formula (I) or a tautomer, mesomer, racemate, enantiomer or diastereomer thereof or a mixture thereof, or a pharmaceutically acceptable salt thereof, comprising:

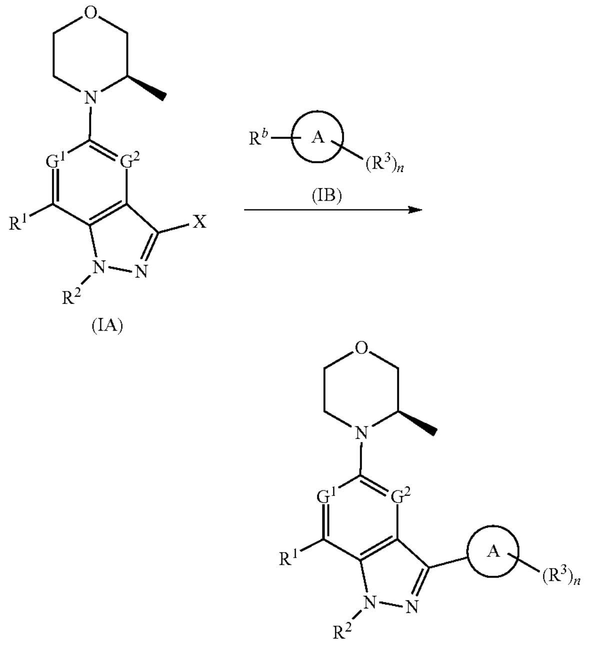

(IA)

(IB)

(I)

subjecting a compound of formula (IA) and a compound of formula (IB) to a coupling reaction to obtain the compound of formula (I), wherein:

X is halogen, preferably Br;

$R^b$ is

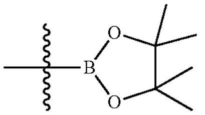

or

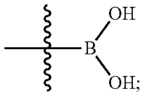

and ring A, $G^1$, $G^2$, $R^1$, $R^2$, $R^3$ and n are as defined in formula (I).

Another aspect of the present disclosure relates to a method for preparing a compound of formula (II) or a tautomer, mesomer, racemate, enantiomer or diastereomer thereof or a mixture thereof, or a pharmaceutically acceptable salt thereof, comprising:

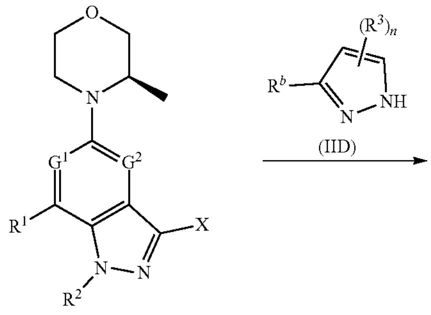

(IA)

(IID)

-continued

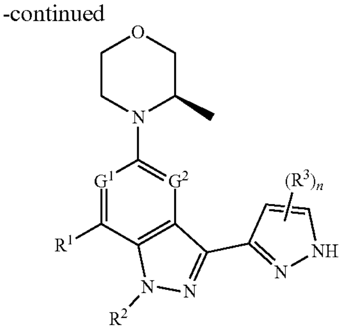

(II)

subjecting a compound of formula (IA) and a compound of formula (IID) to a coupling reaction to obtain the compound of formula (II), wherein:

X is halogen, preferably Br;

$R^b$ is

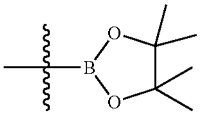

or

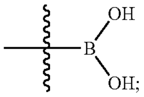

and $G^1$, $G^2$, $R^1$, $R^2$, $R^3$ and n are as defined in formula (II).

Another aspect of the present disclosure relates to a method for preparing a compound of formula (III) or a tautomer, mesomer, racemate, enantiomer or diastereomer thereof or a mixture thereof, or a pharmaceutically acceptable salt thereof, comprising:

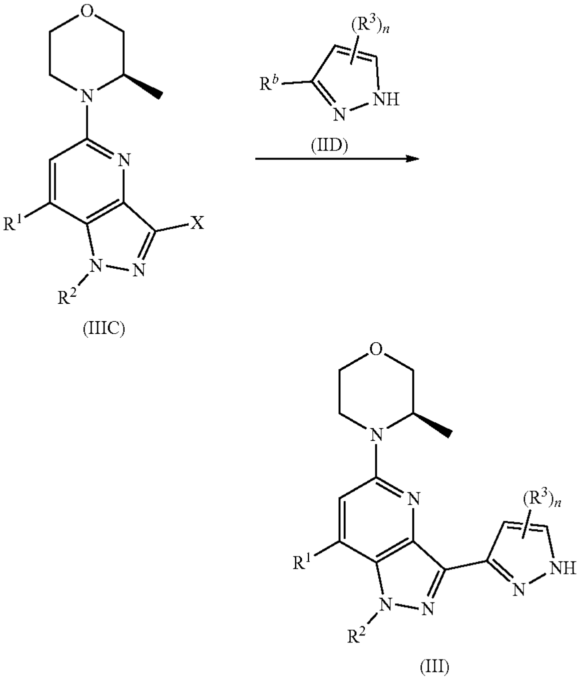

(IIIC)

(IID)

(III)

subjecting a compound of formula (IIIC) and a compound of formula (IID) to a coupling reaction to obtain the compound of formula (III), wherein:

X is halogen, preferably Br;

$R^b$ is

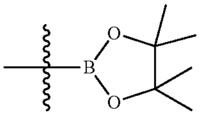

or

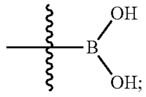

and $R^1$, $R^2$, $R^3$ and n are as defined in formula (III).

Another aspect of the present disclosure relates to a method for preparing a compound of formula (IV) or a tautomer, mesomer, racemate, enantiomer or diastereomer thereof or a mixture thereof, or a pharmaceutically acceptable salt thereof, comprising:

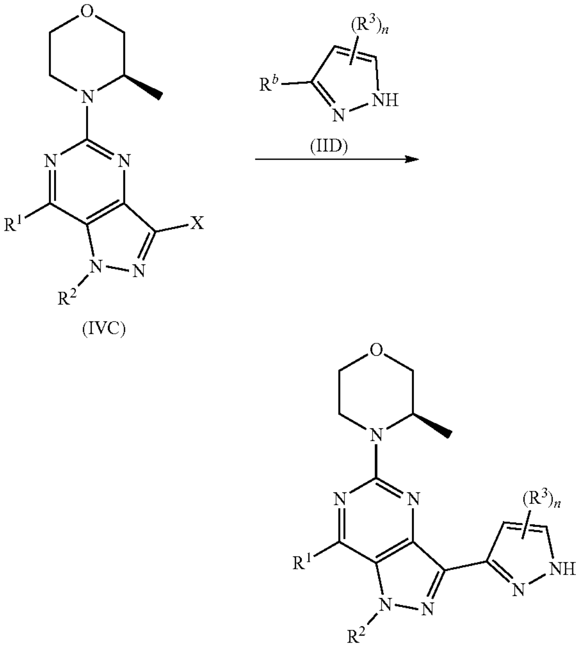

(IVC) (IID) (IV)

subjecting a compound of formula (IVC) and a compound of formula (IID) to a coupling reaction to obtain the compound of formula (IV), wherein:

X is halogen, preferably Br;

$R^b$ is

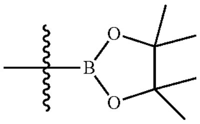

or

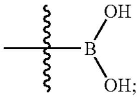

and $R^1$, $R^2$, $R^3$ and n are as defined in formula (IV).

Another aspect of the present disclosure relates to a method for preparing a compound of formula (IIA) or a tautomer, mesomer, racemate, enantiomer or diastereomer thereof or a mixture thereof, or a pharmaceutically acceptable salt thereof, comprising:

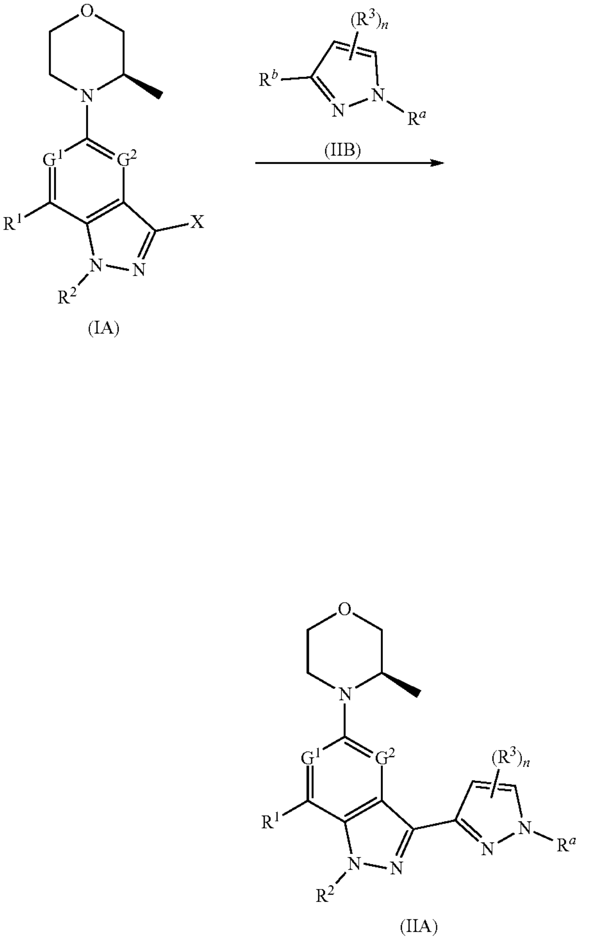

(IA) (IIB) (IIA)

subjecting a compound of formula (IA) and a compound of formula (IIB) to a coupling reaction to obtain the compound of formula (IIA), wherein:

X is halogen, preferably Br;

$R^a$ is an amino protecting group;

$R^b$ is

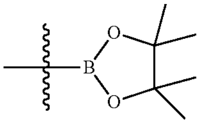

or

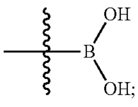

and $G^1$, $G^2$, $R^1$, $R^2$, $R^3$ and n are as defined in formula (II).

Another aspect of the present disclosure relates to a method for preparing a compound of formula (II) or a tautomer, mesomer, racemate, enantiomer or diastereomer thereof or a mixture thereof, or a pharmaceutically acceptable salt thereof, comprising:

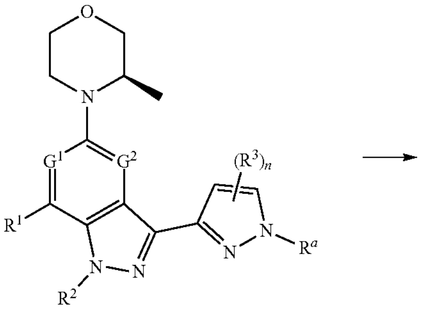

(IIA)

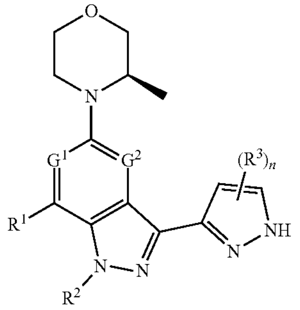

(II)

removing an amino protecting group from a compound of formula (IIA) to obtain the compound of formula (II), wherein:

$R^a$ is the amino protecting group; and $G^1$, $G^2$, $R^1$, $R^2$, $R^3$ and n are as defined in formula (II).

Another aspect of the present disclosure relates to a method for preparing a compound of formula (IIGA) or a tautomer, mesomer, racemate, enantiomer or diastereomer thereof or a mixture thereof, or a pharmaceutically acceptable salt thereof, comprising:

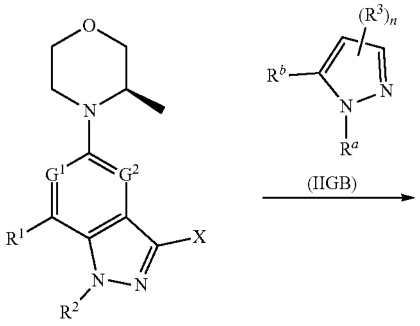

(IIGB)

(IA)

-continued

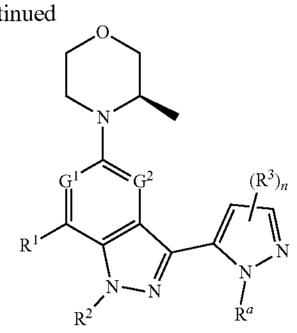

(IIGA)

subjecting a compound of formula (IA) and a compound of formula (IIGB) to a coupling reaction to obtain the compound of formula (IIGA), wherein:

X is halogen, preferably Br;

$R^a$ is an amino protecting group;

$R^b$ is

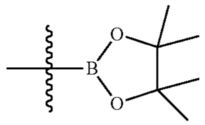

or

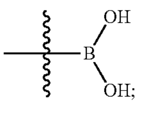

and $G^1$, $G^2$, $R^1$, $R^2$, $R^3$ and n are as defined in formula (IIGA).

Another aspect of the present disclosure relates to a method for preparing a compound of formula (II) or a tautomer, mesomer, racemate, enantiomer or diastereomer thereof or a mixture thereof, or a pharmaceutically acceptable salt thereof, comprising:

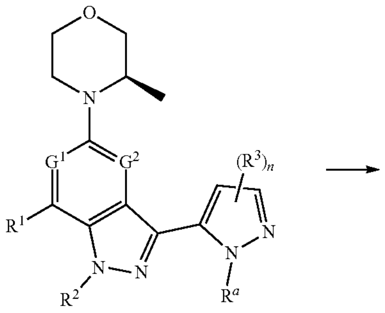

(IIGA)

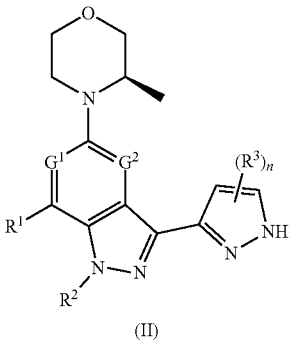

(II)

removing an amino protecting group from a compound of formula (IIGA) to obtain the compound of formula (II), wherein:

$R^a$ is the amino protecting group; and $G^1$, $G^2$, $R^1$, $R^2$, $R^3$ and n are as defined in formula (II).

Another aspect of the present disclosure relates to a method for preparing a compound of formula (IIIA) or a tautomer, mesomer, racemate, enantiomer or diastereomer thereof or a mixture thereof, or a pharmaceutically acceptable salt thereof, comprising:

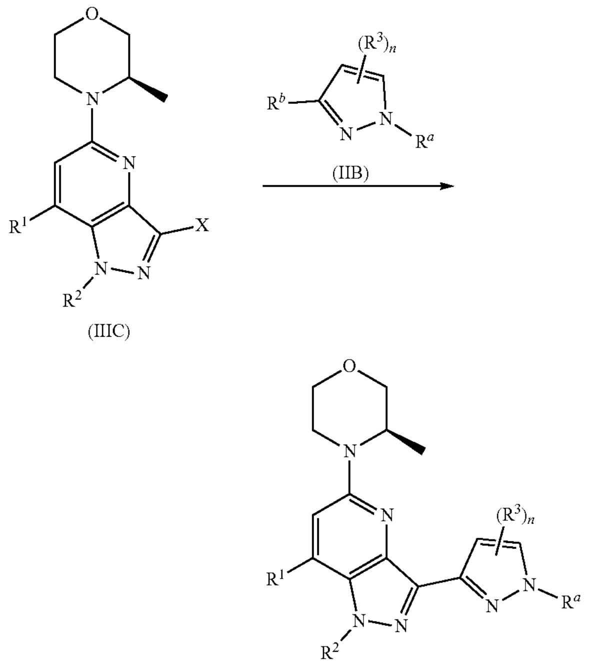

(IIIC) (IIB) (IIIA)

subjecting a compound of formula (IIIC) and a compound of formula (IIB) to a coupling reaction to obtain the compound of formula (IIIA), wherein:

X is halogen, preferably Br;

$R^a$ is an amino protecting group;

$R^b$ is

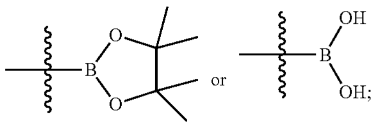

and $R^1$, $R^2$, $R^3$ and n are as defined in formula (III).

Another aspect of the present disclosure relates to a method for preparing a compound of formula (III) or a tautomer, mesomer, racemate, enantiomer or diastereomer thereof or a mixture thereof, or a pharmaceutically acceptable salt thereof, comprising:

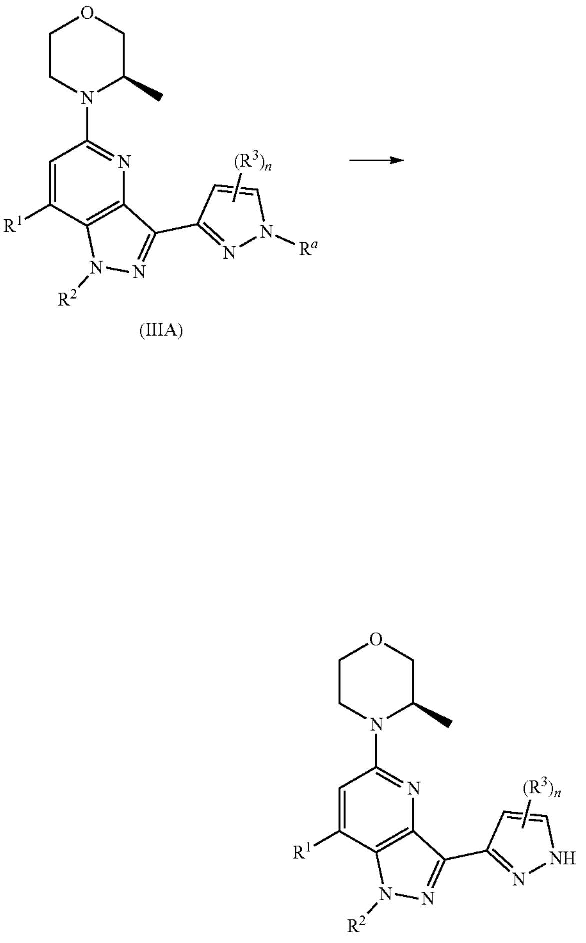

(IIIA) (III)

removing an amino protecting group from a compound of formula (IIIA) to obtain the compound of formula (III), wherein:

$R^a$ is the amino protecting group; and $R^1$, $R^2$, $R^3$ and n are as defined in formula (III).

Another aspect of the present disclosure relates to a method for preparing a compound of formula (IIIGA) or a tautomer, mesomer, racemate, enantiomer or diastereomer thereof or a mixture thereof, or a pharmaceutically acceptable salt thereof, comprising:

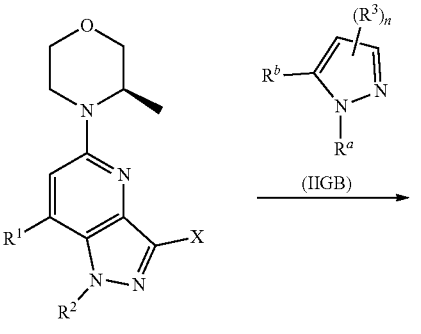

(IIIC) (IIGB)

-continued

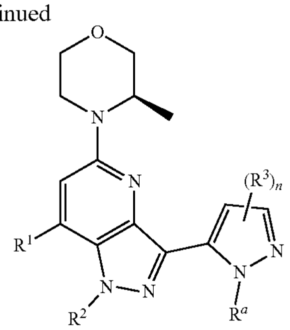

(IIIGA)

subjecting a compound of formula (IIIC) and a compound of formula (IIGB) to a coupling reaction to obtain the compound of formula (IIIGA), wherein:

X is halogen, preferably Br;

$R^a$ is an amino protecting group;

$R^b$ is

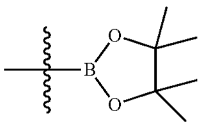 or 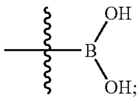

and $R^1$, $R^2$, $R^3$ and n are as defined in formula (IIIG).

Another aspect of the present disclosure relates to a method for preparing a compound of formula (III) or a tautomer, mesomer, racemate, enantiomer or diastereomer thereof or a mixture thereof, or a pharmaceutically acceptable salt thereof, comprising:

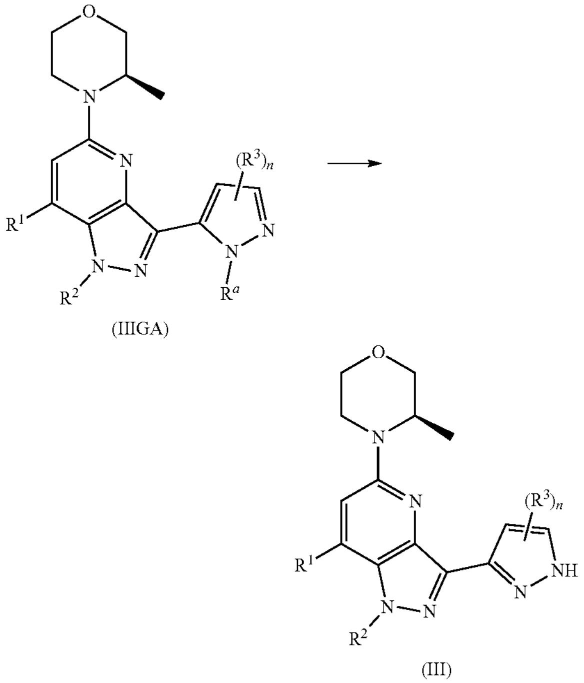

(IIIGA)

(III)

removing an amino protecting group from a compound of formula (IIIGA) to obtain the compound of formula (III), wherein:

$R^a$ is the amino protecting group; and $R^1$, $R^2$, $R^3$ and n are as defined in formula (III).

Another aspect of the present disclosure relates to a method for preparing a compound of formula (IV) or a tautomer, mesomer, racemate, enantiomer or diastereomer thereof or a mixture thereof, or a pharmaceutically acceptable salt thereof, comprising:

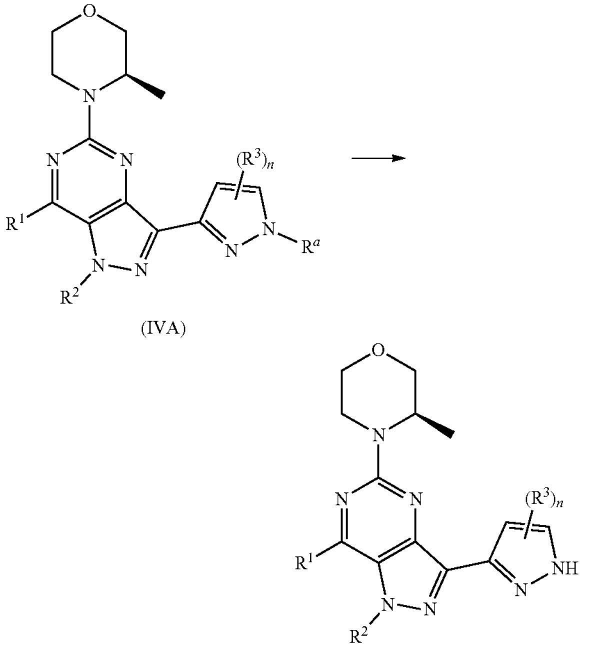

(IVA)

(IV)

removing an amino protecting group from a compound of formula (IVA) to obtain the compound of formula (IV), wherein:

$R^a$ is the amino protecting group; and $R^1$, $R^2$, $R^3$ and n are as defined in formula (IV).

Another aspect of the present disclosure relates to a pharmaceutical composition comprising the compound of formula (I) or the tautomer, mesomer, racemate, enantiomer or diastereomer thereof or the mixture thereof, or the pharmaceutically acceptable salt thereof disclosed herein, and one or more pharmaceutically acceptable carrier, diluent or excipient.

The present disclosure further relates to use of the compound of formula (I) or the tautomer, mesomer, racemate, enantiomer or diastereomer thereof or the mixture thereof, or the pharmaceutically acceptable salt thereof disclosed herein, or the pharmaceutical composition comprising the same in preparing a medicament for inhibiting ATR kinase.

The present disclosure further relates to use of the compound of formula (I) or the tautomer, mesomer, racemate, enantiomer or diastereomer thereof or the mixture thereof, or the pharmaceutically acceptable salt thereof disclosed herein, or the pharmaceutical composition comprising the same in preparing a medicament for treating and/or preventing a hyperproliferative disease.

The present disclosure further relates to use of the compound of formula (I) or the tautomer, mesomer, racemate, enantiomer or diastereomer thereof or the mixture thereof, or the pharmaceutically acceptable salt thereof disclosed herein, or the pharmaceutical composition comprising the same in preparing a medicament for treating and/or preventing a tumor.

The present disclosure further relates to use of the compound of formula (I) or the tautomer, mesomer, racemate, enantiomer or diastereomer thereof or the mixture thereof, or the pharmaceutically acceptable salt thereof disclosed herein, or the pharmaceutical composition comprising the same in preparing a medicament for treating a tumor.

The present disclosure further relates to a method for inhibiting ATR kinase, comprising: administering to a patient in need an effective amount of the compound of formula (I) or the tautomer, mesomer, racemate, enantiomer or diastereomer or the mixture thereof, or the pharmaceutically acceptable salt thereof, or the pharmaceutical composition comprising the same.

The present disclosure further relates to a method for treating and/or preventing a hyperproliferative disease, comprising: administering to a patient in need an effective amount of the compound of formula (I) or the tautomer, mesomer, racemate, enantiomer or diastereomer or the mixture thereof, or the pharmaceutically acceptable salt thereof, or the pharmaceutical composition comprising the same.

The present disclosure further relates to a method for treating and/or preventing a tumor, comprising: administering to a patient in need an effective amount of the compound of formula (I) or the tautomer, mesomer, racemate, enantiomer or diastereomer or the mixture thereof, or the pharmaceutically acceptable salt thereof, or the pharmaceutical composition comprising the same.

The present disclosure further relates to the compound of formula (I) or the tautomer, mesomer, racemate, enantiomer or diastereomer thereof or the mixture thereof, or the pharmaceutically acceptable salt thereof disclosed herein, or the pharmaceutical composition comprising the same for use as a medicament. The medicament can be used for treating and/or preventing a hyperproliferative disease, in particular a tumor.

The present disclosure further relates to the compound of formula (I) or the tautomer, mesomer, racemate, enantiomer or diastereomer thereof or the mixture thereof, or the pharmaceutically acceptable salt thereof disclosed herein, or the pharmaceutical composition comprising the same for use as an ATR kinase inhibitor.

The present disclosure further relates to the compound of formula (I) or the tautomer, mesomer, racemate, enantiomer or diastereomer thereof or the mixture thereof, or the pharmaceutically acceptable salt thereof disclosed herein, or the pharmaceutical composition comprising the same for use in treating and/or preventing a hyperproliferative disease.

The present disclosure further relates to the compound of formula (I) or the tautomer, mesomer, racemate, enantiomer or diastereomer thereof or the mixture thereof, or the pharmaceutically acceptable salt thereof disclosed herein, or the pharmaceutical composition comprising the same for use in treating a tumor.

The tumor described herein is selected from the group consisting of melanoma, brain tumor, esophageal cancer, gastric cancer, liver cancer, pancreatic cancer, colorectal cancer, lung cancer, kidney cancer, breast cancer, cervical cancer, ovarian cancer, prostate cancer, skin cancer, neuroblastoma, neuroglioma, sarcoma, bone cancer, uterine cancer, endometrial cancer, head and neck tumor, multiple myeloma, B-cell lymphoma, polycythemia vera, leukemia, thyroid tumor, bladder cancer and gallbladder cancer.

The active compound may be formulated into a form suitable for administration by any suitable route, preferably in a form of a unit dose, or in a form of a single dose that can be self-administered by a patient. The unit dose of the compound or composition disclosed herein may be in a tablet, a capsule, a cachet, a vial, a powder, a granule, a lozenge, a suppository, a powder for reconstitution or a liquid formulation.

The dosage of the compound or composition used in the treatment method disclosed herein will generally vary with the severity of the disease, the weight of the patient, and the relative efficacy of the compound. However, as a general guide, a suitable unit dose may be 0.1 to 1000 mg.

The pharmaceutical composition disclosed herein may comprise, in addition to the active compound, one or more excipients selected from the group consisting of: a filler (diluent), binder, wetting agent, disintegrant, excipient, and the like. Depending on the method of administration, the compositions may comprise 0.1 to 99 wt. % of active compound.

The pharmaceutical compositions comprising the active ingredient may be in a form suitable for oral administration, for example, a tablet, a dragee, a lozenge, an aqueous or oil suspension, a dispersible powder or granule, an emulsion, a hard or soft capsule, or a syrup or elixir. Oral compositions can be prepared according to any method known in the art for preparing pharmaceutical compositions and may comprise one or more ingredients selected from the group consisting of a sweetener, a corrigent, a colorant and a preservative, so as to provide a pleasant-to-eye and palatable pharmaceutical formulation. A tablet comprises an active ingredient and a non-toxic pharmaceutically acceptable excipient which is used for mixing and is suitable for the preparation of the tablet. Such an excipient may be an inert excipient, a granulating agent, a disintegrating agent, a binder and a lubricant. Such a tablet may be uncoated or may be coated by known techniques for masking the taste of the drug or delaying the disintegration and absorption of the drug in the gastrointestinal tract and thus enabling sustained release of the drug over a longer period.

An oral formulation in a soft gelatin capsule where the active ingredient is mixed with an inert solid diluent or with a water-soluble carrier or oil vehicle may also be provided.

An aqueous suspension comprises an active substance and an excipient which is used for mixing and suitable for the preparation of the aqueous suspension. Such an excipient is a suspending agent, a dispersant or a wetting agent. The aqueous suspension may also comprise one or more preservatives, one or more colorants, one or more corrigents and one or more sweeteners.

An oil suspension may be formulated by suspending the active ingredient in a vegetable oil, or in a mineral oil. The oil suspension may comprise a thickening agent. The sweeteners and corrigents described above may be added to provide a palatable formulation. Antioxidants can also be added to preserve the compositions.

Dispersible powders and granules suitable for the preparation of an aqueous suspension can be allowed to provide an active ingredient, and a dispersant or a wetting agent, a suspending agent or one or more preservatives for mixing, by adding water. The description above can be exemplified by suitable dispersants or wetting agents and suspending agents. Other excipients, such as sweeteners, corrigents and colorants, may also be added. Antioxidants such as ascorbic acid are added to preserve these compositions.

The pharmaceutical composition disclosed herein may also be in the form of an oil-in-water emulsion. The oil phase may be a vegetable oil or a mineral oil, or a mixture thereof. Suitable emulsifiers may be naturally occurring phospholipids, and the emulsion may also comprise a sweetener, a corrigent, a preservative and an antioxidant. Such a formulation may also comprise a palliative, a preservative, a colorant and an antioxidant.

The pharmaceutical composition disclosed herein may be in the form of a sterile injectable aqueous solution. Available and acceptable vehicles or solvents include water, Ringer's solution and isotonic sodium chloride solution. A sterile injectable formulation may be a sterile injectable oil-in-water microemulsion in which an active ingredient is dissolved in an oil phase. The injection or microemulsion can be locally injected into the bloodstream of a patient in large quantities. Alternatively, it may be desirable to administer solutions and microemulsions in such a way as to maintain a constant circulating concentration of the compound disclosed herein. To maintain such a constant concentration, a continuous intravenous delivery device may be used. An example of such a device is a Deltec CADD-PLUS™ 5400 intravenous injection pump.

The pharmaceutical composition disclosed herein may be in the form of a sterile injectable aqueous or oil suspension for intramuscular and subcutaneous administration. The suspension can be prepared according to the prior art using those suitable dispersants or wetting agents and suspending agents mentioned above. The sterile injectable formulation may also be a sterile injection or suspension prepared in a parenterally acceptable non-toxic diluent or solvent. In addition, a sterile fixed oil may be conventionally used as a solvent or a suspending medium. For this purpose, any blend fixed oil may be employed. In addition, fatty acids can also be used to prepare injections.

The compound disclosed herein may be administered in the form of a suppository for rectal administration. Such a pharmaceutical composition can be prepared by mixing a drug with a suitable non-irritating excipient which is a solid at an ambient temperature but a liquid in the rectum and therefore will melt in the rectum to release the drug.

As is well known to those skilled in the art, the dosage of the drug administered depends on a variety of factors, including but not limited to, the activity of the particular compound employed, the age of the patient, the weight of the patient, the health condition of the patient, the behavior of the patient, the diet of the patient, the time of administration, the route of administration, the rate of excretion, the combination of drugs, and the like. In addition, the optimal treatment regimen, such as the mode of administration, the daily dose of the compound of formula (I) or the type of pharmaceutically acceptable salts, can be verified according to conventional treatment regimens.

DETAILED DESCRIPTION OF THE INVENTION

Unless otherwise stated, the terms used in the specification and claims have the following meanings.

The term "alkyl" refers to a saturated aliphatic hydrocarbon group which is a linear or branched group containing 1 to 20 carbon atoms, preferably an alkyl containing 1 to 12 (e.g., 1, 2, 3, 4, 5, 6, 7, 8, 9, 10, 11 and 12) carbon atoms, and more preferably an alkyl containing 1 to 6 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various side-chain isomers thereof, etc. More preferred is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl and the like. The alkyl may be substituted or unsubstituted. When substituted, the substituent may be substituted at any available connection site with one or more substituents preferably independently optionally selected from the group consisting of H, D, halogen, alkyl, alkoxy, haloalkyl, hydroxy, hydroxyalkyl, cyano, amino, nitro, cycloalkyl, heterocyclyl, aryl and heteroaryl.

The term "alkylene" refers to a saturated linear or branched aliphatic hydrocarbon group having 2 residues derived from the parent alkane by removal of two hydrogen atoms from the same carbon atom or two different carbon atoms, which is a linear or branched group containing 1 to 20 carbon atoms, preferably an alkylene group containing 1 to 12 (e.g., 1, 2, 3, 4, 5, 6, 7, 8, 9, 10, 11 and 12) carbon atoms, and more preferably an alkylene group containing 1 to 6 carbon atoms. Non-limiting examples of alkylene include, but are not limited to, methylene ($—CH_2—$), 1,1-ethylene ($—CH(CH_3)—$), 1,2-ethylene ($—CH_2CH_2—$), 1,1-propylene ($—CH(CH_2CH_3)—$), 1,2-propylene ($—CH_2CH(CH_3)—$), 1,3-propylene ($—CH_2CH_2CH_2—$), 1,4-butylene ($—CH_2CH_2CH_2CH_2—$) and the like. The alkylene may be substituted or unsubstituted. When substituted, the substituent may be substituted at any available connection site with one or more substituents preferably independently optionally selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocycloalkylthio and oxo.

The term "alkenyl" refers to an alkyl compound containing at least one carbon-carbon double bond in the molecule, wherein the alkyl is as defined above. The alkenyl may be substituted or unsubstituted. When substituted, the alkenyl may be substituted with one or more substituents preferably independently selected from the group consisting of hydrogen, alkyl, alkoxy, halogen, haloalkyl, hydroxy, hydroxyalkyl, cyano, amino, nitro, cycloalkyl, heterocyclyl, aryl and heteroaryl.

The term "alkynyl" refers to an alkyl compound containing at least one carbon-carbon triple bond in the molecule, wherein the alkyl is as defined above. The alkynyl may be substituted or unsubstituted. When substituted, the alkynyl may be substituted with one or more substituents preferably independently selected from the group consisting of hydrogen, alkyl, alkoxy, halogen, haloalkyl, hydroxy, hydroxyalkyl, cyano, amino, nitro, cycloalkyl, heterocyclyl, aryl and heteroaryl.

The term “cycloalkyl” refers to a saturated or partially unsaturated monocyclic or polycyclic hydrocarbon substituent. The cycloalkyl ring contains 3 to 20 carbon atoms, preferably 3 to 12 carbon atoms, more preferably 3 to 8 (e.g., 3, 4, 5, 6, 7 or 8) carbon atoms, and most preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like. Polycyclic cycloalkyl includes spiro cycloalkyl, fused cycloalkyl, and bridged cycloalkyl.

The term “spiro cycloalkyl” refers to a 5- to 20-membered polycyclic group in which monocyclic rings share one carbon atom (referred to as the spiro atom), wherein the spiro cycloalkyl may contain one or more double bonds. Preferably, the spiro cycloalkyl is 6- to 14-membered, and more preferably 7- to 10-membered (e.g., 7, 8, 9 or 10-membered). According to the number of the spiro atoms shared among the rings, the spiro cycloalkyl may be monospiro cycloalkyl, bispiro cycloalkyl or polyspiro cycloalkyl, preferably monospiro cycloalkyl and bispiro cycloalkyl, more preferably 4-membered/4-membered, 4-membered/5-membered, 4-membered/6-membered, 5-membered/5-membered or 5-membered/6-membered monospiro cycloalkyl. Non-limiting examples of spiro cycloalkyl include:

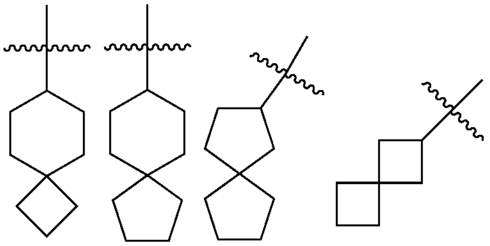

and

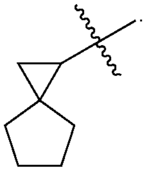

The term “fused cycloalkyl” refers to a 5- to 20-membered carbon polycyclic group in which each ring shares a pair of adjacent carbon atoms with the other rings in the system, wherein one or more of the rings may contain one or more double bonds. Preferably, the fused cycloalkyl is 6- to 14-membered, and more preferably 7- to 10-membered (e.g., 7, 8, 9 or 10-membered). According to the number of the formed rings, the fused cycloalkyl may be bicyclic, tricyclic, tetracyclic or polycyclic cycloalkyl, preferably bicyclic or tricyclic cycloalkyl, and more preferably 3-membered/4-membered, 3-membered/5-membered, 3-membered/6-membered, 4-membered/4-membered, 4-membered/5-membered, 4-membered/6-membered, 5-membered/4-membered, 5-membered/5-membered, 5-membered/6-membered, 6-membered/3-membered, 6-membered/4-membered, 6-membered/5-membered and 6-membered/6-membered bicyclic cycloalkyl. Non-limiting examples of fused cycloalkyl include:

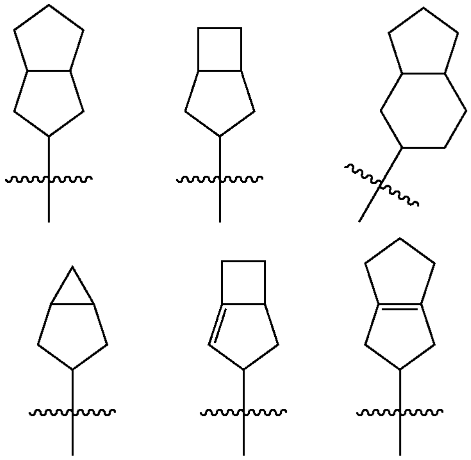

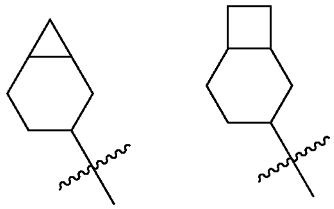

and

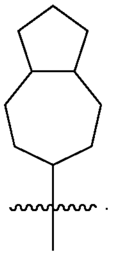

The term “bridged cycloalkyl” refers to a 5- to 20-membered carbon polycyclic group in which any two rings share two carbon atoms that are not directly connected to each other, wherein the bridged cycloalkyl may contain one or more double bonds. Preferably, the bridged cycloalkyl is 6- to 14-membered, and more preferably 7- to 10-membered (e.g., 7, 8, 9 or 10-membered). According to the number of the formed rings, the bridged cycloalkyl may be bicyclic, tricyclic, tetracyclic or polycyclic, preferably bicyclic, tricyclic or tetracyclic, and more preferably bicyclic or tricyclic. Non-limiting examples of bridged cycloalkyl include:

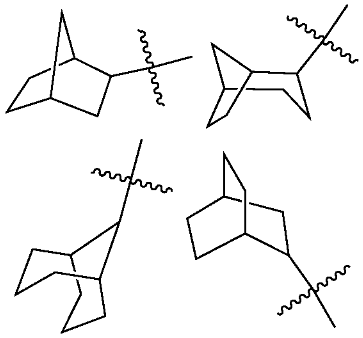

-continued

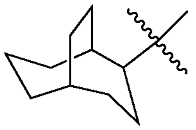

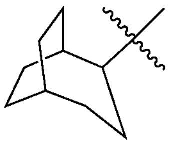

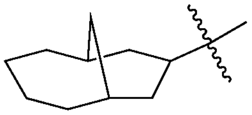

and

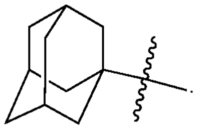

The cycloalkyl ring includes those in which the cycloalkyl described above (including monocyclic, spiro, fused and bridged rings) is fused to an aryl, heteroaryl or heterocycloalkyl ring, wherein the ring connected to the parent structure is cycloalkyl. Non-limiting examples include indanyl, tetrahydronaphthyl, benzocyclopentyl, benzocycloheptanyl, and the like, preferably benzocyclopentyl and tetrahydronaphthyl.

The cycloalkyl may be substituted or unsubstituted. When substituted, the substituent may be substituted at any available connection site with one or more substituents preferably independently optionally selected from the group consisting of hydrogen, halogen, alkyl, alkoxy, haloalkyl, hydroxy, hydroxyalkyl, cyano, amino, nitro, cycloalkyl, heterocyclyl, aryl and heteroaryl.

The term “alkoxy” refers to —O-(alkyl) and —O-(unsubstituted cycloalkyl), wherein the alkyl is as defined above. Non-limiting examples of alkoxy include: methoxy, ethoxy, propoxy, butoxy, cyclopropyloxy, cyclobutoxy, cyclopentyloxy, cyclohexyloxy. The alkoxy may be substituted or unsubstituted. When substituted, the alkoxy may be substituted with one or more substituents preferably independently selected from the group consisting of H, D, halogen, alkyl, alkoxy, haloalkyl, hydroxy, hydroxyalkyl, cyano, amino, nitro, cycloalkyl, heterocyclyl, aryl and heteroaryl. The term “heterocyclyl” refers to a saturated or partially unsaturated monocyclic or polycyclic hydrocarbon substituent containing 3 to 20 ring atoms, wherein one or more of the ring atoms are heteroatoms selected from the group consisting of nitrogen, oxygen, S, S(O) and $S(O)_2$, excluding a cyclic portion of —O—O—, —O—S— or —S—S—, and the remaining ring atoms are carbon. The heterocyclyl preferably contains 3 to 12 ring atoms, wherein 1 to 4 (e.g., 1, 2, 3 and 4) are heteroatoms; more preferably, contains 3 to 8 (e.g., 3, 4, 5, 6, 7 or 8) ring atoms, wherein 1 to 3 (e.g., 1, 2 or 3) are heteroatoms; even more preferably, contains 3 to 6 ring atoms, wherein 1 to 3 are heteroatoms; and most preferably, contains 5 or 6 ring atoms, wherein 1 to 3 are heteroatoms. Non-limiting examples of monocyclic heterocyclyl include pyrrolidinyl, tetrahydropyranyl, 1,2,3,6-tetrahydropyridinyl, piperidinyl, piperazinyl, morpholinyl, thiomorpholinyl, homopiperazinyl, and the like. Polycyclic heterocyclyl includes spiro heterocyclyl, fused heterocyclyl, and bridged heterocyclyl.

The term “spiro heterocyclyl” refers to a 5- to 20-membered polycyclic heterocyclyl group in which monocyclic rings share one atom (referred to as the spiro atom), wherein one or more ring atoms are heteroatoms selected from the group consisting of nitrogen, oxygen, S, S(O) and $S(O)_2$, and the remaining ring atoms are carbon atoms. The spiro heterocyclyl may contain one or more double bonds. Preferably, the spiro heterocyclyl is 6- to 14-membered, and more preferably 7- to 10-membered. According to the number of spiro atoms shared among the rings, the spiro heterocyclyl may be monospiro heterocyclyl, bispiro heterocyclyl or polyspiro heterocyclyl, preferably monospiro heterocyclyl and bispiro heterocyclyl, and more preferably 4-membered/4-membered, 4-membered/5-membered, 4-membered/6-membered, 5-membered/5-membered or 5-membered/6-membered monospiro heterocyclyl. Non-limiting examples of spiro heterocyclyl include:

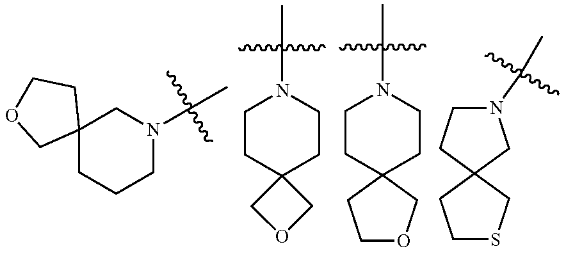

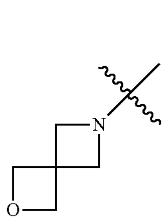

and

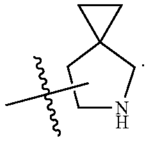

The term “fused heterocyclyl” refers to a 5- to 20-membered polycyclic heterocyclyl group in which each ring shares a pair of adjacent atoms with the other rings in the system, wherein one or more of the rings may contain one or more double bonds. In the fused heterocyclyl, one or more of the ring atoms are heteroatoms selected from the group consisting of nitrogen, oxygen, S, S(O) and $S(O)_2$, and the remaining ring atoms are carbon atoms. Preferably, the fused heterocyclyl is 6- to 14-membered, and more preferably 7- to 10-membered (e.g., 7, 8, 9 or 10-membered). According to the number of the formed rings, the fused heterocyclyl may be bicyclic, tricyclic, tetracyclic or polycyclic fused heterocyclyl, preferably bicyclic or tricyclic fused heterocyclyl, and more preferably 3-membered/4-membered, 3-membered/5-membered, 3-membered/6-membered, 4-membered/4-membered, 4-membered/5-membered, 4-membered/6-membered, 5-membered/5-membered, 5-membered/6-membered, 6-membered/3-membered, 6-membered/4-membered, 6-membered/5-membered and 5-membered/4-membered, 6-membered/6-membered bicyclic fused heterocyclyl. Non-limiting examples of fused heterocyclyl include:

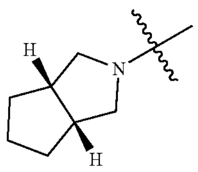

,

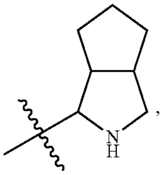

,

-continued

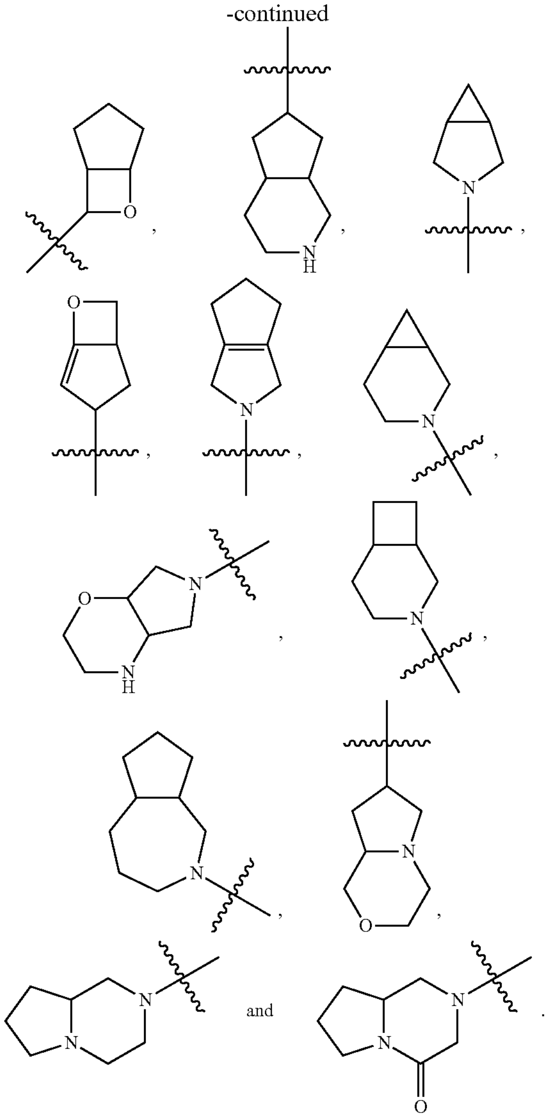

and

The term "bridged heterocyclyl" refers to a 5- to 14-membered polycyclic heterocyclyl group in which any two rings share two carbon atoms that are not directly connected to each other, wherein the bridged heterocyclyl may contain one or more double bonds. In the bridged heterocyclyl, one or more of the ring atoms are heteroatoms selected from the group consisting of nitrogen, oxygen, S, S(O) and $S(O)_2$, and the remaining ring atoms are carbon atoms. Preferably, the bridged heterocyclyl is 6- to 14-membered, and more preferably 7- to 10-membered (e.g., 7, 8, 9 or 10-membered). According to the number of the formed rings, the bridged heterocyclyl may be bicyclic, tricyclic, tetracyclic or polycyclic, preferably bicyclic, tricyclic or tetracyclic, and more preferably bicyclic or tricyclic. Non-limiting examples of bridged heterocyclyl include:

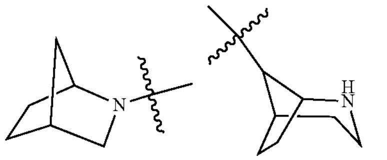

-continued

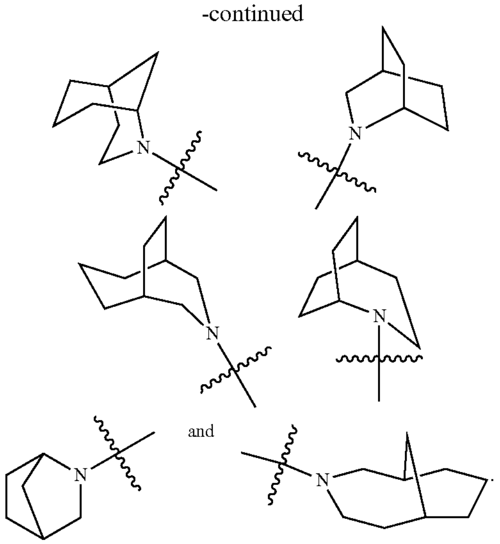

and

The heterocyclyl ring includes those in which the heterocyclyl described above (including monocyclic, spiro heterocyclic, fused heterocyclic and bridged heterocyclic rings) is fused to an aryl, heteroaryl or cycloalkyl ring, wherein the ring connected to the parent structure is heterocyclyl. Non-limiting examples include:

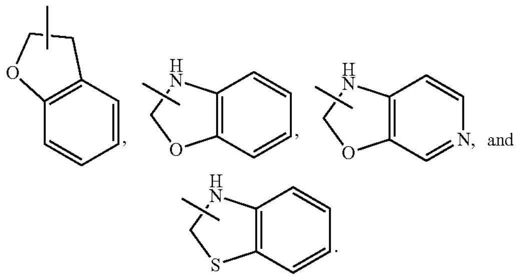

and

The heterocyclyl may be substituted or unsubstituted. When substituted, the substituent may be substituted at any available connection site with one or more substituents preferably independently optionally selected from the group consisting of hydrogen, halogen, alkyl, alkoxy, haloalkyl, hydroxy, hydroxyalkyl, cyano, amino, nitro, cycloalkyl, heterocyclyl, aryl and heteroaryl.

The term "aryl" refers to a 6- to 14-membered, preferably 6- to 10-membered carbon monocyclic or fused polycyclic (fused polycyclic rings are those sharing a pair of adjacent carbon atoms) group having a conjugated π-electron system such as phenyl and naphthyl. The aryl ring includes those in which the aryl ring described above is fused to a heteroaryl, heterocyclyl or cycloalkyl ring, wherein the ring connected to the parent structure is an aryl ring. Non-limiting examples include:

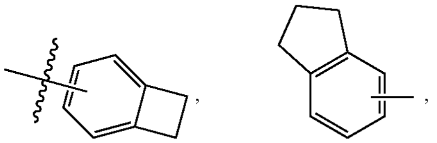

-continued

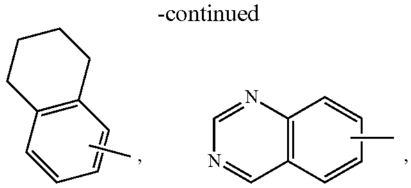

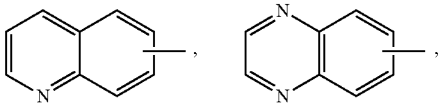

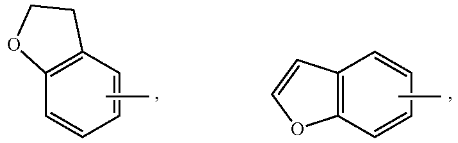

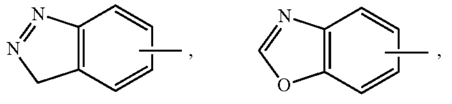

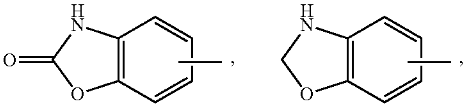

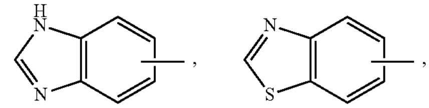

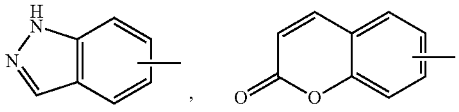

and

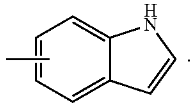

The aryl may be substituted or unsubstituted. When substituted, the substituent may be substituted at any available connection site with one or more substituents preferably independently optionally selected from the group consisting of hydrogen, halogen, alkyl, alkoxy, haloalkyl, hydroxy, hydroxyalkyl, cyano, amino, nitro, cycloalkyl, heterocyclyl, aryl and heteroaryl.

The term "heteroaryl" refers to a heteroaromatic system containing 1 to 4 (e.g., 1, 2, 3 and 4) heteroatoms and 5 to 14 ring atoms, wherein the heteroatoms are selected from the group consisting of oxygen, sulfur and nitrogen. The heteroaryl is preferably 5- to 10-membered (e.g., 5, 6, 7, 8, 9 and 10) and more preferably 5- or 6-membered, e.g., furanyl, thienyl, pyridinyl, pyrrolyl, N-alkylpyrrolyl, pyrimidinyl, pyrazinyl, pyridazinyl, imidazolyl, pyrazolyl, triazolyl, and tetrazolyl. The heteroaryl ring includes those in which the heteroaryl ring described above is fused to an aryl, heterocyclyl or cycloalkyl ring, wherein the ring connected to the parent structure is a heteroaryl ring. Non-limiting examples include:

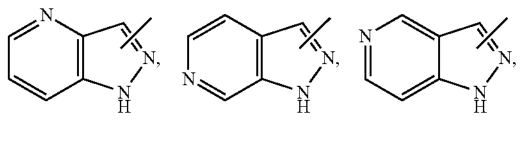

-continued

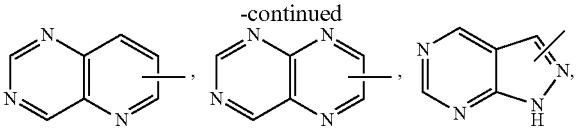

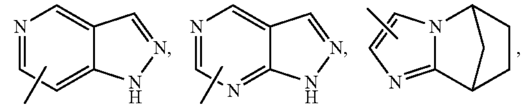

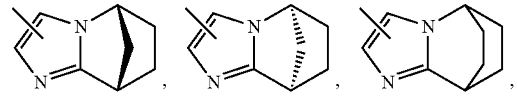

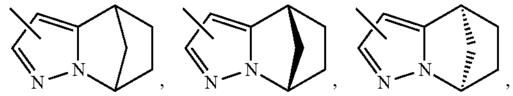

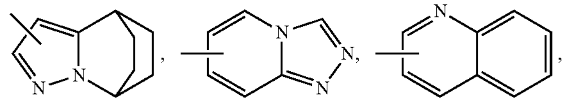

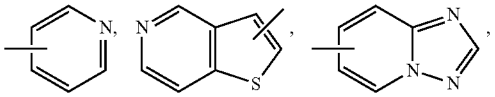

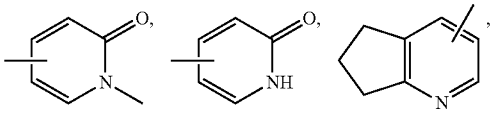

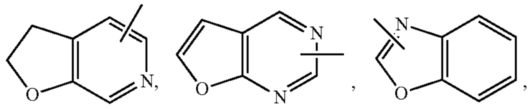

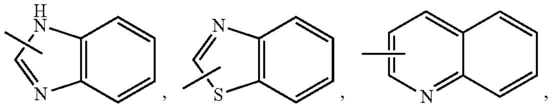

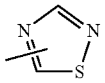

and

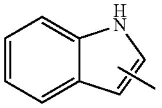

The heteroaryl may be substituted or unsubstituted. When substituted, the substituent may be substituted at any available connection site with one or more substituents preferably independently optionally selected from the group consisting of hydrogen, halogen, alkyl, alkoxy, haloalkyl, hydroxy, hydroxyalkyl, cyano, amino, nitro, cycloalkyl, heterocyclyl, aryl and heteroaryl.

The cycloalkyl, heterocyclyl, aryl and heteroaryl described above have 1 residue derived from the parent ring by removal of one hydrogen atom from a ring atom, or 2 residues derived from the parent ring by removal of two hydrogen atoms from the same ring atom or two different ring atoms, i.e., "divalent cycloalkyl", "divalent heterocyclyl", "arylene", or "heteroarylene".

The term "amino protecting group" refers to a group that can be easily removed and is intended to protect an amino group from being changed when a reaction is conducted elsewhere in the molecule. Non-limiting examples include tetrahydropyranyl, tert-butoxycarbonyl, acetyl, benzyl, allyl, p-methoxybenzyl, and the like. These groups may be optionally substituted with 1 to 3 substituents selected from the group consisting of halogen, alkoxy and nitro. The amino protecting group is preferably tetrahydropyranyl.

The term "cycloalkyloxy" refers to cycloalkyl-O—, wherein the cycloalkyl is as defined above.

The term "haloalkyl" refers to an alkyl group substituted with one or more halogens, wherein the alkyl group is as defined above.

The term "deuterated alkyl" refers to an alkyl group substituted with one or more deuterium atoms, wherein the alkyl group is as defined above.

The term "hydroxy" refers to —OH group.

The term "hydroxyalkyl" refers to an alkyl group substituted with hydroxy, wherein the alkyl group is as defined above.

The term "halogen" refers to fluorine, chlorine, bromine or iodine.

The term "amino" refers to $-NH_2$.

The term "cyano" refers to —CN.

The term "nitro" refers to $-NO_2$.

The term "carbonyl" refers to C═O.

The term "carboxy" refers to —C(O)OH.

The term "carboxylate" refers to —C(O)O(alkyl) or —C(O)O(cycloalkyl), wherein the alkyl and cycloalkyl are as defined above.

THP refers to tetrahydropyranyl.

The compounds disclosed herein may be present as tautomers. For the purposes of the present disclosure, reference to a compound of formula (I) refers to the compound itself, or any one tautomer thereof itself, or a mixture of two or more tautomers. For example, reference to pyrazolyl is understood to include any one of the following two structures or a mixture of the two tautomers,

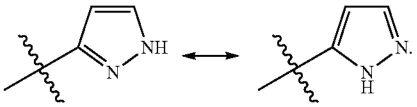 [SMILES: *c1cc[nH]n1 ; *c1ccn[nH]1]

The compounds disclosed herein include isotopic derivatives thereof. The term "isotopic derivative" refers to compounds that differ in structure only by having one or more enriched isotopic atoms. For example, compounds having the structure disclosed herein having "deuterium" or "tritium" in place of hydrogen, or $^{18}F$-fluorine labeling ($^{18}F$ isotope) in place of fluorine, or $^{11}C$-, $^{13}C$- or $^{14}C$-enriched carbon ($^{11}C$-, $^{13}C$- or $^{14}C$-carbon labeling; $^{11}C$-, $^{13}C$- or $^{14}C$-isotope) in place of a carbon atom are within the scope of the present disclosure. Such a compound can be used as an analytical tool or a probe in, for example, a biological assay, or may be used as a tracer for in vivo diagnostic imaging of disease, or as a tracer in a pharmacodynamic, pharmacokinetic or receptor study. The present disclosure encompasses various deuterated forms of the compounds of formula (I). Each available hydrogen atom connected to a carbon atom may be independently replaced with a deuterium atom. Those skilled in the art are able to synthesize the compounds of formula (I) in deuterated form with reference to the relevant literature. Commercially available deuterated starting materials can be used in preparing the deuterated forms of the compounds of formula (I), or they can be synthesized using conventional techniques with deuterated reagents including, but not limited to, deuterated borane, tri-deuterated borane in tetrahydrofuran, deuterated lithium aluminum hydride, deuterated iodoethane, deuterated iodomethane, and the like.

The term "optional" or "optionally" means that the event or circumstance subsequently described may, but not necessarily, occur, and that the description includes instances where the event or circumstance occurs or does not occur. For example, "a heterocyclyl group optionally substituted with alkyl" means that alkyl may be, but not necessarily, present, and that the description includes instances where the heterocyclyl group is or is not substituted with alkyl.

The term "substituted" means that one or more, preferably up to 5, more preferably 1 to 3 hydrogen atoms in the group are independently substituted with a corresponding number of substituents. It goes without saying that a substituent is only in its possible chemical position, and those skilled in the art will be able to determine (experimentally or theoretically) possible or impossible substitution without undue efforts. For example, it may be unstable when an amino or hydroxy group having a free hydrogen is bound to a carbon atom having an unsaturated (e.g., olefinic) bond.

The term "pharmaceutical composition" refers to a mixture containing one or more of the compounds described herein or a physiologically/pharmaceutically acceptable salt or pro-drug thereof, and other chemical components, for example physiologically/pharmaceutically acceptable carriers and excipients. The purpose of the pharmaceutical composition is to promote the administration to an organism, which facilitates the absorption of the active ingredient, thereby exerting biological activities.

The term "pharmaceutically acceptable salt" refers to salts of the disclosed compounds which are safe and effective for use in the body of a mammal and possess the requisite biological activities.

For drugs and pharmacological active agents, the term "therapeutically effective amount" refers to an amount of a medicament or an agent that is sufficient to provide the desired effect but is non-toxic. The determination of the effective amount varies from person to person. It depends on the age and general condition of a subject, as well as the particular active substance used. The appropriate effective amount in a case may be determined by those skilled in the art in the light of routine tests.

Synthesis of Compounds Disclosed Herein

In order to achieve the purpose of the present disclosure, the following technical schemes are adopted in the present disclosure:

Scheme 1

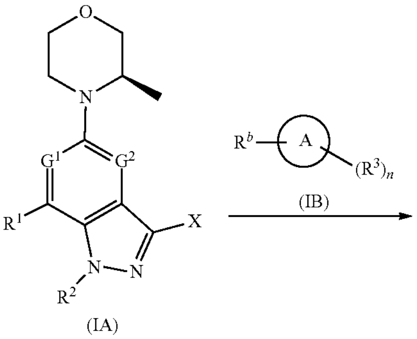
(IA) (IB)

-continued

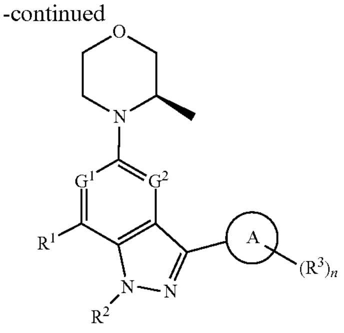

(I)

A method for preparing the compound of formula (I) or the salt thereof disclosed herein comprises the following steps:

subjecting a compound of formula (LA) and a compound of formula (IB) to a coupling reaction in an alkaline condition in the presence of a catalyst to obtain the compound of formula (I), wherein:

X is halogen, preferably Br;

$R^b$ is

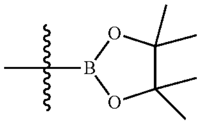 or 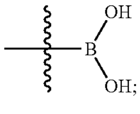

and ring A, $G^1$, $G^2$, $R^1$, $R^2$, $R^3$ and n are as defined in formula (I).

Scheme 2

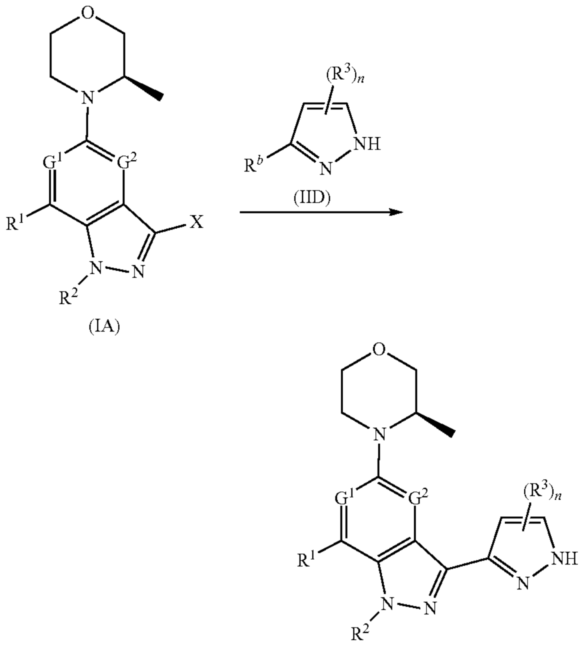

(IA) (IID) (II)

A method for preparing the compound of formula (II) or the salt thereof disclosed herein comprises the following steps:

subjecting a compound of formula (IA) and a compound of formula (IID) to a coupling reaction in an alkaline condition in the presence of a catalyst to obtain the compound of formula (II), wherein:

X is halogen, preferably Br;

$R^b$ is

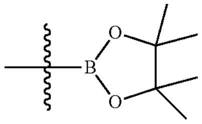 or 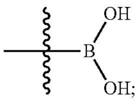

and $G^1$, $G^2$, $R^1$, $R^2$, $R^3$ and n are as defined in formula (II).

Scheme 3

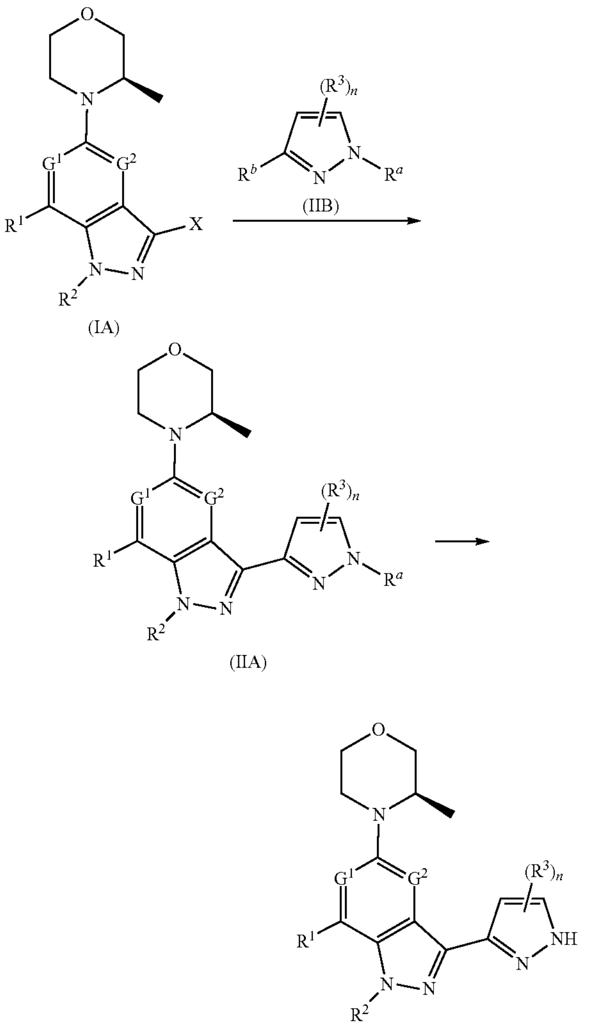

(IA) (IIB) (IIA) (II)

A method for preparing the compound of formula (II) or the salt thereof disclosed herein comprises the following steps:

subjecting a compound of formula (IA) and a compound of formula (IIB) to a coupling reaction in an alkaline condition in the presence of a catalyst to obtain a compound of formula (IIA); and removing an amino protecting group from the compound of formula (IIA) in an acidic condition to obtain the compound of formula (II), wherein:

X is halogen, preferably Br;

$R^b$ is

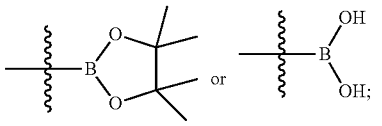

and $G^1$, $G^2$, $R^1$, $R^2$, $R^3$ and n are as defined in formula (II).

Scheme 4

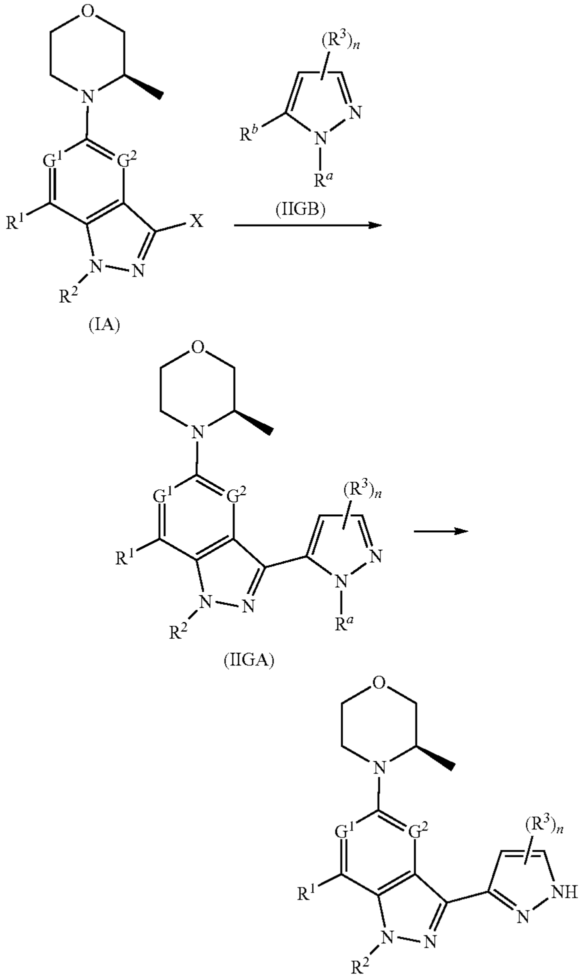

(IA)

(IIGB)

(IIGA)

(II)

A method for preparing the compound of formula (II) or the salt thereof disclosed herein comprises the following steps:

subjecting a compound of formula (IA) and a compound of formula (IIGB) to a coupling reaction in an alkaline condition in the presence of a catalyst to obtain a compound of formula (IIGA); and removing an amino protecting group from the compound of formula (IIGA) in an acidic condition to obtain the compound of formula (II), wherein:

X is halogen, preferably Br;

$R^b$ is

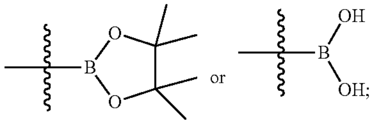

and $G^1$, $G^2$, $R^1$, $R^2$, $R^3$ and n are as defined in formula (II).

Scheme 5

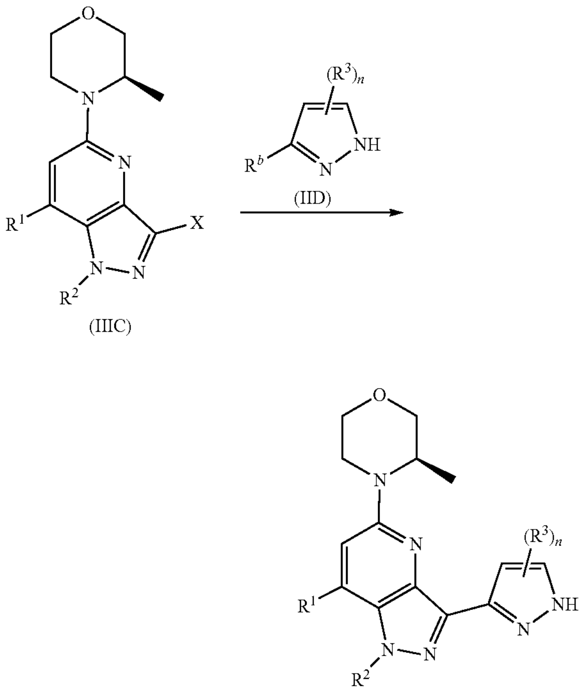

(IIIC)

(IID)

(III)

A method for preparing the compound of formula (III) or the salt thereof disclosed herein comprises the following steps:

subjecting a compound of formula (IIIC) and a compound of formula (IID) to a coupling reaction in an alkaline condition in the presence of a catalyst to obtain the compound of formula (III), wherein:

X is halogen, preferably Br;

$R^b$ is

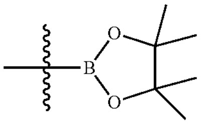

or

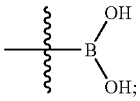

and $R^1$, $R^2$, $R^3$ and n are as defined in formula (III).

Scheme 6

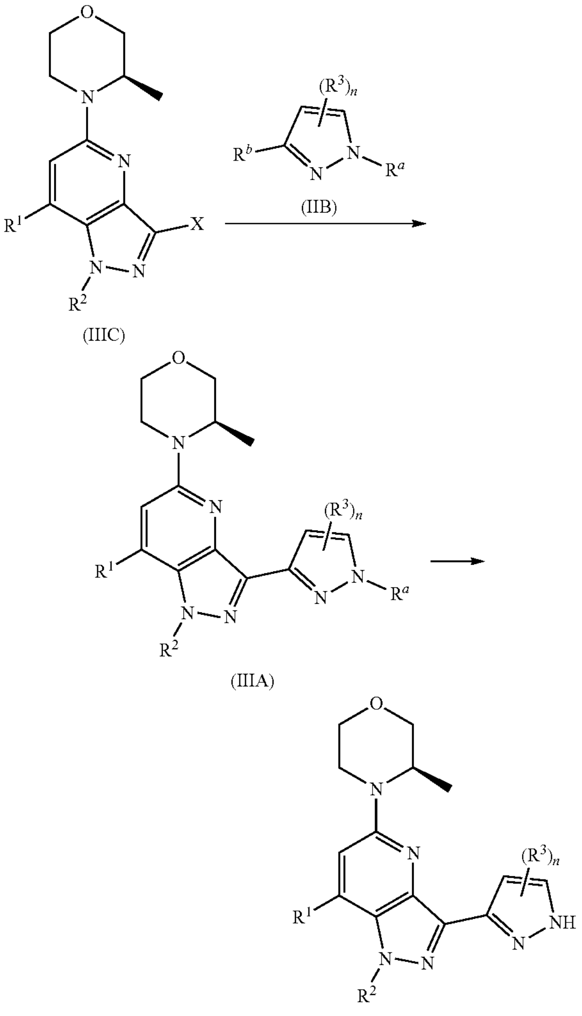

(IIIC) (IIB) (IIIA) (III)

A method for preparing the compound of formula (III) or the salt thereof disclosed herein comprises the following steps:

subjecting a compound of formula (IIIC) and a compound of formula (IIB) to a coupling reaction in an alkaline condition in the presence of a catalyst to obtain a compound of formula (IIIA); and removing an amino protecting group from the compound of formula (IIIA) in an acidic condition to obtain the compound of formula (III), wherein:

X is halogen, preferably Br;

$R^a$ is the amino protecting group;

$R^b$ is

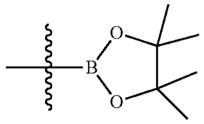

or

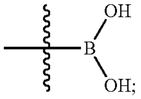

and $R^1$, $R^2$, $R^3$ and n are as defined in formula (III).

Scheme 7

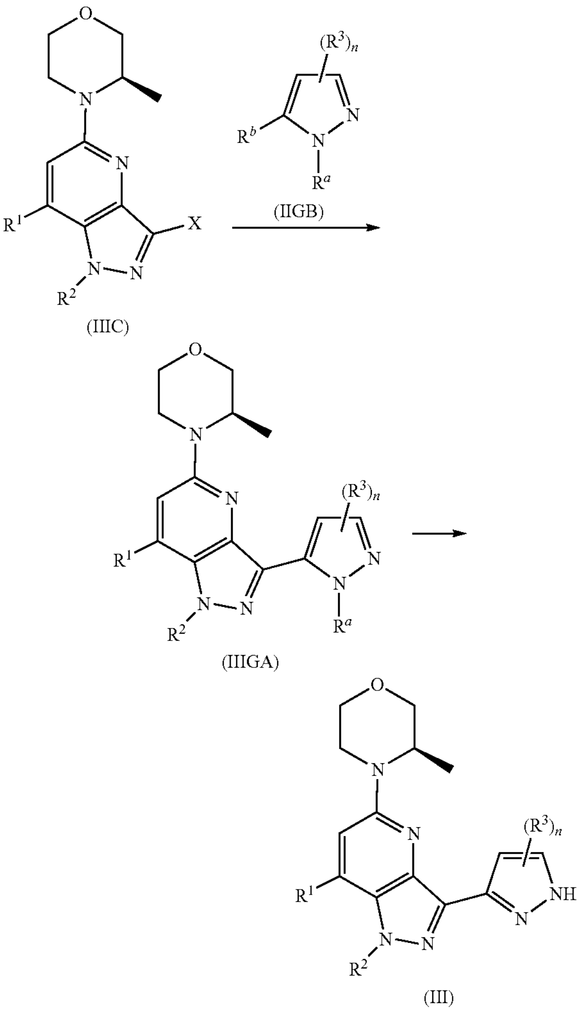

(IIIC) (IIGB) (IIIGA) (III)

A method for preparing the compound of formula (III) or the salt thereof disclosed herein comprises the following steps:

subjecting a compound of formula (IIIC) and a compound of formula (IIGB) to a coupling reaction in an alkaline condition in the presence of a catalyst to obtain a compound of formula (IIIGA); and removing an amino protecting group from the compound of formula (IIIGA) in an acidic condition to obtain the compound of formula (III), wherein:

X is halogen, preferably Br;

$R^a$ is the amino protecting group;

$R^b$ is

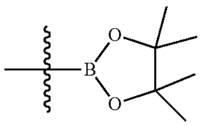

or

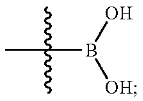

and $R^1$, $R^2$, $R^3$ and n are as defined in formula (III).

Scheme 8

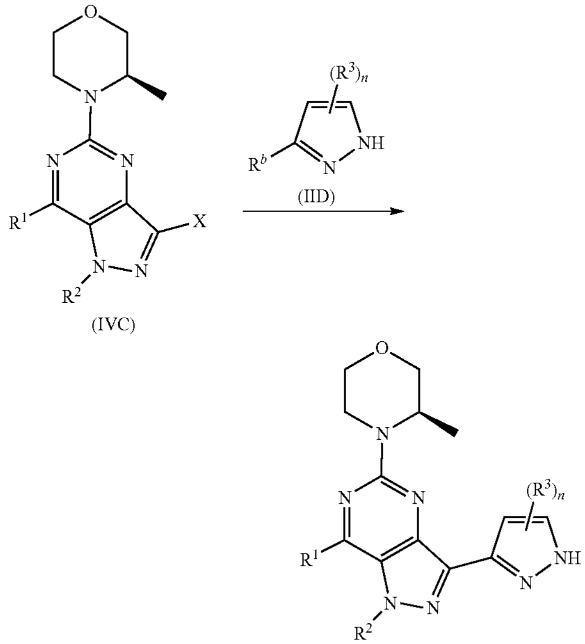

(IVC) (IID) (IV)

A method for preparing the compound of formula (IV) or the salt thereof disclosed herein comprises the following steps:

subjecting a compound of formula (IVC) and a compound of formula (IID) to a coupling reaction in an alkaline condition in the presence of a catalyst to obtain the compound of formula (IV), wherein:

X is halogen, preferably Br;

$R^b$ is

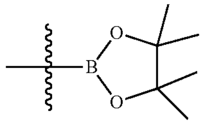

or

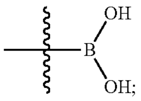

and $R^1$, $R^2$, $R^3$ and n are as defined in formula (IV).

Scheme 9

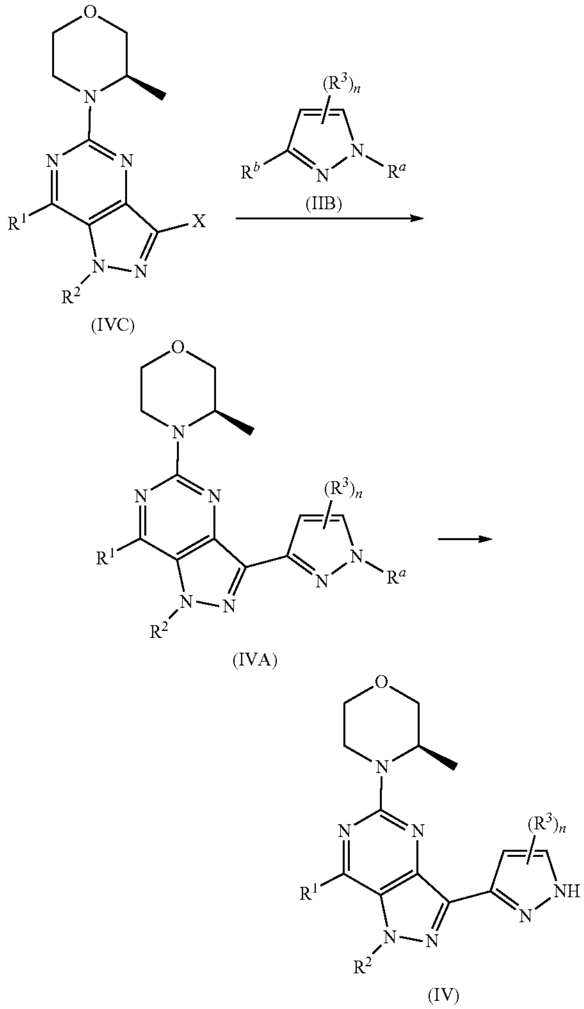

(IVC) (IIB) (IVA) (IV)

A method for preparing the compound of formula (IV) or the salt thereof disclosed herein comprises the following steps:

subjecting a compound of formula (IVC) and a compound of formula (IIB) to a coupling reaction in an alkaline condition in the presence of a catalyst to obtain a compound of formula (IVA); and removing an amino protecting group from the compound of formula (IVA) in an acidic condition to obtain the compound of formula (IV), wherein:

X is halogen, preferably Br;

$R^a$ is the amino protecting group;

$R^b$ is

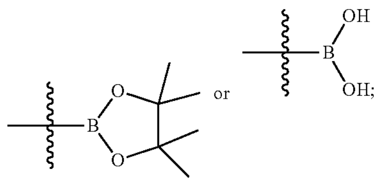

and $R^1$, $R^2$, $R^3$ and n are as defined in formula (IV).

Scheme 10

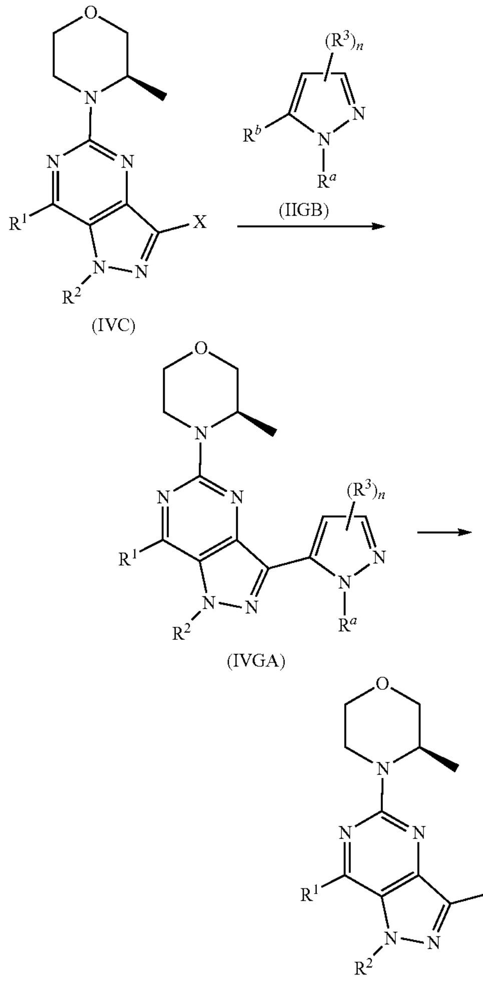

(IVC) (IIGB) (IVGA) (IV)

A method for preparing the compound of formula (IV) or the salt thereof disclosed herein comprises the following steps:

subjecting a compound of formula (IVC) and a compound of formula (IIGB) to a coupling reaction in an alkaline condition in the presence of a catalyst to obtain a compound of formula (IVGA); and removing an amino protecting group from the compound of formula (IVGA) in an acidic condition to obtain the compound of formula (IV), wherein:

X is halogen, preferably Br;

$R^a$ is the amino protecting group;

$R^b$ is

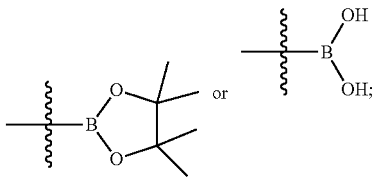

and $R^1$, $R^2$, $R^3$ and n are as defined in formula (IV).

The reagents that provide alkaline conditions in the above synthesis schemes include organic bases including, but not limited to, triethylamine, N,N-diisopropylethylamine, n-butyllithium, lithium diisopropylamide, lithium bis(trimethylsilyl)amide, potassium acetate, sodium tert-butoxide, potassium tert-butoxide and sodium n-butoxide, and inorganic bases including, but not limited to, sodium hydride, potassium phosphate, sodium carbonate, potassium carbonate, cesium carbonate, sodium hydroxide and lithium hydroxide.

The catalysts described in the above synthesis schemes include, but are not limited to, palladium on carbon, tetrakis (triphenylphosphine)palladium(0), palladium dichloride, palladium acetate, bis(triphenylphosphine)palladium(II) dichloride, bis(dibenzylideneacetone)palladium, chlorine (2-dicyclohexylphosphino-2',4',6'-triisopropyl-1,1'-biphenyl) [2-(2'-amino-1,1'-biphenyl)]palladium, [1,1'-bis(diphenylphosphino)ferrocene]palladium(II) dichloride, [1,1'-bis (dibenzylphosphino)ferrocene]palladium dichloride or tris (dibenzylideneacetone)dipalladium(0), preferably tetrakis (triphenylphosphine)palladium(0)) or bis (triphenylphosphine)palladium(II) dichloride.

The reagents that provide acidic conditions in the above synthesis schemes include, but are not limited to, hydrogen chloride, hydrogen chloride in 1,4-dioxane, trifluoroacetic acid, formic acid, acetic acid, hydrochloric acid, sulfuric acid, methanesulfonic acid, nitric acid, phosphoric acid, p-toluenesulfonic acid, $Me_3SiCl$, TMSOTf, preferably trifluoroacetic acid.

The amino protecting groups in the above synthetic schemes include, but are not limited to, tetrahydropyranyl (THP), tert-butyloxycarbonyl, acetyl, benzyl, allyl and p-methoxybenzyl. These groups may be optionally substituted with 1-3 substituents selected from the group consisting of halogen, alkoxy and nitro. Tetrahydropyranyl is preferred.

The above reactions are preferably conducted in a solvent including, but not limited to: ethylene glycol dimethyl ether, acetic acid, methanol, ethanol, n-butanol, toluene, tetrahydrofuran, dichloromethane, petroleum ether, ethyl acetate, n-hexane, dimethyl sulfoxide, 1,4-dioxane, water or N,N-dimethylformamide.

DETAILED DESCRIPTION

The following examples further illustrate the present disclosure, but the present disclosure is not limited thereto.

EXAMPLES

The structure of the compound was determined by nuclear magnetic resonance (NMR) spectroscopy and/or mass spectrometry (MS). NMR shift (8) is given in a unit of $10^{-6}$ (ppm). NMR spectra were measured using a Bruker AVANCE-400 nuclear magnetic resonance instrument, with deuterated dimethyl sulfoxide (DMSO-$d_6$), deuterated chloroform ($CDCl_3$) and deuterated methanol ($CD_3OD$) as determination solvents, with tetramethylsilane (TMS) as internal standard.

Mass spectra were measured using Agilent 1200/1290 DAD-6110/6120 Quadrupole MS liquid chromatography-mass spectrometry system (manufacturer: Agilent; MS model: 6110/6120 Quadrupole MS), Waters ACQuity UPLC-QD/SQD (manufacturer: Waters, MS model: Waters ACQuity Qda Detector/waters SQ Detector) and THERMO Ultimate 3000-Q Exactive (manufacturer: THERMO, MS model: THERMO Q Exactive).

High performance liquid chromatography (HPLC) was performed using Agilent HPLC 1200DAD, Agilent HPLC 1200VWD and Waters HPLC e2695-2489 high pressure liquid chromatography.

Chiral HPLC was performed on Agilent 1260 DAD HPLC.

HPLC preparation was performed using Waters 2545-2767, Waters 2767-SQ Detecor2, Shimadzu LC-20AP and Gilson GX-281 preparative chromatographs.

Chiral preparation was performed on a Shimadzu LC-20AP preparative chromatograph.

A CombiFlash Rf200 (TELEDYNE ISCO) system was used for rapid preparation.

Huanghai HSGF254 or Qingdao GF254 silica gel plates of specifications 0.15 mm to 0.2 mm were adopted for thin layer chromatography (TLC) analysis and 0.4 mm to 0.5 mm for TLC separation and purification.

The silica gel column chromatography generally used 200 to 300-mesh silica gel (Huanghai, Yantai) as the carrier.

The mean inhibition of kinase and the $IC_{50}$ value were measured using a NovoStar microplate reader (BMG, Germany).

Known starting materials described herein may be synthesized using or according to methods known in the art, or may be purchased from ABCR GmbH & Co. KG, Acros Organics, Aldrich Chemical Company, Accela ChemBio Inc., Chembee Chemicals, and other companies.

In the examples, the reactions were performed in an argon atmosphere or a nitrogen atmosphere unless otherwise specified.

An argon atmosphere or a nitrogen atmosphere means that the reaction flask is connected to a balloon containing about 1 L of argon or nitrogen.

A hydrogen atmosphere means that the reaction flask is connected to a balloon containing about 1 L of hydrogen.

Parr 3916EKX hydrogenator, Qinglan QL-500 hydrogenator or HC2-SS hydrogenator was used for pressurized hydrogenation reactions.

The hydrogenation reaction usually involved 3 cycles of vacuumization and hydrogen purge.

A CEM Discover-S 908860 microwave reactor was used for the microwave reaction.

In the examples, a solution refers to an aqueous solution unless otherwise specified.

In the examples, the reaction temperature was room temperature, i.e., 20° C. to 30° C., unless otherwise specified.

The monitoring of the reaction progress in the examples was conducted by thin layer chromatography (TLC). The developing solvent for reactions, the eluent system for column chromatography purification and the developing solvent system for thin layer chromatography included: A: dichloromethane/methanol system, B: n-hexane/ethyl acetate system, and C: petroleum ether/ethyl acetate system. The volume ratio of the solvents was adjusted according to the polarity of the compound, or by adding a small amount of basic or acidic reagents such as triethylamine, and acetic acid.

THP refers to tetrahydropyranyl.

Example 1

(R)-2-methyl-2-(1-methyl-5-(3-methylmorpholinyl)-3-(1H-pyrazol-3-yl)-1H-pyrazolo[4,3-b]pyridin-7-yl) propanenitrile 1

1

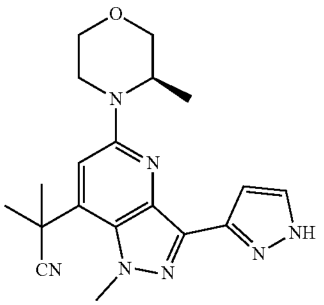

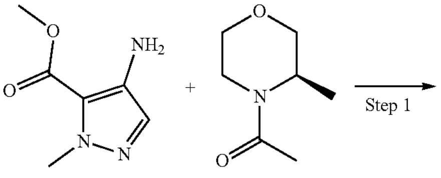

1a 1b

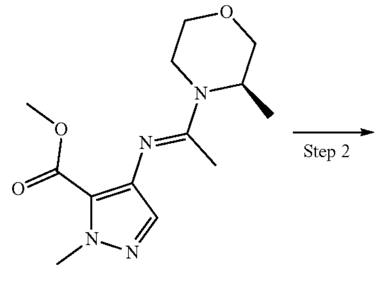

1c

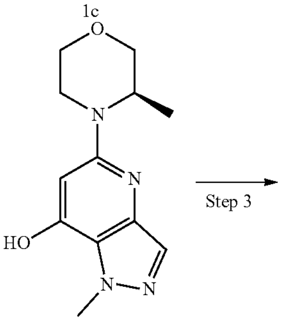

1d

-continued

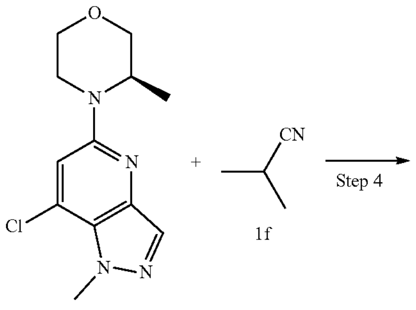

1e 1f

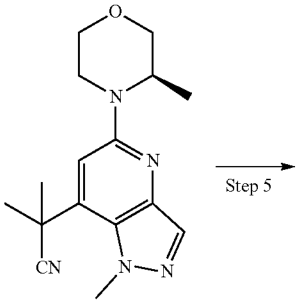

1g

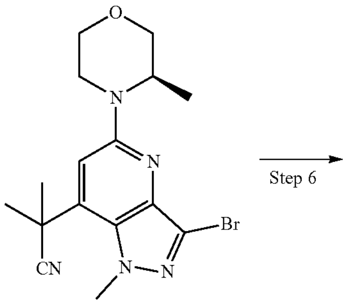

1h

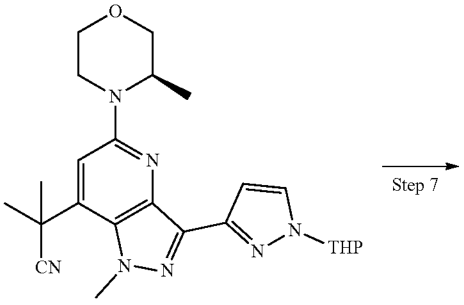

1i

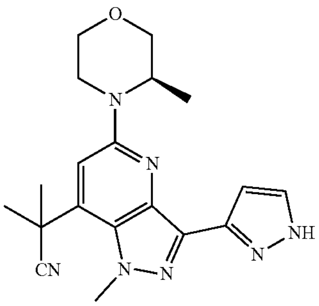

1

Step 1

Methyl(R,E)-1-methyl-4-((1-(3-methylmorpholino) ethylidene)amino)-1H-pyrazole-5-carboxylate 1c Compound (R)-1-(3-methylmorpholinyl) ethan-1-one 1b (2.5 g, 17.7 mmol, prepared by the method disclosed on page 86 for intermediate-1 in the Example of the Patent Publication No. WO2016020320A1) was dissolved in 1,2-dichloroethane, and cooled in an ice/water bath in an argon atmosphere. Phosphorus oxychloride (7.4 g, 48.3 mmol) was slowly and dropwise added before the mixture was stirred at room temperature for 30 min. Compound methyl 4-amino-1-methyl-1H-pyrazole-5-carboxylate 1a (2.5 g, 16.1 mmol, Jiangsu Aikon) was added. The reaction system was heated to 80° C. and stirred for 2 h. The mixture was cooled to room temperature and concentrated at reduced pressure. The residue was diluted with dichloromethane (200 mL), and cooled in an ice/water bath. Saturated sodium bicarbonate solution was added dropwise to neutralize the dilution to pH 8 to 9. The organic phase was washed with saturated brine (50 mL), dried over anhydrous sodium sulfate and filtered. The filtrate was purified by silica gel column chromatography with eluent system C to obtain the target compound 1c (4.8 g, 94% yield).

MS m/z (ESI): 281.2 [M+1].

Step 2

(R)-1-methyl-5-(3-methylmorpholinyl)-1H-pyrazolo [4,3-b]pyridin-7-ol 1d

Compound 1c (2.6 g, 9.3 mmol) was dissolved in tetrahydrofuran (20 mL) and cooled in an ice/water bath. Lithium bis(trimethylsilyl)amide (27.8 mL, a 1 M solution in tetrahydrofuran, 27.8 mmol) was added slowly and the system was reacted at 0° C. for 1 h. The reaction was quenched by adding methanol (10 mL). The mixture was purified by silica gel column chromatography with eluent system A to obtain the target compound 1d (400 mg, 55.8% yield).

MS m/z (ESI): 249.0 [M+1].

Step 3

(R)-4-(7-chloro-1-methyl-1H-pyrazolo[4,3-b]pyridin-5-yl)-3-methylmorpholine 1e

Compound 1d (400 mg, 1.6 mmol) was dissolved in 3.0 mL of phosphorus oxychloride. The system was heated to 90° C. and stirred for 2.0 h. The reaction mixture was cooled to room temperature and concentrated at reduced pressure. The residue was diluted with dichloromethane (50 mL), and cooled in an ice/water bath. Saturated sodium bicarbonate solution was added to neutralize the dilution to pH 8 to 9. The system was stirred for 0.5 h for reaction and let stand for separation. The organic phase was collected, washed with saturated brine (50 mL), dried over anhydrous sodium sulfate and filtered. The filtrate was purified by silica gel column chromatography with eluent system C to obtain the target compound 1e (240 mg, 56% yield).

MS m/z (ESI): 267.0 [M+1].

Step 4

(R)-2-methyl-2-(1-methyl-5-(3-methylmorpholinyl)-1H-pyrazolo[4,3-b]pyridin-7-yl)propane nitrile 1g Compound 1e (240 mg, 0.91 mmol) and compound isobutyronitrile 1f (620 mg, 8.9 mmol, Shanghai Bide) were dissolved in 30 mL of tetrahydrofuran in a nitrogen atmosphere and cooled in a dry ice/acetone bath. Lithium bis (trimethylsilyl)amide (8.9 mL, a 1 M solution in tetrahydrofuran, 8.9 mmol) was added dropwise. The system was stirred at a low temperature for 0.5 h, naturally warmed to room temperature and stirred for 1 h. The reaction was quenched with water. The organic phase was washed with saturated brine (50 mL), dried over anhydrous sodium sulfate and filtered. The filtrate was concentrated at reduced pressure, and the residue was purified by silica gel column chromatography with eluent system C to obtain the target compound 1g (200 mg, 74% yield).

MS m/7. (ESI): 300.1 [M+1].

Step 5

(R)-2-(3-bromo-1-methyl-5-(3-methylmorpholinyl)-1H-pyrazolo[4,3-b]pyridin-7-yl)-2-methylpropanenitrile 1h Compound 1g (200 mg, 0.67 mmol) was dissolved in 5 mL of 1,4-dioxane, and a solution of sodium hydroxide (0.66 mL, 2 M, 1.32 mmol) was added. The mixture was cooled in an ice/water bath before bromine (427 mg, 2.67 mmol) was added. The reaction system was stirred at a low temperature for 10 min, naturally warmed to room temperature and stirred for 1 h for reaction. Ethyl acetate was added for dilution. The organic phase was washed with saturated sodium thiosulfate solution and saturated sodium chloride solution, dried over anhydrous sodium sulfate and filtered. The filtrate was concentrated at reduced pressure, and the residue was purified by silica gel column chromatography with eluent system C to obtain the target compound 1h (140 mg, 55% yield).

MS m/z (ESI): 377.9 [M+1].

Step 6

2-methyl-2-(1-methyl-5-((R)-3-methylmorpholinyl)-3-(1-(tetrahydro-2H-pyran-2-yl)-1H-pyrazol-3-yl)-1H-pyrazolo[4,3-b]pyridin-7-yl)propanenitrile 1i Compound 1h (20 mg, 0.05 mmol), tetrakis(triphenylphosphine)palladium(0) (18 mg, 0.015 mmol), sodium carbonate (11 mg, 0.10 mmol) and 1-(tetrahydro-2H-pyran-2-yl)-3-(4,4,5,5-tetramethyl-1,3,2-dioxaborolan-2-yl)-1H-pyrazole (29 mg, 0.10 mmol, Shanghai Bide) were dissolved in 4 mL of ethylene glycol dimethyl ether. 1 mL of water was added. In an argon atmosphere, the reaction system was heated by microwave to 120° C. and reacted for 1 h. The reaction mixture was cooled to room temperature before 20 ml of water was added. Ethyl acetate (20 mL×3) was added for extraction. The organic phases were combined, concentrated at reduced pressure, washed with saturated sodium chloride solution, dried over anhydrous sodium sulfate and filtered. The filtrate was concentrated at reduced pressure, and the residue was purified by silica gel column chromatography with eluent system C to obtain the target compound 1i (20 mg, 84% yield).

MS m/z. (ESI): 450.1 [M+1].

Step 7

(R)-2-methyl-2-(1-methyl-5-(3-methylmorpholinyl)-3-(1H-pyrazol-3-yl)-1H-pyrazolo[4,3-b]pyridin-7-yl) propanenitrile 1

Compound 1i (20 mg, 0.04 mmol) was dissolved in 5 mL of dichloromethane. 5 mL of trifluoroacetic acid was added dropwise before the reaction system was stirred for 4 h for reaction. The reaction mixture was concentrated at reduced pressure and adjusted to pH 8 to 9 by dropwise adding a 7 M solution of ammonia in methanol. The resulting mixture was concentrated at reduced pressure, and the residue was purified by silica gel column chromatography with eluent system A to obtain the target compound 1 (7.0 mg, 43% yield).

MS m/z (ESI): 366.0 [M+1].

$^1$H NMR (400 MHz, $CD_3OD$): δ 7.58 (s, 1H), 7.03 (s, 1H), 6.86 (s, 1H), 4.39 (s, 4H), 4.04-3.82 (m, 2H), 3.74 (s, 2H), 3.58 (td, 1H), 3.26 (dd, 1H), 1.88 (d, 6H), 1.19 (d, 3H).

Example 2

(R)-1-(1-methyl-5-(3-methylmorpholinyl)-3-(1H-pyrazol-3-yl)-1H-pyrazolo[4,3-b]pyridin-7-yl)cyclopropanenitrile 2

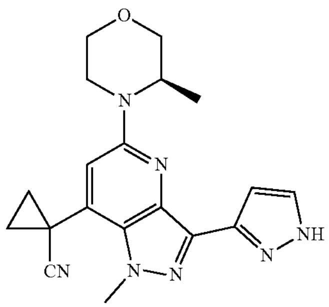

2

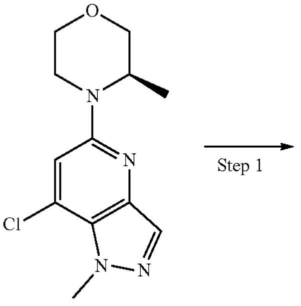

1e

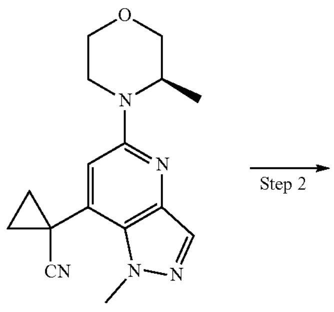

2a

-continued

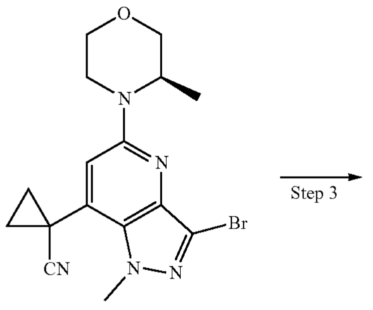

2b

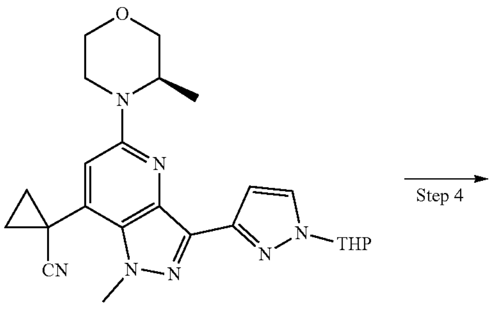

2c

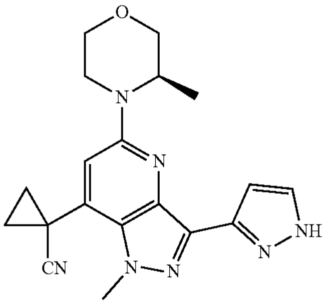

2

Step 1

(R)-1-(1-methyl-5-(3-methylmorpholinyl)-1H-pyrazolo[4,3-b]pyridin-7-yl) cyclopropanenitrile 2a Compound 1e (86 mg, 0.32 mmol), cyclopropanenitrile (65 mg, 0.97 mmol), tris(dibenzylideneacetone)dipalladium (0) (30 mg, 0.03 mmol) and 1,1'-binaphthyl-2,2'-bis-diphenylphosphine (40 mg, 0.06 mmol) were dissolved in 2 mL of tetrahydrofuran. In an argon atmosphere, lithium bis (trimethylsilyl)amide (1.0 mL, a 1 M solution in tetrahydrofuran, 1.0 mmol) was added. The reaction mixture was sealed, heated to 80° C., stirred for 1 h and cooled to room temperature. 20 mL of water was added. Ethyl acetate (20 mL×3) was added for extraction. The organic phases were combined, washed with saturated sodium chloride solution, dried over anhydrous sodium sulfate and filtered. The filtrate was concentrated at reduced pressure, and the residue was purified by silica gel column chromatography with eluent system C to obtain the target compound 2a (80 mg, 84% yield).

MS m/z (ESI): 298.3 [M+1].

Step 2

(R)-1-(3-bromo-1-methyl-5-(3-methylmorpholinyl)-1H-pyrazolo[4,3-b]pyridin-7-yl) cyclopropanenitrile 2b Compound 2a (30 mg, 0.1 mmol) was dissolved in 5 mL of 1,4-dioxane, and a solution of sodium hydroxide (0.1 mL, 2 M, 0.2 mmol) was added. The mixture was cooled in an ice/water bath before bromine (64 mg, 0.4 mmol) was added. The reaction system was stirred at a low temperature for 10 min, naturally warmed to room temperature and stirred for 1 h for reaction. 20 mL of ethyl acetate was added for dilution. The organic phase was washed with saturated sodium thiosulfate solution and saturated sodium chloride solution, dried over anhydrous sodium sulfate and filtered. The filtrate was concentrated at reduced pressure, and the residue was purified by silica gel column chromatography with eluent system C to obtain the target compound 2b (30 mg, 80% yield).

MS m/z (ESI): 376.4 [M+1].

Step 3

1-(1-methyl-5-((R)-3-methylmorpholinyl)-3-(1-(tetrahydro-2H-pyran-2-yl)-1H-pyrazol-3-yl)-1H-pyrazolo[4,3-b]pyridin-7-yl) cyclopropanenitrile 2c Compound 2b (30 mg, 0.08 mmol), tetrakis(triphenylphosphine)palladium(0) (10 mg, 0.08 mmol), sodium carbonate (17 mg, 0.16 mmol) and 1-(tetrahydro-2H-pyran-2-yl)-3-(4,4,5,5-tetramethyl-1,3,2-dioxaborolan-2-yl)-1H-pyrazole (44 mg, 0.16 mmol) were dissolved in 4.0 mL of ethylene glycol dimethyl ether. 1.0 mL of water was added. In an argon atmosphere, the reaction system was heated by microwave to 120° C., stirred for 1 h for reaction and cooled to room temperature. 20 mL of water was added. Ethyl acetate (20 mL×3) was added for extraction. The organic phases were combined, concentrated at reduced pressure, washed with saturated sodium chloride solution, dried over anhydrous sodium sulfate and filtered. The filtrate was concentrated at reduced pressure, and the residue was purified by silica gel column chromatography with eluent system C to obtain the target compound 2c (30 mg, 84% yield).

MS m/z (ESI): 448.3 [M+1].

Step 4

(R)-1-(1-methyl-5-(3-methylmorpholinyl)-3-(1H-pyrazol-3-yl)-1H-pyrazolo[4,3-b]pyridin-7-yl) cyclopropanenitrile 2

Compound 2c (30 mg, 0.07 mmol) was dissolved in 5 mL of dichloromethane. 1 mL of trifluoroacetic acid was added dropwise before the reaction system was stirred for 4 h for reaction. The reaction mixture was concentrated at reduced pressure and adjusted to pH 8 to 9 by dropwise adding a 7 M solution of ammonia in methanol. The resulting mixture was concentrated at reduced pressure, and the residue was purified by silica gel column chromatography with eluent system A to obtain the target compound 2 (13.5 mg, 55% yield).

MS m/z (ESI): 364.3 [M+1].

$^1$H NMR (400 MHz, $CD_3OD$): δ 7.58 (d, 1H), 7.01 (d, 1H), 6.93 (s, 1H), 4.40 (d, 1H), 4.38 (s, 3H), 3.95 (dd, 2H), 3.79-3.68 (m, 2H), 3.57 (td, 1H), 3.30-3.25 (m, 1H), 1.92-1.80 (m, 2H), 1.72-1.58 (m, 2H), 1.18 (d, 3H).

Example 3

(R)-3-methyl-4-(1-methyl-7-(1-methyl-1H-pyrazol-5-yl)-3-(1H-pyrazol-3-yl)-1H-pyrazolo[4,3-b]pyridin-5-yl) morpholine 3

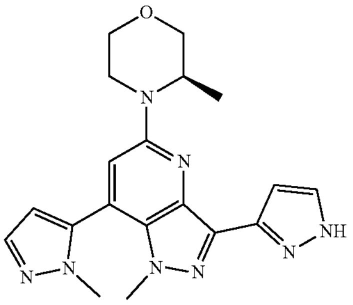

3

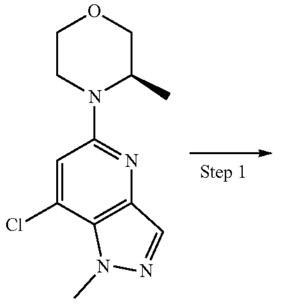

1e

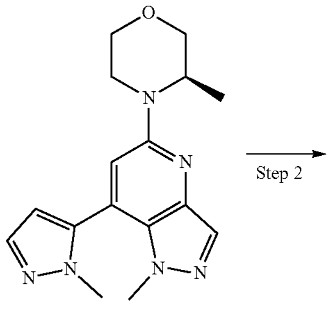

3a

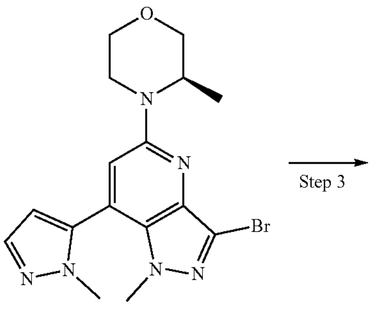

3b

-continued

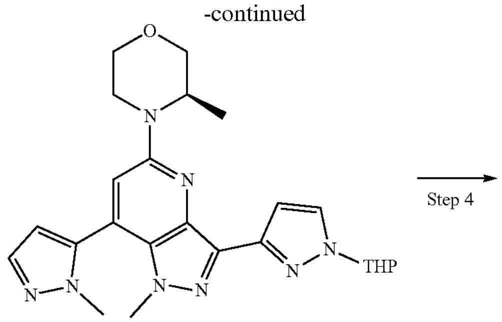

3c

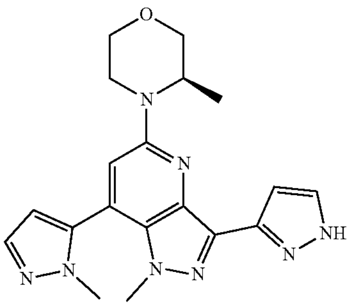

3

Step 1

(R)-3-methyl-4-(1-methyl-7-(1-methyl-1H-pyrazol-5-yl)-1H-pyrazolo[4,3-b]pyridin-5-yl) morpholine 3a Compound 1e (250 mg, 0.94 mmol), bis(triphenylphosphine)palladium(II) dichloride (66 mg, 0.09 mmol), potassium carbonate (260 mg, 1.8 mmol) and 1-methyl-5-(4,4,5,5-tetramethyl-1,3,2-dioxaborolan-2-yl)-1H-pyrazole (390 mg, 1.87 mmol) were dissolved in 8.0 mL of ethylene glycol dimethyl ether. 2.0 mL of water was added. In an argon atmosphere, the reaction system was heated by microwave to 120° C., reacted for 2 h and cooled to room temperature. 20 mL of water was added for dilution. Ethyl acetate (20 mL×3) was added for extraction. The organic phases were combined, washed with saturated sodium chloride solution, dried over anhydrous sodium sulfate and filtered. The filtrate was concentrated at reduced pressure, and the residue was purified by silica gel column chromatography with eluent system C to obtain the target compound 3a (290 mg, 99% yield).

MS m/z (ESI): 313.2 [M+1].

Step 2

(R)-4-(3-bromo-1-methyl-7-(1-methyl-1H-pyrazol-5-yl)-1H-pyrazolo[4,3-b]pyridin-5-yl)-3-methylmorpholine 3b Compound 3a (300 mg, 0.97 mmol) was dissolved in 5 mL of N,N-dimethylformamide and cooled in an ice/water bath. N-bromosuccinimide (205 mg, 1.2 mmol) was added. The mixture was stirred at a low temperature for 10 min, naturally warmed to room temperature and stirred for 1 h. 20 mL of ethyl acetate was added for dilution. The organic phase was washed with saturated sodium thiosulfate solution and saturated sodium chloride solution, dried over anhydrous sodium sulfate and filtered. The filtrate was concentrated at reduced pressure, and the residue was purified by silica gel column chromatography with eluent system C to obtain the target compound 3b (115 mg, 30% yield).

MS m/z (ESI): 391.1 [M+1].

Step 3

(3R)-3-methyl-4-(1-methyl-7-(1-methyl-1H-pyrazol-5-yl)-3-(1-(tetrahydro-2H-pyran-2-yl)-1H-pyrazol-3-yl)-1H-pyrazolo[4,3-b]pyridin-5-yl) morpholine 3c Compound 3b (35 mg, 0.09 mmol), tetrakis(triphenylphosphine)palladium(0) (10 mg, 0.009 mmol), sodium carbonate (19 mg, 0.18 mmol) and 1-(tetrahydro-2H-pyran-2-yl)-3-(4,4,5,5-tetramethyl-1,3,2-dioxaborolan-2-yl)-1H-pyrazole (50 mg, 0.18 mmol) were dissolved in 5.0 mL of ethylene glycol dimethyl ether. 1 mL of water was added. In an argon atmosphere, the reaction system was heated by microwave to 120° C., reacted for 1 h and cooled. 20 mL of water was added. Ethyl acetate (20 mL×3) was added for extraction. The organic phases were combined, washed with saturated sodium chloride solution, dried over anhydrous sodium sulfate and filtered. The filtrate was concentrated at reduced pressure, and the residue was purified by silica gel column chromatography with eluent system C to obtain the target compound 3c (20 mg, 48% yield).

MS m/z (ESI): 463.4 [M+1].

Step 4

(R)-3-methyl-4-(1-methyl-7-(1-methyl-1H-pyrazol-5-yl)-3-(1H-pyrazol-3-yl)-1H-pyrazolo[4,3-b]pyridin-5-yl) morpholine 3

Compound 3c (60 mg, 0.13 mmol) was dissolved in 5 mL of dichloromethane. 1 mL of trifluoroacetic acid was added dropwise before the reaction system was stirred for 4 h for reaction. The reaction mixture was concentrated at reduced pressure and adjusted to pH 8 to 9 by dropwise adding a 7 M solution of ammonia in methanol. The resulting mixture was concentrated at reduced pressure, and the residue was purified by silica gel column chromatography with eluent system A to obtain the target compound 3 (20 mg, 40.7% yield).

MS m/z (ESI): 379.2 [M+1].

$^1$H NMR (400 MHz, $CD_3OD$): δ 7.58 (d, 1H), 7.57 (d, 1H), 7.03 (d, 1H), 6.90 (s, 1H), 6.48 (d, 1H), 4.38 (d, 1H), 4.02-3.88 (m, 2H), 3.72 (s, 2H), 3.65 (s, 3H), 3.57 (td, 1H), 3.50 (s, 3H), 3.27-3.22 (m, 1H), 1.19 (d, 3H).

Example 4

(R)-2-(1-ethyl-5-(3-methylmorpholinyl)-3-(1H-pyrazol-3-yl)-1H-pyrazolo[4,3-b]pyridin-7-yl)-2-methylpropanenitrile 4

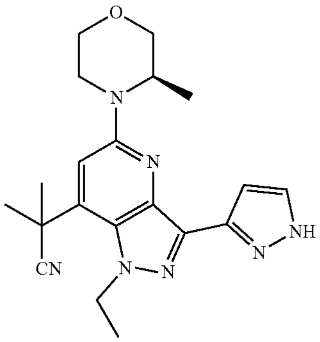

4

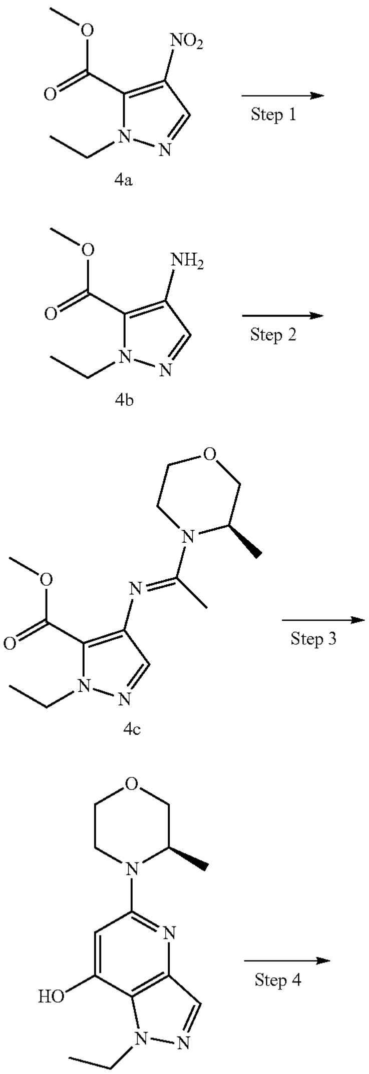

4a

4b

4c

4d

-continued

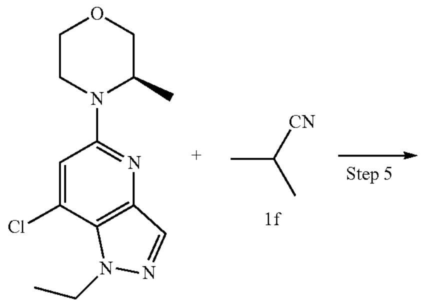

1f

4e

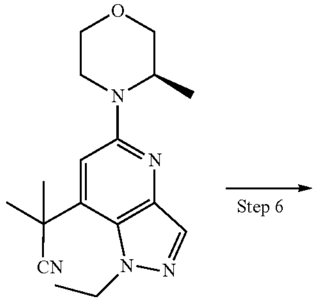

4g

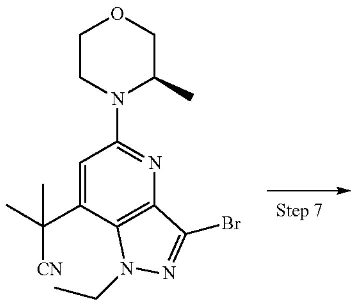

4h

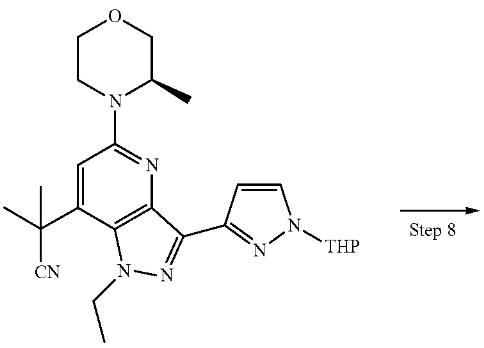

4i

-continued

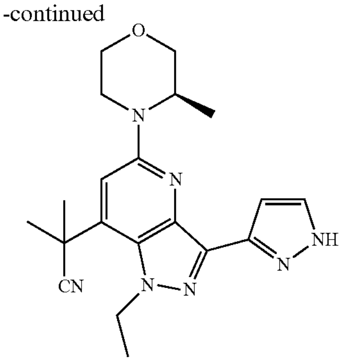

4

Step 1

Methyl 1-ethyl-4-nitro-1H-pyrazole-5-carboxylate 4b

Compound methyl 1-ethyl-4-nitro-1H-pyrazole-5-carboxylate 4a (5 g, 25.1 mmol, Shanghai Bide) was dissolved in 100 mL of methanol. 10% palladium on carbon (1 g) was added. The system was purged with hydrogen three times and stirred for 14 h. The mixture was filtered and the filtrate was concentrated at reduced pressure to obtain a crude product of the target compound 4b (4.2 g), which was used directly in the next reaction without purification.

MS m/z (ESI): 170.1 [M+1].

Step 2

Methyl (R,E)-1-ethyl-4-((1-(3-methylmorpholino) ethylidene)amino)-1H-pyrazole-5-carboxylate 4c Compound 1b (3.3 g, 23.0 mmol) was dissolved in 1,2-dichloroethane and cooled in an ice/water bath in an argon atmosphere. Phosphorus oxychloride (5.4 g, 35.2 mmol) was dropwise and slowly added. The mixture was stirred at room temperature for 30 min before compound 4b (2.5 g, 16.1 mmol) was added. The mixture was heated to 80° C. and stirred for reaction for 2 h. The mixture was cooled to room temperature and concentrated at reduced pressure. The residue was diluted with dichloromethane (200 mL), and cooled in an ice/water bath. Saturated sodium bicarbonate solution was added dropwise to neutralize the dilution to pH 8 to 9. The organic phase was washed with saturated brine (50 mL), dried over anhydrous sodium sulfate and filtered. The filtrate was purified by silica gel column chromatography with eluent system C to give the target compound 4c (2.3 g, 66.1% yield).

MS m/z (ESI): 295.2 [M+1].

Step 3

(R)-1-ethyl-5-(3-methylmorpholinyl)-1H-pyrazolo [4,3-b]pyridin-7-ol 4d

Compound 4c (1 g, 3.39 mmol) was dissolved in tetrahydrofuran (20 mL) and cooled in an ice/water bath. Lithium bis(trimethylsilyl)amide (10 mL, a 1 M solution in tetrahydrofuran, 10 mmol) was added slowly and the system was reacted at 0° C. for 1 h. The reaction was quenched by adding methanol (10 mL). The mixture was purified by silica gel column chromatography with eluent system A to give the target compound 4d (250 mg, 28.1% yield).

MS m/z (ESI): 263.1 [M+1].

Step 4

(R)-4-(7-chloro-1-ethyl-1H-pyrazolo[4,3-b]pyridin-5-yl)-3-methylmorpholine 4e

Compound 4d (250 mg, 0.95 mmol) was dissolved in 2.0 mL of phosphorus oxychloride. The system was heated to 90° C. and stirred for 2 h. The reaction mixture was cooled to room temperature and concentrated at reduced pressure. The residue was diluted with dichloromethane (50 mL), and cooled in ice water. Saturated sodium bicarbonate solution was added to neutralize the dilution to pH 8 to 9. The system was stirred for 0.5 h for reaction and let stand for separation. The organic phase was collected and washed with saturated brine (50 mL), dried over anhydrous sodium sulfate and filtered. The filtrate was purified by silica gel column chromatography with eluent system C to give the target compound 4e (120 mg, 42.5% yield).

MS m/z (ESI): 281.3 [M+1].

Step 5

(R)-2-(1-ethyl-5-(3-methylmorpholinyl)-1H-pyrazolo[4,3-b]pyridin-7-yl)-2-methylpropanenitrile 4g Compound 4e (120 mg, 0.43 mmol) and compound 1f (295 mg, 4.3 mmol, Shanghai Bide) were dissolved in 30 mL of tetrahydrofuran and cooled in a dry ice/acetone bath in an argon atmosphere. Lithium bis(trimethylsilyl)amide (1.7 mL, a 1 M solution in tetrahydrofuran, 1.7 mmol) was added dropwise. The system was stirred at a low temperature for 0.5 h, naturally warmed to room temperature and stirred for 1 h. The reaction was quenched with water. The organic phase was washed with saturated brine (50 mL), dried over anhydrous sodium sulfate and filtered. The filtrate was concentrated at reduced pressure, and the residue was purified by silica gel column chromatography with eluent system C to obtain the target compound 4g (95 mg, 74% yield).

MS m/z (ESI): 314.1 [M+1].

Step 6

(R)-2-(3-bromo-1-ethyl-5-(3-methylmorpholinyl)-1H-pyrazolo[4,3-b]pyridin-7-yl)-2-methylpropanenitrile 4h Compound 4g (95 mg, 0.67 mmol) was dissolved in 5 mL of 1,4-dioxane, and a solution of sodium hydroxide (0.3 mL, 2 M, 0.6 mmol) was added. The mixture was cooled in an ice/water bath before bromine (194 mg, 1.2 mmol) was added. The reaction system was stirred at a low temperature for 10 min, naturally warmed to room temperature and stirred for 1 h for reaction. Ethyl acetate was added for dilution. The organic phase was washed with saturated sodium thiosulfate solution and saturated sodium chloride solution, dried over anhydrous sodium sulfate and filtered. The filtrate was concentrated at reduced pressure, and the residue was purified by silica gel column chromatography with eluent system C to obtain the target compound 4h (41 mg, 34% yield).

MS m/z. (ESI): 392.1 [M+1].

Step 7

2-(1-ethyl-5-((R)-3-methylmorpholinyl)-3-(1-(tetrahydro-2H-pyran-2-yl)-1H-pyrazol-3-yl)-1H-pyrazolo[4,3-b]pyridin-7-yl)-2-methylpropanenitrile 4i Compound 4h (40 mg, 0.1 mmol), tetrakis(triphenylphosphine)palladium(0) (12 mg, 0.01 mmol), sodium carbonate (32 mg, 0.3 mmol) and 1-(tetrahydro-2H-pyran-2-yl)-3-(4,4,5,5-tetramethyl-1,3,2-dioxaborolan-2-yl)-1H-pyrazole (32 mg, 0.20 mmol, Shanghai Bide) were dissolved in 4 mL of dioxane. 1 mL of water was added. In an argon atmosphere, the reaction system was heated by microwave to 120° C. and reacted for 1 h. The reaction mixture was cooled to room temperature before 20 ml of water was added. Ethyl acetate (20 mL×3) was added for extraction. The organic phases were combined, concentrated at reduced pressure, washed with saturated sodium chloride solution, dried over anhydrous sodium sulfate and filtered. The filtrate was concentrated at reduced pressure, and the residue was purified by silica gel column chromatography with eluent system C to obtain the target compound 4i (40 mg, 85% yield).

MS m/z. (ESI): 464.1 [M+1].

Step 8

(R)-2-(1-ethyl-5-(3-methylmorpholinyl)-3-(1H-pyrazol-3-yl)-1H-pyrazolo[4,3-b]pyridin-7-yl)-2-methylpropanenitrile 4

Compound 4i (20 mg, 0.04 mmol) was dissolved in 5 ml of dichloromethane. 5 mL of trifluoroacetic acid was added dropwise before the reaction system was stirred for 4 h for reaction. The reaction mixture was concentrated at reduced pressure and adjusted to pH 8 to 9 by dropwise adding a 7 M solution of ammonia in methanol. The resulting mixture was concentrated at reduced pressure, and the residue was purified by silica gel column chromatography with eluent system A to obtain the target compound 4 (15 mg, 45% yield).

MS m/z (ESI): 380.2 [M+1].

$^1$H NMR (400 MHz, $CD_3OD$): δ 7.57 (s, 1H), 7.04 (s, 1H), 6.85 (s, 1H), 4.66-4.64 (m, 2H), 4.39-4.38 (m, 1H), 3.97-3.91 (m, 2H), 3.74 (s, 2H), 3.58-3.57 (m, 1H), 3.28-3.27 (m, 1H), 1.86 (d, 6H), 1.46 (t, 3H), 1.18 (d, 3H).

Example 5

(R)-1-(1-ethyl-5-(3-methylmorpholinyl)-3-(1H-pyrazol-3-yl)-1H-pyrazolo[4,3-b]pyridin-7-yl) cyclopropanenitrile 5

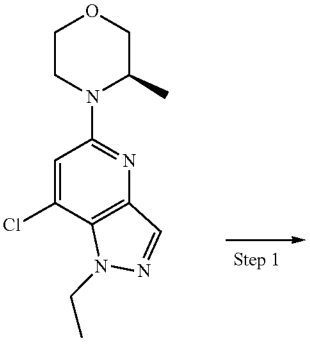

4e

-continued

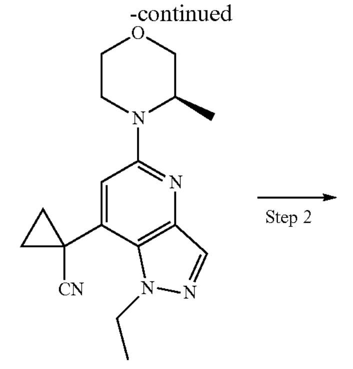

5a

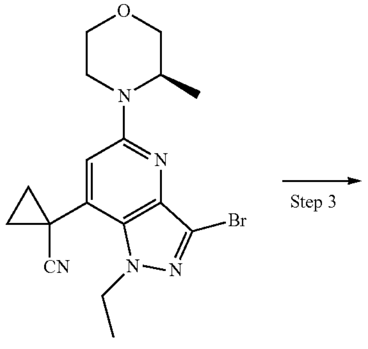

5b

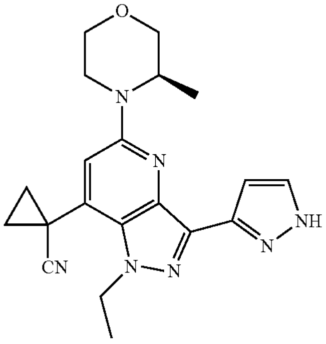

5

Step 1

(R)-1-(1-ethyl-5-(3-methylmorpholinyl)-1H-pyrazolo[4,3-b]pyridin-7-yl) cyclopropanenitrile 5a Compound 4e (500 mg, 1.78 mmol), cyclopropanenitrile (239 mg, 3.56 tris(dibenzylideneacetone)dipalladium(0) (162 mg, 0.18 mmol) and mmol), 1,1'-binaphthyl-2,2'-bis-diphenylphosphine (222 mg, 0.36 mmol) were dissolved in 2 mL of tetrahydrofuran. In an argon atmosphere, lithium bis(trimethylsilyl)amide (5.3 mL, a 1 M solution in tetrahydrofuran, 5.3 mmol) was added. The reaction mixture was sealed, heated to 80° C., stirred for 1 h and cooled to room temperature. 20 mL of water was added. Ethyl acetate (20 mL×3) was added for extraction. The organic phases were combined, washed with saturated sodium chloride solution, dried over anhydrous sodium sulfate and filtered. The filtrate was concentrated at reduced pressure, and the residue was purified by silica gel column chromatography with eluent system C to obtain the target compound 5a (360 mg, 64.9% yield).

MS m/z (ESI): 312.2 [M+1].

Step 2

(R)-1-(3-bromo-1-ethyl-5-(3-methylmorpholinyl)-1H-pyrazolo[4,3-b]pyridin-7-yl) cyclopropanenitrile 5b Compound 5a (377 mg, 1.2 mmol) was dissolved in 5 mL of tetrahydrofuran and cooled in an ice/water bath. N-bromosuccinimide (215 mg, 1.2 mmol) was added. The mixture was stirred at a low temperature for 10 min, naturally warmed to room temperature and stirred for 2 h. 20 mL of ethyl acetate was added for dilution. The organic phase was washed with saturated sodium thiosulfate solution and saturated sodium chloride solution, dried over anhydrous sodium sulfate and filtered. The filtrate was concentrated at reduced pressure, and the residue was purified by silica gel column chromatography with eluent system C to obtain the target compound 5b (100 mg, 21% yield).

MS m/z (ESI): 390.3 [M+1].

Step 3

(R)-1-(1-ethyl-5-(3-methylmorpholinyl)-3-(1H-pyrazol-3-yl)-1H-pyrazolo[4,3-b]pyridin-7-yl) cyclopropanenitrile 5

Compound 5b (100 mg, 0.25 mmol), [1,1'-bis(diphenylphosphino)ferrocene]palladium(II) dichloride dichloromethane complex (43 mg, 0.05 mmol), sodium carbonate (81 mg, 0.78 mmol) and (1H-pyrazol-3-yl) boronic acid (43 mg, 0.38 mmol, Shanghai Bide) were dissolved in 4.0 mL of dioxane. 1.0 mL of water was added. In an argon atmosphere, the reaction system was stirred at 100° C. for 2 h and cooled to room temperature. 20 mL of water was added. Ethyl acetate (20 mL×3) was added for extraction. The organic phases were combined, washed with saturated sodium chloride solution, dried over anhydrous sodium sulfate and filtered. The filtrate was concentrated at reduced pressure, and the residue was purified by silica gel column chromatography with eluent system A to obtain the target compound 5 (10 mg, 10% yield).

$^1$H NMR (400 MHz, $CD_3OD$): δ 7.82 (s, 1H), 7.04-7.12 (m, 2H), 4.84-4.82 (m, 2H), 4.51-4.50 (m, 1H), 4.09-4.05 (m, 2H), 3.86-3.85 (m, 2H), 3.69-3.66 (m, 1H), 3.43-3.42 (m, 1H), 1.97 (d, 2H), 1.80-1.78 (m, 2H), 1.67 (t, 3H), 1.32 (d, 3H).

Example 6

(R)-2-methyl-2-(5-(3-methylmorpholinyl)-3-(1H-pyrazol-3-yl)-1H-pyrazolo[4,3-b]pyridin-7-yl)propanenitrile 6

6

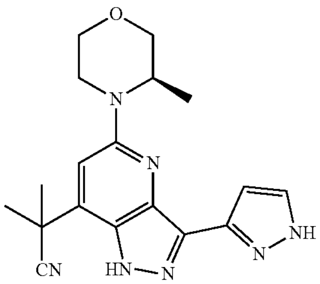

-continued
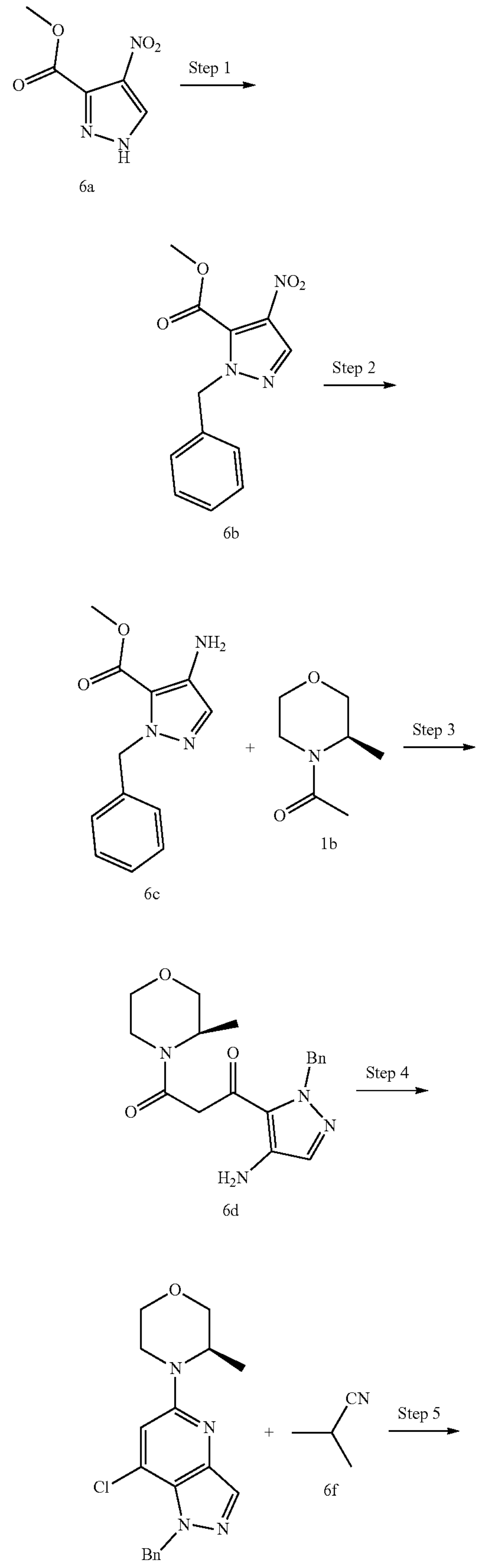
6a
6b
6c
1b
6d
6e
6f
-continued
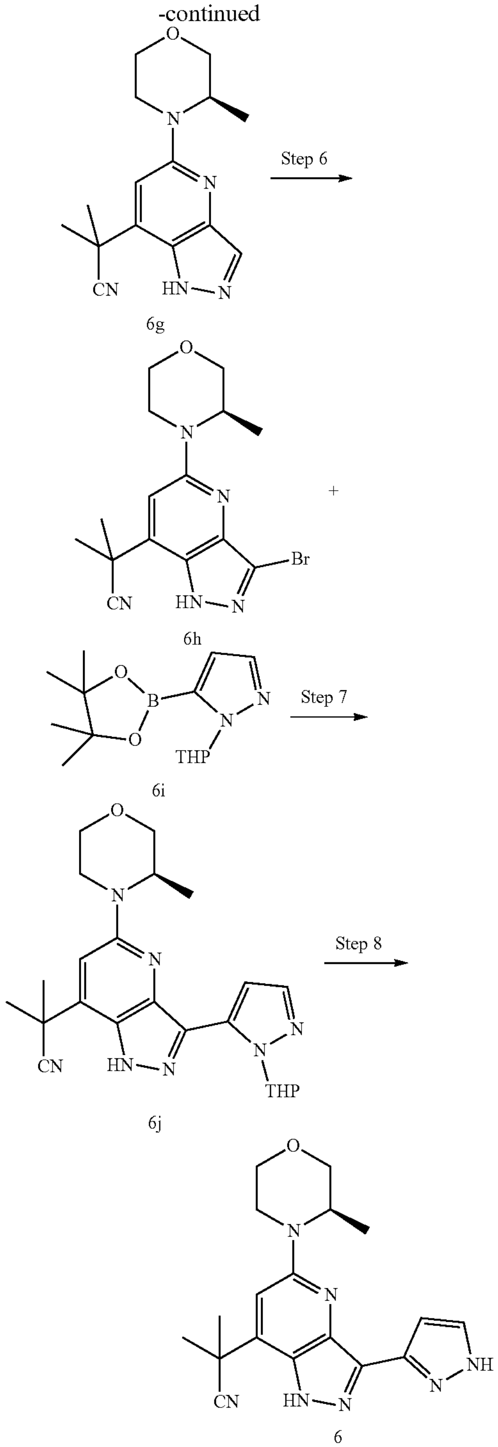
6g
6h
6i
6j
6
Step 1
Methyl 1-benzyl-4-nitro-1H-pyrazole-5-carboxylate 6b
Methyl 4-nitro-1H-pyrazole-3-carboxylate 6a (2 g, 11.69 mmol, Meryer) was dissolved in 30 mL of N,N-dimethylformamide. Potassium carbonate (1.75 g, 12.66 mmol) and benzyl bromide (2.04 g, 11.93 mmol) were added. The mixture was stirred at room temperature for 17 h. 80 mL of ethyl acetate was added to the reaction mixture, which was then washed with water (30 mL×3) and saturated sodium chloride solution (30 mL), dried over anhydrous sodium sulfate and filtered. The filtrate was concentrated at reduced pressure, and the residue was purified by silica gel column chromatography with eluent system C to obtain the target compound 6b (710 mg, 23.3% yield).

MS m/z (ESI): 262.0 [M+1].

Step 2

Methyl 4-amino-1-benzyl-1H-pyrazole-5-carboxylate 6c

Compound 6b (710 mg, 2.72 mmol) was dissolved in 20 mL of absolute ethanol, and iron powder (1.52 g, 27.22 mmol) and ammonium chloride (1.46 g, 27.29 mmol) were added. The reaction system was heated at reflux and stirred for 17 h. The reaction mixture was cooled to room temperature, and filtered through a Buchner funnel pre-layered with celite. The solid was washed with ethyl acetate, and the combined filtrates were concentrated at reduced pressure, and the residue was purified by silica gel column chromatography with eluent system C to obtain the target compound 6c (650 mg, containing ethanol transesterification products, 100% yield).

MS m/z (ESI): 232.2 [M+1], 246.2 [M+1].

Step 3

(R)-1-(4-amino-1-benzyl-1H-pyrazol-5-yl)-3-(3-methylmorpholinyl)propane-1,3-dione 6d Lithium bis(trimethylsilyl)amide (11.29 mL, a 1 M solution in tetrahydrofuran, 11.29 mmol) was transferred to a three-necked flask. In a nitrogen atmosphere, the mixture was cooled to an internal temperature of −10° C. to 0° C. and a solution of 1b in 2-methyltetrahydrofuran (0.65 g, 4.54 mmol, 1.6 mL) was added dropwise. The system was incubated for reaction for 40 min. A solution of 6c in 2-methyltetrahydrofuran (0.65 g, 2.81 mmol, 2.6 mL) was then added dropwise. The reaction system was incubated for reaction for 1 h. 10 mL of water was added to the reaction mixture. Ethyl acetate (10 mL×3) was added for extraction. The organic phase was dried over anhydrous sodium sulfate and filtered. The filtrate was concentrated at reduced pressure, and the residue was purified by silica gel column chromatography with eluent system C to obtain the target compound 6d (440 mg, 45.7% yield).

MS m/7. (ESI): 343.2 [M+1].

Step 4

(R)-1-benzyl-7-chloro-5-(3-methylmorpholinyl)-1H-pyrazolo[4,3-b]pyridine 6e

Compound 6d (0.44 g, 1.29 mmol) was dissolved in 5 mL of acetonitrile. N,N-diisopropylethylamine (0.5 g, 3.87 mmol) was added. The mixture was cooled to an inner temperature of −5° C. to 0° C. Phosphorus oxychloride (0.79 g, 5.15 mmol) was added dropwise. The system was incubated for reaction for 1.5 h, and reacted at 65° C. for 4 h. The reaction solution was cooled to room temperature and poured into 20 mL of saturated sodium carbonate solution. Ethyl acetate (20 mL×3) was added for extraction. The organic phase was dried over anhydrous sodium sulfate and filtered. The filtrate was concentrated at reduced pressure, and the residue was purified by silica gel column chromatography with eluent system C to obtain the target compound 6e (180 mg, 40.8% yield).

MS m/z (ESI): 343.1 [M+1].

Step 5

(R)-2-methyl-2-(5-(3-methylmorpholinyl)-1H-pyrazolo[4,3-b]pyridin-7-yl)propanenitrile 6g Compound 6e (180 mg, 0.53 mmol) and isobutyronitrile 6f (218 mg, 3.15 mmol) were dissolved in 5 mL of tetrahydrofuran. In a nitrogen atmosphere, the mixture was cooled to an internal temperature of less than −70° C. Lithium bis(trimethylsilyl)amide (3.15 mL, a 1 M solution in tetrahydrofuran, 3.15 mmol) was added dropwise. The system was incubated for 30 min for reaction, and further reacted at room temperature for 1 h. 10 mL of water was added. Ethyl acetate (10 mL×3) was added for extraction. The organic phase was dried over anhydrous sodium sulfate and filtered. The filtrate was concentrated at reduced pressure, and the residue was purified by silica gel column chromatography with eluent system C to obtain the target compound 6g (80 mg, 53.3% yield).

MS m/7. (ESI): 286.2 [M+1].

Step 6

(R)-2-(3-bromo-5-(3-methylmorpholinyl)-1H-pyrazolo[4,3-b]pyridin-7-yl)-2-methylpropanenitrile 6h Compound 6g (80 mg, 0.28 mmol) was dissolved in 2 mL of tetrahydrofuran. N-bromosuccinimide (50 mg, 0.28 mmol) was added. The mixture was stirred at room temperature for 30 min. 10 mL of saturated sodium thiosulfate solution was added. Ethyl acetate (10 mL×3) was added for extraction. The organic phase was dried over anhydrous sodium sulfate and filtered. The filtrate was concentrated at reduced pressure, and the residue was purified by silica gel column chromatography with eluent system C to obtain the target compound 6h (40 mg, 39.2% yield).

MS m/z (ESI): 364.1 [M+1].

Step 7

2-methyl-2-(5-((R)-3-methylmorpholinyl)-3-(1-(tetrahydro-2H-pyran-2-yl)-1H-pyrazol-5-yl)-1H-pyrazolo[4,3-b]pyridin-7-yl)propanenitrile 6j Compound 6h (40 mg, 0.11 mmol), 1-(tetrahydro-2H-pyran-2-yl)-5-(4,4,5,5-tetramethyl-1,3,2-dioxaborolan-2-yl)-1H-pyrazole 6i (61 mg, 0.22 mmol, Shanghai Bide) and sodium carbonate (24 mg, 0.22 mmol) were added to a three-necked flask. 2 mL of 1,4-dioxane and 0.5 mL of water were added. After 3 nitrogen purges, bis(triphenylphosphine)palladium(II) dichloride (16 mg, 22.8 μmol) was added, followed by another 3 nitrogen purges. In a nitrogen atmosphere, the external temperature was raised to 85° C., and the system was stirred for 1 h. The reaction solution was cooled to room temperature before 10 mL of water was added to the reaction mixture. Ethyl acetate (10 mL×3) was added for extraction. The organic phase was dried over anhydrous sodium sulfate and filtered. The filtrate was concentrated at reduced pressure, and the residue was purified by silica gel column chromatography with eluent system C to obtain the target compound 6j (25 mg, 52.3% yield).

MS m/z (ESI): 436.3 [M+1].

Step 8

2-Methyl-2-(5-((R)-3-methylmorpholinyl)-3-(1H-pyrazol-5-yl)-1H-pyrazolo[4,3-b]pyridin-7-yl)propanenitrile 6

Compound 6j (22 mg, 50.51 umol) was dissolved in 3 mL of isopropanol. Trifluoroacetic acid (404 mg, 3.54 mmol) was added. The system was stirred at room temperature for 30 min. The reaction solution was poured into 10 mL of saturated sodium bicarbonate solution. The mixture was concentrated at reduced pressure. Ethyl acetate (10 mL×3) was added for extraction. The organic phase was dried over anhydrous sodium sulfate and filtered. The filtrate was concentrated at reduced pressure, and the residue was purified by thin layer chromatography with developing solvent system C to obtain the target compound 6 (5 mg, 28.2% yield).

MS m/z (ESI): 352.1 [M+1].

$^{1}$H NMR (500 MHz, $CDCl_3$): δ 7.77 (s, 1H), 7.18 (s, 1H), 6.93 (s, 1H), 4.42-4.43 (d, 1H), 4.14-4.11 (m, 1H), 4.01-3.98 (m, 1H), 3.88-3.89 (m, 2H), 3.74-3.67 (m, 1H), 3.44-3.42 (m, 1H), 2.00 (s, 6H), 1.36-1.35 (d, 3H).

Comparative Example 1 (Example 7)

(R)-2-(1-methyl-5-(3-methylmorpholinyl)-3-(1H-pyrazol-3-yl)-1H-pyrazolo[4,3-b]pyridin-7-yl)propan-2-ol 7

7

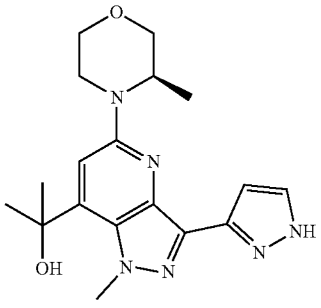

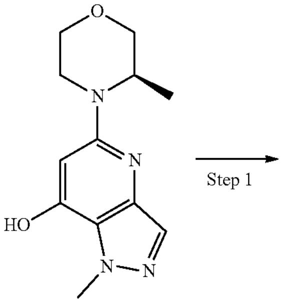

1d

-continued

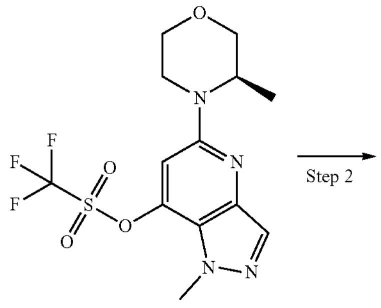

7a

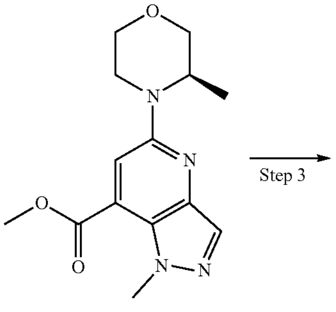

7b

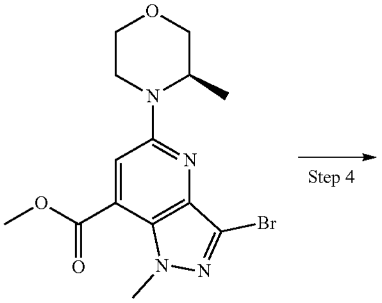

7c

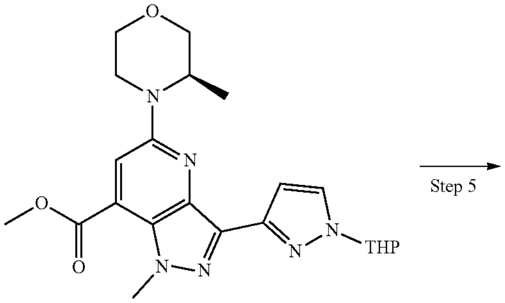

7d

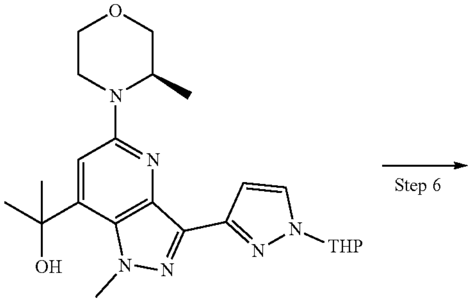

7e

-continued

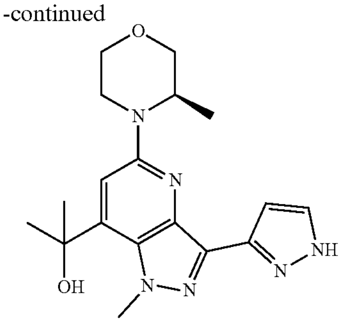

7

Step 1

(R)-1-methyl-5-(3-methylmorpholinyl)-1H-pyrazolo[4,3-b]pyridin-7-yl trifluoromethanesulfonate 7a Compound 1d (500 mg, 2.0 mmol) was dissolved in 5.0 mL of dichloromethane. N,N-diisopropylethylamine (520 mg, 4.0 mmol) and N-phenyl-bis(trifluoromethanesulfonimide) (790 mg, 2.2 mmol) were added. The system was stirred for 2.0 h. The reaction mixture was concentrated at reduced pressure, and the residue was purified by silica gel column chromatography with eluent system C to obtain the target compound 7a (600 mg, 78.3% yield).

MS m/z (ESI): 381.3 [M+1].

Step 2

Methyl (R)-1-methyl-5-(3-methylmorpholinyl)-1H-pyrazolo[4,3-b]pyridine-7-carboxylate 7b Compound 7a (400 mg, 1.05 mmol), [1,1'-bis(diphenylphosphino)ferrocene]palladium(II) dichloride dichloromethane complex (178 mg, 0.21 mmol, Shanghai Bide) and triethylamine (210 mg, 2.09 mmol) were dissolved in 8 mL of methanol. In a carbon monoxide atmosphere, the system was stirred at 65° C. for 15 h. The resulting mixture was cooled to room temperature and filtered. The filtrate was concentrated at reduced pressure, and the residue was purified by silica gel column chromatography with eluent system C to obtain the target compound 7b (90 mg, 29.5% yield).

MS m/z (ESI): 291.1 [M+1].

Step 3

Methyl (R)-3-bromo-1-methyl-5-(3-methylmorpholine)-1H-pyrazolo[4,3-b]pyridine-7-carboxylate 7c Compound 7b (90 mg, 0.31 mmol) was dissolved in 5 mL of tetrahydrofuran. N-bromosuccinimide (110 mg, 0.62 mmol) was added. The mixture was stirred at room temperature for 30 min. 10 mL of saturated sodium thiosulfate solution was added. Ethyl acetate (10 mL×3) was added for extraction. The organic phase was dried over anhydrous sodium sulfate and filtered. The filtrate was concentrated at reduced pressure to obtain a crude product of the target compound 7c (180 mg), which was directly used in the next step without purification.

MS m/z (ESI): 369.1 [M+1].

Step 4

Methyl 1-methyl-5-((R)-3-methylmorpholinyl)-3-(1-(tetrahydro-2H-pyran-2-yl)-1H-pyrazol-3-yl)-1H-pyrazolo[4,3-b]pyridine-7-carboxylate 7d Compound 7c (180 mg, 0.316 mmol), [1,1'-bis(diphenylphosphino)ferrocene]palladium(II) dichloride dichloromethane complex (30 mg, 0.032 mmol), sodium carbonate (83 mg, 0.783 mmol) and 1-(tetrahydro-2H-pyran-2-yl)-3-(4,4,5,5-tetramethyl-1,3,2-dioxaborolan-2-yl)-1H-pyrazole (176 mg, 0.632 mmol, Shanghai Bide) were dissolved in 4 mL of dioxane. 1 mL of water was added. In an argon atmosphere, the reaction system was heated by microwave to 120° C. and reacted for 1 h. The reaction mixture was cooled to room temperature before 20 ml of water was added. Ethyl acetate (20 mL×3) was added for extraction. The organic phases were combined, concentrated at reduced pressure, washed with saturated sodium chloride solution, dried over anhydrous sodium sulfate and filtered. The filtrate was concentrated at reduced pressure, and the residue was purified by silica gel column chromatography with eluent system C to obtain the target compound 7d (45 mg, 32.3% yield).

MS m/z (ESI): 441.2 [M+1].

Step 5

2-(1-methyl-5-((R)-3-methylmorpholinyl)-3-(1-(tetrahydro-2H-pyran-2-yl)-1H-pyrazol-3-yl)-1H-pyrazolo[4,3-b]pyridin-7-yl)propan-2-ol 7e Compound 7d (45 mg, 0.102 mmol) was dissolved in 5 mL of tetrahydrofuran. In an ice bath, a 1 M solution of methylmagnesium bromide in tetrahydrofuran (36 mg, 0.301 mmol, Shanghai Bide) was added dropwise before the reaction system was stirred for 2 h for reaction. 10 mL of saturated ammonium chloride solution was added to the reaction mixture. Ethyl acetate (10 mL×3) was added for extraction. The organic phase was concentrated at reduced pressure, and the residue was purified by silica gel column chromatography with eluent system A to obtain the target compound 7e (40 mg, 88.9% yield).

MS m/z (ESI): 441.6 [M+1].

Step 6

(R)-2-(1-methyl-5-(3-methylmorpholinyl)-3-(1H-pyrazol-3-yl)-1H-pyrazolo[4,3-b]pyridin-7-yl)propan-2-ol 7

Compound 7e (40 mg, 90 umol) was dissolved in 3 mL of methanol. A solution of hydrochloric acid in dioxane (1 mL, 4 N) was added. The system was stirred at room temperature for 30 min. The reaction solution was concentrated at reduced pressure, and the residue was purified by thin layer chromatography with developing solvent system C to obtain the target compound 7 (10 mg, 30.9% yield).

MS m/7. (ESI): 357.6 [M+1].

$^1$H NMR (400 MHz, $CD_3OD$): δ 7.68 (s, 1H), 7.43 (s, 1H), 7.11 (s, 1H), 4.50-4.42 (m, 2H), 4.21 (s, 3H), 4.10-3.99 (m, 4H), 3.84 (d, 2H), 3.68 (td, 2H), 1.28 (d, 6H).

Test Examples

Biological Evaluation

Test Example 1. Inhibitory Effect of Compounds Disclosed Herein on ATR Enzyme The following method was used to determine the inhibitory effect of the compounds disclosed herein on ATR enzyme. The experimental methodology is briefly described as follows:

I. Materials and Instruments

1. ATR enzyme (Eurofins Pharma Discovery Services, 14-953-M)
2. GST-tag P53 protein (Eurofins Pharma Discovery Services, 14-952-M)
3. 384-well plate (Thermo Scientific, 267462)
4. U-shaped bottom 96-well plate (Corning, 3795)
5. MAb Anti-phospho p53-Eu cryptate (Cisbio, 61P08KAE)
6. MAb Anti GST-d2 (Cisbio, 61GSTDLF)
7. ATP solution (Promega, V916B)
8. EDTA (Thermo Scientific, AM9260G)
9. HEPES (Gibco, 15630-080)
10. Microplate reader (BMG, PHERAsta)

II. Procedures 1 nM ATR enzyme, 50 nM P53 protein, 7.435 μM ATP and small molecule compounds of different concentrations (serially 3-fold diluted from 1 μM to the 11th concentration) were mixed and incubated at room temperature for 2 h. A terminating buffer (12.5 mM HEPES, 250 mM EDTA) was added. The mixture was well mixed before 0.42 ng/well of mAb anti-phospho p53-Eu cryptate and 25 ng/well of mAb anti GST-d2 were added. The mixture was incubated overnight at room temperature, and the fluorescence signals at 620 nm and 665 nm were detected using a PHERAstar system. Data were processed using GraphPad software.

III. Experimental Data

The inhibitory activity of the compounds disclosed herein against ATR enzyme can be determined by the above assay, and the $IC_{50}$ values obtained are shown in Table 1.

TABLE 1

$IC_{50}$ for ATR enzyme inhibition by compounds disclosed herein

| i. | Example | ii. | $IC_{50}$/nM | iii. | Maximum inhibition (%) |
|---|---|---|---|---|---|
| iv. | 1 | v. | 3 | vi. | 100 |
| vii. | 2 | viii. | 9 | ix. | 100 |
| x. | 3 | xi. | 15 | xii. | 100 |
| xiii. | 4 | xiv. | 6 | xv. | 100 |
| xvi. | 5 | xvii. | 8 | xviii. | 100 |
| xix. | 6 | xx. | 3 | xxi. | 100 |
| xxii. | Comparative Example 1 | xxiii. | 73 | xxiv. | 97 |

Conclusions: The compounds disclosed herein had superior inhibitory activities against ATR enzyme than that of Comparative Example 1.

Test Example 2. Cell Proliferation Assay

The following method evaluates the inhibitory effect of the compounds disclosed herein on the proliferation of LoVo cells via $IC_{50}$ by measuring the intracellular ATP content. The experimental methodology is briefly described as follows:

I. Materials and Instruments

1. LoVo, human colon cancer cells (Cobioer, Nanjing, CBP60032)
2. Fetal bovine serum (FBS) (Gibco, 10091-148)
3. F-12K Medium (Gibco, 21127030)
4. CellTite-Glo reagent (Promega, G7573)
5. 96-well cell culture plate (Corning, 3903)
6. Pancreatin (Invitrogen, 25200-072)
7. Microplate reader (BMG, PHERAstar)
8. Cell counter (Countstar, Shanghai, IC1000)

II. Procedures

LoVo cells were cultured in an F-12K culture medium containing 10% of FBS, and passaged twice or thrice a week in a passage ratio of 1:3 or 1:5. During passage, cells were digested by pancreatin, transferred to a centrifuge tube, and centrifuged for 3 min at 1200 rpm. The supernatant was discarded, and fresh culture medium was added to resuspend the cells. To a 96-well cell culture plate, 90 μL of the cell suspension was added at a density of $3.88\times10^4$ cells/mL. To peripheral wells of the 96-well plate, only 100 μL of complete medium was added. The plate was incubated in an incubator for 24 h (37° C., 5% $CO_2$).

The test samples were diluted to 2 mM in DMSO and serially 3-fold diluted to the $10^{th}$ concentration. Blank and control wells were set. 5 μL of the serially diluted test compound solutions was added to 95 μL of fresh medium. 10 μL of the medium containing the compound above was added to the plate. The plate was incubated in an incubator for 3 days (37° C., 5% $CO_2$). 50 μL of CellTiter-Glo reagent was added into each well of the 96-well cell culture plate. The plate was let stand for 5-10 min in the dark at room temperature. The chemiluminescence signals were read by a PHERAstar system, and the data were processed by GraphPad software.

III. Experimental Data

The inhibitory activity of the compounds disclosed herein against LoVo cell proliferation can be determined by the above assay, and the $IC_{50}$ values obtained are shown in Table 2.

TABLE 2

$IC_{50}$ for LoVo cell proliferation inhibition by compounds disclosed herein

| Example | $IC_{50}$/nM | Maximum inhibition (%) |
|---|---|---|
| 1 | 43 | 93 |
| 2 | 75 | 90 |
| 3 | 124 | 87 |
| 4 | 64 | 89 |
| 5 | 100 | 93 |
| 6 | 55 | 95 |
| Comparative Example 1 | 316 | 92 |

Conclusions: The compounds disclosed herein had superior inhibitory activities against LoVo cell proliferation than that of Comparative Example 1.

Pharmacokinetic Evaluation

Test Example 3. Pharmacokinetic Study of Compounds Disclosed Herein

1. Introduction

The plasma concentration of the compounds of Examples 1, 2 and 3 in rats after intragastric administration were measured by LC/MS/MS. The pharmacokinetic performance in rats of the compounds disclosed herein was studied and their pharmacokinetic profile was evaluated.

2. Methodology 2.1. Test Compounds

The compounds of Examples 1, 2 and 3.

2.2. Test Animals 12 healthy adult SD rats (half male and half female; purchased from Vital River) were evenly divided into 3 groups of 4.

2.3. Pharmaceutical Formulation

A certain amount of the compound was added to a mixed solvent containing 5% of DMSO, 5% of Tween 80 and 90% of normal saline to obtain a colorless and clear solution.

2.4. Administration

SD rats were intragastrically administered with the compounds after fasting overnight, at a dose of 2 mg/kg and a volume of 10.0 mL/kg.

3. Procedures

Rats were intragastrically administered with the compounds of Examples 1, 2 and 3. 0.2 mL of blood was collected from the orbit pre-dose and at 0.25, 0.5, 1.0, 2.0, 4.0, 6.0, 8.0, 11.0 and 24.0 h post-does. The blood samples were transferred to EDTA-K2kk anticoagulation vacutainers, centrifuged at 4° C. and 11000 rpm for 5 min to separate plasma. The plasma samples were stored at −20° C. The mice were fed 2 h after administration.

The plasma concentration of the compounds in rats after intragastric administration was determined: 25 μL of rat plasma at each time point post-dose was mixed with 50 μL of internal standard and 175 μL of acetonitrile; the mixture was vortexed 5 min, and centrifuged for 10 min at 4000 rpm. 1 μL of supernatant was taken for LC/MS/MS analysis.

4. Pharmacokinetics

TABLE 3

Pharmacokinetics of compounds disclosed herein

| No. | Pharmaceutical study (2 mg/kg)<br>Plasma concentration $C_{max}$ (ng/mL) | Area under curve AUC (ng/mL*h) | Half life $T_{1/2}$ (h) | Retention time MRT (h) | Clearance CL/F (mL/min/kg) | Apparent volume of distribution Vz/F (mL/kg) |
|---|---|---|---|---|---|---|
| 1 | 1112 ± 394 | 3203 ± 2747 | 2.62 ± 2.48 | 3.08 ± 2.31 | 17.7 ± 12.4 | 2058 ± 1222 |
| 2 | 309 ± 219 | 1592 ± 1392 | 2.57 ± 1.39 | 3.99 ± 2.26 | 51.7 ± 49.5 | 7804 ± 6135 |
| 3 | 673.57 ± 86.67 | 2706 ± 807 | 2.23 ± 0.53 | 3.26 ± 0.67 | 13.14 ± 3.7 | 2437 ± 448 |

Conclusions: The compounds disclosed herein demonstrated good absorption profile and significant pharmacokinetic superiority.

The invention claimed is:

1. A compound of formula (I):

(I)

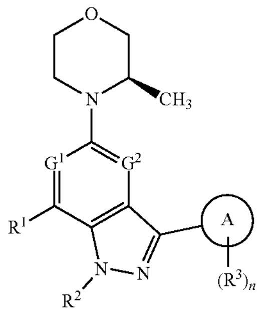

or a pharmaceutically acceptable salt or tautomer thereof, wherein:

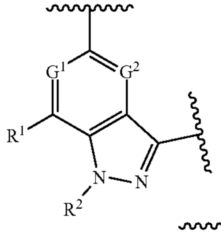

is

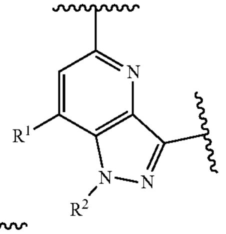

or

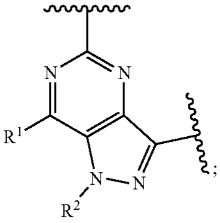

;

$R^1$ is alkyl or cyclopropyl, wherein the alkyl or cyclopropyl is substituted with one or more CN substituents;

$R^2$ is H or alkyl, wherein the alkyl is optionally substituted with one or more substituents independently selected from the group consisting of halogen, CN, $NO_2$, $NH_2$, OH, O(alkyl), cycloalkyl, heterocyclyl, aryl, and heteroaryl;

ring A is pyrazolyl;

each $R^3$ is independently H, halogen, CN, alkyl, alkenyl, $NH_2$, OH, O(alkyl), O(haloalkyl), cycloalkyl, heterocyclyl, aryl, or heteroaryl;

wherein each alkyl and O(alkyl) is optionally and independently substituted with one or more substituents independently selected from the group consisting of halogen, CN, $NO_2$, $NH_2$, OH, O(alkyl), cycloalkyl, heterocyclyl, aryl, and heteroaryl; and wherein each cycloalkyl, heterocyclyl, aryl, and heteroaryl is optionally and independently substituted with one or more substituents independently selected from the group consisting of halogen, CN, $NO_2$, alkyl, haloalkyl, hydroxyalkyl, $NH_2$, OH, O(alkyl), cycloalkyl, heterocyclyl, aryl, and heteroaryl; and n is 0, 1, 2, or 3.

2. The compound according to claim 1, or a pharmaceutically acceptable salt or tautomer thereof, wherein $R^1$ is $C(CH_3)_2CN$ or 1-cyanocyclopropyl.

3. The compound according to claim 1, or a pharmaceutically acceptable salt or tautomer thereof, wherein $R^2$ is H, $CH_3$, or $CH_2CH_3$.

4. The compound according to claim 1, wherein the compound is of formula (II):

(II)

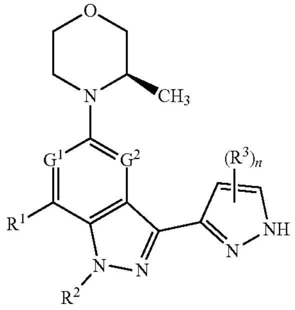

or a pharmaceutically acceptable salt or tautomer thereof.

5. The compound according to claim 1, or a pharmaceutically acceptable salt or tautomer thereof, wherein each $R^3$ is independently H.

6. The compound according to claim 1, wherein the compound is selected from the group consisting of:

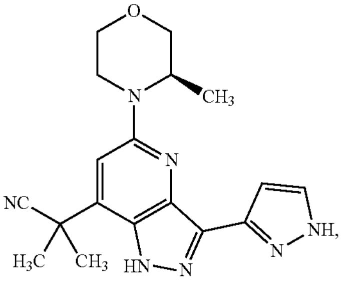 [SMILES: C[C@@H]1COCCN1c1cc(C(C)(C)C#N)c2[nH]nc(-c3cc[nH]n3)c2n1]

-continued

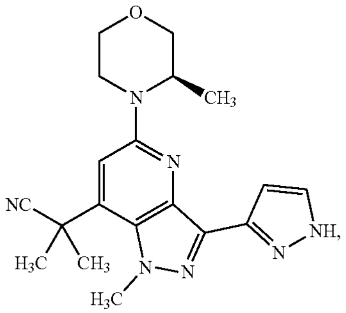

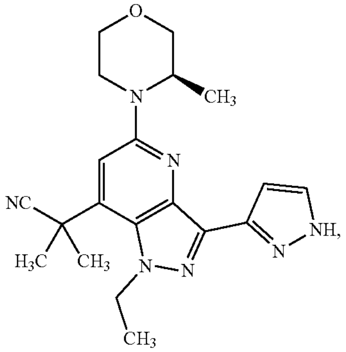

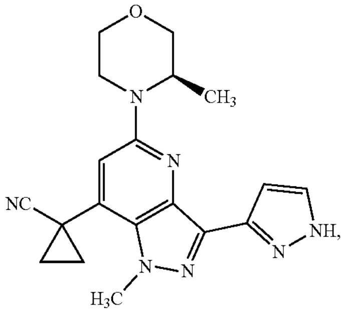

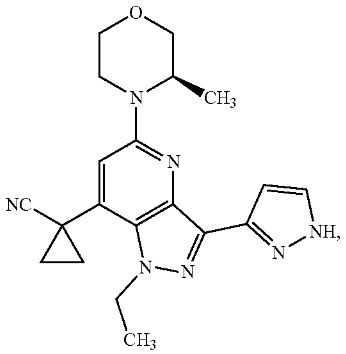

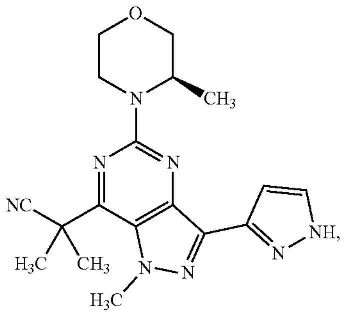 [SMILES: C[C@@H]1COCCN1c1cc(C(C)(C)C#N)c2c(n1)c(-c1cc[nH]n1)nn2C]

and

-continued

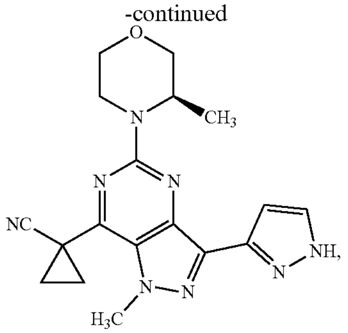

or a pharmaceutically acceptable salt or tautomer thereof.

7. The compound according to claim 6, wherein the compound is:

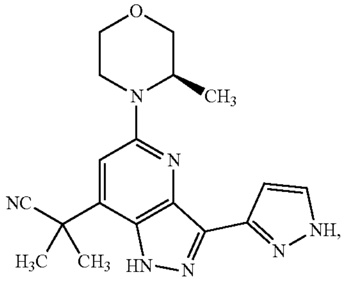

or a pharmaceutically acceptable salt or tautomer thereof.

8. The compound according to claim 6, wherein the compound is:

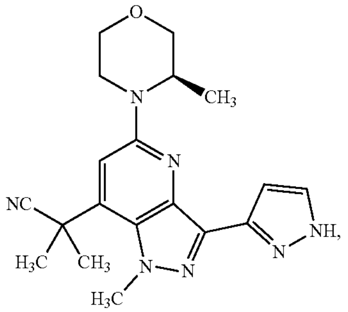

or a pharmaceutically acceptable salt or tautomer thereof.

9. A pharmaceutical composition comprising at least one pharmaceutically acceptable carrier, diluent, or excipient and the compound according to claim 1, or a pharmaceutically acceptable salt or tautomer thereof.

10. A method for inhibiting ataxia-telangiectasia and rad3-related (ATR) kinase activity in a subject in need thereof, wherein the method comprises administering to the subject an effective amount of the pharmaceutical composition according to claim 9.

11. The method according to claim 10, wherein the subject has a cancer.

12. The method according to claim 11, wherein the cancer is selected from the group consisting of B-cell lymphoma, bladder cancer, bone cancer, a brain tumor, breast cancer, cervical cancer, colorectal cancer, endometrial cancer, esophageal cancer, gallbladder cancer, gastric cancer, a head and neck tumor, kidney cancer, leukemia, liver cancer, lung cancer, a melanoma, multiple myeloma, neuroblastoma, neuroglioma, ovarian cancer, pancreatic cancer, prostate cancer, a sarcoma, skin cancer, and a thyroid tumor.

13. The method according to claim 10, wherein the subject has a hyperproliferative disease.

14. A process for preparing a compound of formula (I) according to claim 1:

(I)

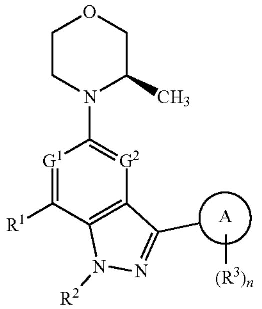

wherein:

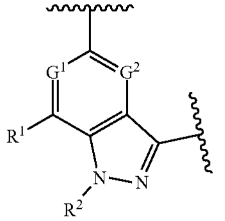

is

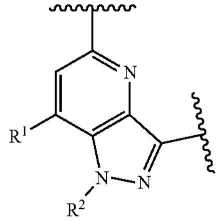

or

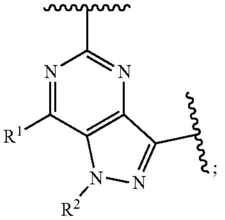

;

$R^1$ is alkyl or cyclopropyl, wherein the alkyl or cyclopropyl is substituted with one or more CN substituents;

$R^2$ is H or alkyl, wherein the alkyl is optionally substituted with one or more substituents independently selected from the group consisting of halogen, CN, $NO_2$, $NH_2$, OH, O(alkyl), cycloalkyl, heterocyclyl, aryl, and heteroaryl;

ring A is pyrazolyl;

each $R^3$ is independently H, halogen, CN, alkyl, alkenyl, $NH_2$, OH, O(alkyl), O(haloalkyl), cycloalkyl, heterocyclyl, aryl, or heteroaryl;

wherein each alkyl and O(alkyl) is optionally and independently substituted with one or more substituents independently selected from the group consisting of halogen, CN, $NO_2$, $NH_2$, OH, O(alkyl), cycloalkyl, heterocyclyl, aryl, and heteroaryl; and wherein each cycloalkyl, heterocyclyl, aryl, and heteroaryl is optionally and independently substituted with one or more substituents independently selected from the group consisting of halogen, CN, $NO_2$, alkyl, haloalkyl, hydroxyalkyl, $NH_2$, OH, O(alkyl), cycloalkyl, heterocyclyl, aryl, and heteroaryl; and n is 0, 1, 2, or 3;

wherein the process comprises the following step:

reacting a compound of formula (IA):

(IA)

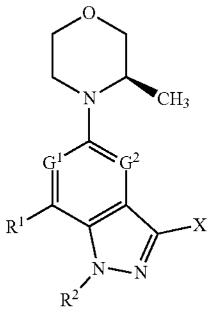

wherein:

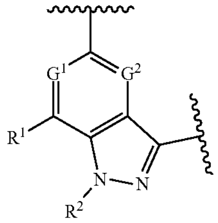

is

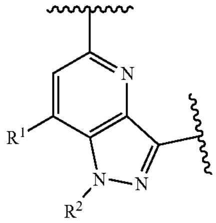

or

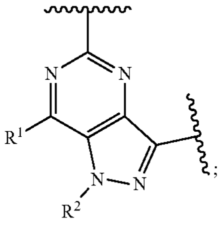

;

$R^1$ is alkyl or cyclopropyl, wherein the alkyl or cyclopropyl is substituted with one or more CN substituents;

$R^2$ is H or alkyl, wherein the alkyl is optionally substituted with one or more substituents independently selected from the group consisting of halogen, CN, $NO_2$, $NH_2$, OH, O(alkyl), cycloalkyl, heterocyclyl, aryl, and heteroaryl; and X is halogen;

with a compound of formula (IB):

(IB)

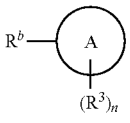

wherein:

ring A is pyrazolyl;

$R^b$ is:

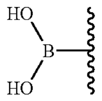

or

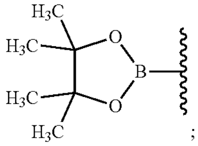

;

each $R^3$ is independently H, halogen, CN, alkyl, alkenyl, $NH_2$, OH, O(alkyl), O(haloalkyl), cycloalkyl, heterocyclyl, aryl, or heteroaryl;

wherein each alkyl and O(alkyl) is optionally and independently substituted with one or more substituents independently selected from the group consisting of halogen, CN, $NO_2$, $NH_2$, OH, O(alkyl), cycloalkyl, heterocyclyl, aryl, and heteroaryl; and wherein each cycloalkyl, heterocyclyl, aryl, and heteroaryl is optionally and independently substituted with one or more substituents independently selected from the group consisting of halogen, CN, $NO_2$, alkyl, haloalkyl, hydroxyalkyl, $NH_2$, OH, O(alkyl), cycloalkyl, heterocyclyl, aryl, and heteroaryl; and n is 0, 1, 2, or 3;

to obtain the compound of formula (I) above.

15. A process for preparing a compound of formula (II) according to claim 4:

(II)

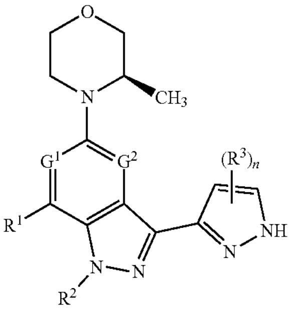

wherein:

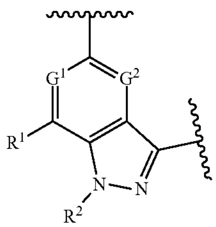

is

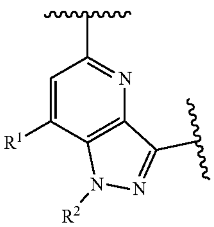

or

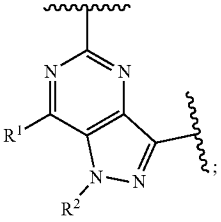

;

$R^1$ is alkyl or cyclopropyl, wherein the alkyl or cyclopropyl is substituted with one or more CN substituents;

$R^2$ is H or alkyl, wherein the alkyl is optionally substituted with one or more substituents independently selected from the group consisting of halogen, CN, $NO_2$, $NH_2$, OH, O(alkyl), cycloalkyl, heterocyclyl, aryl, and heteroaryl;

each $R^3$ is independently H, halogen, CN, alkyl, alkenyl, $NH_2$, OH, O(alkyl), O(haloalkyl), cycloalkyl, heterocyclyl, aryl, or heteroaryl;

wherein each alkyl and O(alkyl) is optionally and independently substituted with one or more substituents independently selected from the group consisting of halogen, CN, $NO_2$, $NH_2$, OH, O(alkyl), cycloalkyl, heterocyclyl, aryl, and heteroaryl; and wherein each cycloalkyl, heterocyclyl, aryl, and heteroaryl is optionally and independently substituted with one or more substituents independently selected from the group consisting of halogen, CN, $NO_2$, alkyl, haloalkyl, hydroxyalkyl, $NH_2$, OH, O(alkyl), cycloalkyl, heterocyclyl, aryl, and heteroaryl; and n is 0, 1, 2, or 3;

wherein the process comprises the following step:

deprotecting a compound of formula (IIA) or formula (IIGA):

(IIA)

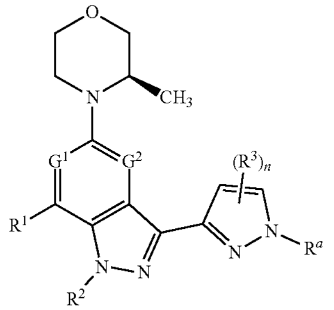

or (IIGA)

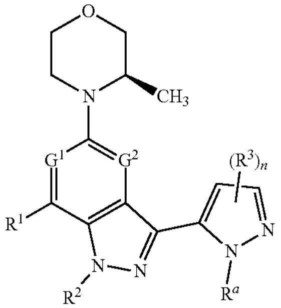

or a pharmaceutically acceptable salt or tautomer thereof, wherein:

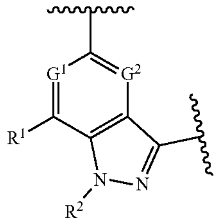

is

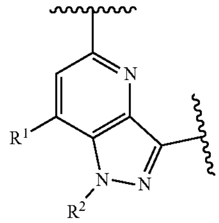

or

-continued

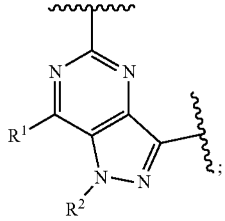

;

$R^1$ is alkyl or cyclopropyl, wherein the alkyl or cyclopropyl is substituted with one or more CN substituents;

$R^2$ is H or alkyl, wherein the alkyl is optionally substituted with one or more substituents independently selected from the group consisting of halogen, CN, $NO_2$, $NH_2$, OH, O(alkyl), cycloalkyl, heterocyclyl, aryl, and heteroaryl;

$R^a$ is $CH_2CH{=}CH_2$, $CH_2$-phenyl, $CH_2$-(p-methoxyphenyl), $C(O)CH_3$, $C(O)OC(CH_3)_3$, or tetrahydropyranyl (THP);

each $R^3$ is independently H, halogen, CN, alkyl, alkenyl, $NH_2$, OH, O(alkyl), O(haloalkyl), cycloalkyl, heterocyclyl, aryl, or heteroaryl;

wherein each alkyl and O(alkyl) is optionally and independently substituted with one or more substituents independently selected from the group consisting of halogen, CN, $NO_2$, $NH_2$, OH, O(alkyl), cycloalkyl, heterocyclyl, aryl, and heteroaryl; and wherein each cycloalkyl, heterocyclyl, aryl, and heteroaryl is optionally and independently substituted with one or more substituents independently selected from the group consisting of halogen, CN, $NO_2$, alkyl, haloalkyl, hydroxyalkyl, $NH_2$, OH, O(alkyl), cycloalkyl, heterocyclyl, aryl, and heteroaryl; and n is 0, 1, or 2;

with an acid selected from the group consisting of acetic acid, formic acid, hydrochloric acid, methanesulfonic acid, nitric acid, phosphoric acid, sulfuric acid, p-toluenesulfonic acid, trifluoroacetic acid, $(CH_3)_3SiCl$, and $(CH_3)_3SiOTf$, to obtain the compound of formula (II) above.

16. The process according to claim 15, wherein $R^a$ is tetrahydropyranyl (THP).

17. A compound of formula (IIA) or formula (IIGA):

(IIA)

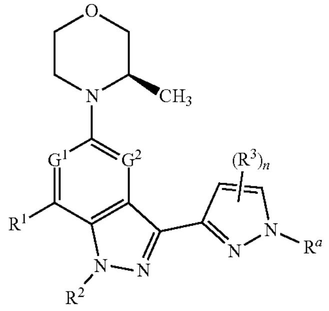

or

-continued (IIGA)

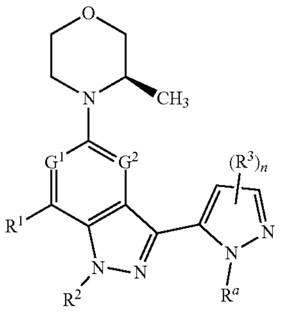

or a pharmaceutically acceptable salt or tautomer thereof, wherein:

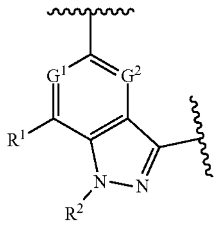

is

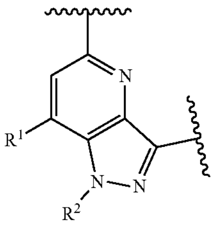

or

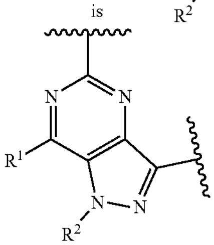

;

$R^1$ is alkyl or cyclopropyl, wherein the alkyl or cyclopropyl is substituted with one or more CN substituents;

$R^2$ is H or alkyl, wherein the alkyl is optionally substituted with one or more substituents independently selected from the group consisting of halogen, CN, $NO_2$, $NH_2$, OH, O(alkyl), cycloalkyl, heterocyclyl, aryl, and heteroaryl;

$R^a$ is $CH_2CH{=}CH_2$, $CH_2$-phenyl, $CH_2$-(p-methoxyphenyl), $C(O)CH_3$, $C(O)OC(CH_3)_3$, or tetrahydropyranyl (THP);

each $R^3$ is independently H, halogen, CN, alkyl, alkenyl, $NH_2$, OH, O(alkyl), O(haloalkyl), cycloalkyl, heterocyclyl, aryl, or heteroaryl;

wherein each alkyl and O(alkyl) is optionally and independently substituted with one or more substituents independently selected from the group consisting of halogen, CN, $NO_2$, $NH_2$, OH, O(alkyl), cycloalkyl, heterocyclyl, aryl, and heteroaryl; and wherein each cycloalkyl, heterocyclyl, aryl, and heteroaryl is optionally and independently substituted with one or more substituents independently selected from the group consisting of halogen, CN, $NO_2$, alkyl, haloalkyl, hydroxyalkyl, $NH_2$, OH, O(alkyl), cycloalkyl, heterocyclyl, aryl, and heteroaryl; and n is 0, 1, or 2.

18. The compound according to claim 17, wherein the compound is selected from the group consisting of:

11

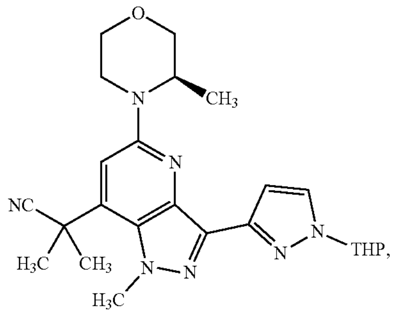

2c

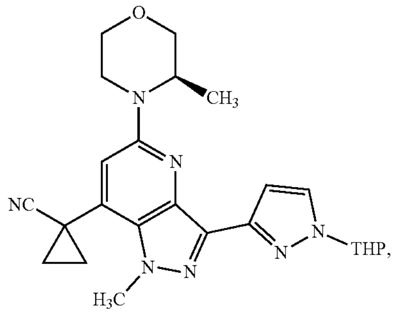

41

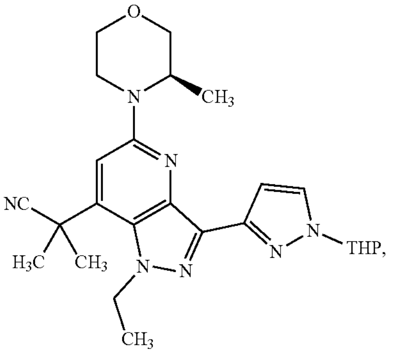

and

6j

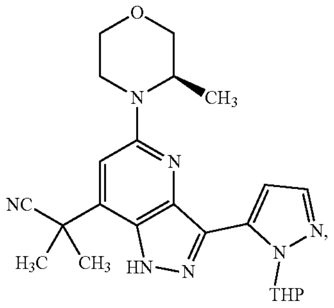

or a pharmaceutically acceptable salt or tautomer thereof.

* * * * *